United States Patent
Trout et al.

(10) Patent No.: US 9,138,659 B2
(45) Date of Patent: Sep. 22, 2015

(54) COMPOSITIONS, METHODS, AND SYSTEMS RELATING TO CONTROLLED CRYSTALLIZATION AND/OR NUCLEATION OF MOLECULAR SPECIES

(75) Inventors: Bernhardt Levy Trout, Lexington, MA (US); Patrick S. Doyle, Boston, MA (US); Trevor Alan Hatton, Sudbury, MA (US); Allan Stuart Myerson, Boston, MA (US); Ying Diao, Palo Alto, CA (US); Matthew E. Helgeson, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 201 days.

(21) Appl. No.: 13/216,018

(22) Filed: Aug. 23, 2011

(65) Prior Publication Data

US 2012/0076860 A1 Mar. 29, 2012

Related U.S. Application Data

(60) Provisional application No. 61/375,925, filed on Aug. 23, 2010, provisional application No. 61/418,767, filed on Dec. 1, 2010, provisional application No. 61/466,759, filed on Mar. 23, 2011.

(51) Int. Cl.
*B01D 9/00* (2006.01)
*A61K 9/14* (2006.01)
*B82Y 5/00* (2011.01)

(52) U.S. Cl.
CPC ... *B01D 9/00* (2013.01); *A61K 9/14* (2013.01); *A61K 9/146* (2013.01); *B82Y 5/00* (2013.01)

(58) Field of Classification Search
CPC ........... A61K 9/14; A61K 9/146; B01D 9/00; B82Y 5/00
USPC ............................................ 424/489; 117/64
See application file for complete search history.

(56) References Cited

U.S. PATENT DOCUMENTS

| | | | |
|---|---|---|---|
| 6,001,176 A | 12/1999 | Leiter et al. | |
| 6,017,390 A | 1/2000 | Charych et al. | |
| 6,593,118 B2 | 7/2003 | Heng | |
| 6,596,077 B2 | 7/2003 | Myerson | |
| 6,645,293 B2 | 11/2003 | Myerson et al. | |
| 6,759,521 B2 | 7/2004 | Myerson et al. | |
| 7,252,713 B2 | 8/2007 | Chayen et al. | |
| 7,329,592 B2 | 2/2008 | Myerson et al. | |
| 8,183,290 B2 * | 5/2012 | Tawa et al. | 514/569 |
| 2006/0109532 A1 | 5/2006 | Savas et al. | |
| 2013/0118399 A1 | 5/2013 | Chadwick et al. | |

OTHER PUBLICATIONS

Hamilton et al., J. Am. Chem. Soc. 2009, 131, 2588-2596.*

International Search Report and Written Opinion for PCT/US2011/048851 mailed May 14, 2012.
Aizenberg et al., Oriented Growth of Calcite Controlled by Self-Assembled Monolayers of Functionalized Alkanethiols Supported on Gold and Silver; Journal of the American Chemical Society; 1999; 121 (18); 4500-4509.
Aizenberg et al., Control of Crystal Nucleation by Patterned Self-Assembled Monolayers; Nature; 1999; 398 (6727); 495-498.
Beiner et al., Manipulating the Crystalline State of Pharmaceuticals by Nanoconfinement; Nano Letters; 2007; vol. 7, No. 5; 1381-1385.
Berman et al., Total Alignment of Calcite at Acidic Polydiacetylene Films—Cooperativity at the Organic-Inorganic Interface; Science; 1995; 269 (5223); 515-518.
Bunker et al., Ceramic Thin-Film Formation on Functionalized Interfaces Through Biomimetic Processing. Science; 1994, 264 (5155), 48-55.
Capes et al., Effect of Polymer Addition on the Contact Line Crystallisation of Paracetamol; CrystEngComm; 2007; 9; 84-90.
Carter et al., Topographically Directed Nucleation of Organic-Crystals on Molecular Single-Crystal Substrates; Journal of the American Chemical Society; 1993; 115 (24); 11521-11535.
Chayen et al., Porous Silicon: An Effective Nucleation-Inducing Material for Protein Crystallization; J. Mol. Bio; 2001; 312; 591-595.
Chayen et al., Experiment and Theory of Heterogeneous Nucleation of Protein Crystals in a Porous Medium; PNAS; 2003; vol. 103; No. 3; 597-601.
Cox et al., Selective Growth of a Stable Drug Polymorph by Suppressing the Nucleation of Corresponding Metastable Polymorphs; Angew. Chem. Int. Ed.; 2007; 46, 4333-4336.
D'Souza et al., Directed Nucleation of Calcite at a Crystal-Imprinted Polymer Surface; Nature; 1999; 398 (6725); 312-316.
Diao et al., The Role of Nanopore Shape in Surface-Induced Crystallization; Nature Materials; 2011; 10(11); 867-871.
Diao et al., Controlled Nucleation From Solution Using Polymer Microgels; Journal of the American Chemical Society; 2011; 133(11); 3756-3759.
Diao et al., Surface Design for Controlled Crystallization: The Role of Surface Chemistry and Nanoscale Pores in Heterogeneous Nucleation; American Chemical Society; 2011; 27(9); 5324-5334.
Diao et al., Nucleation Under Soft Confinement: Role of Polymer-Solute Interactions; Crystal Growth & Design; 2012, 12(1); 508-517.
Ha et al., Polymorph Selectivity Under Nanoscopic Confinement; Journal of American Chemical Society; 2004; 126; 3382-3383.

(Continued)

*Primary Examiner* — Michael G Hartley
*Assistant Examiner* — Robert Cabral
(74) *Attorney, Agent, or Firm* — Wolf, Greenfield & Sacks, P.C.

(57) ABSTRACT

The present invention generally relates to compositions, methods, and systems relating to controlled crystallization and/or nucleation of a molecular species. In some embodiments, the crystallization and/or nucleation of the molecular species may be controlled by tuning the surface chemistry and/or the morphology of a crystallization substrate. In some embodiments, the molecular species is a small organic molecule (e.g., pharmaceutically active agent).

26 Claims, 15 Drawing Sheets

(56) References Cited

OTHER PUBLICATIONS

Jackson et al., Vitrification and Crystallization of Organic Liquids Confined to Nanoscale Pores; Chem. Mater.; 1996; 8; 2128-2137.
Lee et al., Crystallization on Confined Enginered Surfaces: A Method to Control Crystal Size and Generate Different Polymorphs; Journal of the American Chemical Society; 2005; 127(43); 14982-14983.
Liberski et al., Screening for Polymorphs on Polymer Microarrays; Journal of Combinatorial Chemistry; 2008; 10(1); 24-27.
Maheshwari et al., Effect of Interfacial Hydrogen Bonding on the Freezing/Melting Behavior of Nanoconfined Liquids; J. Phys. Chem C.; 2010; 114; 4966-4972.
Page et al., Heterogeneous Nucleation in and Out of Pores; Physical Review Letters; 2006; 97(6); 065701-1-065701-4.
Price et al., Crystalline Polymorph Selection and Discovery With Polymer Heteronuclei; Journal of the American Chemical Society; 2005, 127(15); 5512-5517.
Saridakis, Protein Crystallization Facilitated by Molecularly Imprinted Polymers; PNAS; 2011; 108(27); 11081-11086.
Tanaka., Unusual Phase-Separation in a Polymer-Solution Caused by Asymmetric Molecular-Dynamics; Physical Review Letters; 1993; 71(19); 3158-3161.
Diao et al., Rational Design of Polymeric Nucleants for Controlling Nucleation From Solution; Presentation at the American Chemical Society meeting, Anaheim; Mar. 30, 2011.
Frenkel, Seeds of Phase Change; Nature; 2006; 443(12); 641.
Invitation to Pay Additional Fees for PCT/US2011/048851 mailed mailed Mar. 7, 2012.
International Preliminary Report on Patentability for PCT/US2011/048851 mailed Mar. 7, 2013.
Aguiar et al., Dissolution behavior of polymorphs of chloramphenicol palmitate and mefenamic acid. J Pharm Sci. Aug. 1969;58(8):983-7.
Allen et al., The Crystallization of Glycine Polymorphs from Emulsions, Microemulsions, and Lamellar Phases. Cryst Growth Des. 2002;2(6):523-7.
Alvarez et al., Polymorph Screening: Comparing a Semi-Automated Approach with a High Throughput Method. Cryst Growth Des. 2009;9(9):4181-8.
Bernstein et al., Concomitant Polymorphs. Angewandte Chem Int Ed. Dec. 3, 1999;38(23):3440-61.
Bernstein, Polymorphism—A Perspective. Cryst Growth Des. 2011;11(3):632-50.
Briseno et al., Patterned growth of large oriented organic semiconductor single crystals on self-assembled monolayer templates. J Am Chem Soc. Sep. 7, 2005;127(35):12164-5.
Briseno et al., Patterning organic single-crystal transistor arrays. Nature. Dec. 14, 2006;444(7121):913-7.
Cacciuto et al., Onset of heterogeneous crystal nucleation in colloidal suspensions. Nature. Mar. 25, 2004;428(6981):404-6.
Canal et al., Correlation between mesh size and equilibrium degree of swelling of polymeric networks. J Biomed Mater Res. Oct. 1989;23(10):1183-93.
Chadwick et al., Controlling the Crystal Structure of Active Pharmaceutical Ingredients Using Heterogeneous Surfaces. Purdue University presentation Nov. 2011.
Chadwick et al., Heteroepitixial Control of Crystal Nucleation Using Crystalline Substrates. Oral presentation at the annual meeting of the American Institute of Chemical Engineers. Oct. 28-Nov. 2, 2012. Pittsburgh, PA.
Chadwick et al., Polymorphic control by heterogeneous nucleation—A new method for selecting crystalline substrates. Cryst Eng Comm. 2011;13(22):6625-9.
Chadwick et al., Toward the Rational Design of Crystalline Surfaces for Heteroepitaxy: Role of Molecular Functionality. Cryst Growth Des. 2012;12:1159-66.
Chen et al., Cross-nucleation between ROY polymorphs. J Am Chem Soc. Dec. 14, 2005;127(49):17439-44.
Curcio et al., Energetics of protein nucleation on rough polymeric surfaces. J Phys Chem B. Nov. 4, 2010;114(43):13650-5. doi:10.1021/jp106349d.
Czugler et al., Structure of the unstable monoclinic 1,2,3,5-tetra-O-acetyl-β-D-ribofuranose. Acta Cryst. Jan. 1981;37(1):172-7.
Davey et al., Crystal engineering—nucleation, the key step. Cryst Eng Comm. 2002;4(47):257-64. doi:10.1039/B203521A.
Dendukuri et al., Stop-flow lithography in a microfluidic device. Lab Chip. Jul. 2007;7(7):818-28. Epub May 21, 2007.
Desgranges et al., Insights into the molecular mechanism underlying polymorph selection. J Am Chem Soc. Nov. 29, 2006;128(47):15104-5.
Dey et al., The role of prenucleation clusters in surface-induced calcium phosphate crystallization. Nat Mater. Dec. 2010;9(12):1010-4. doi: 10.1038/nmat2900. Epub Nov. 14, 2010.
Diao et al., Controlled Nucleation From Solution Using Polymer Microgels with Tunable Structure. Abstract of presentation at the annual meeting of the American Institute of Chemical Engineers. Nov. 7-12, 2010. Salt Lake City, Utah.
Diao et al., Towards surface design to control crystallization: Understanding the roles of surface chemistry and morphology in heterogeneous nucleation. ACS Presentation Abstract No. 250. Boston, MA. Aug. 23, 2010.
Dunitz et al., Disappearing Polymorphs. Acc Chem Res. 1995;28(4):193-200.
Erdemir et al., Nucleation of crystals from solution: classical and two-step models. Acc Chem Res. May 19, 2009;42(5):621-9. doi:10.1021/ar800217x.
Gavish et al., The role of crystal polarity in alpha-amino acid crystals for induced nucleation of ice. Science. May 8, 1992;256(5058):815-8.
Getsoian et al., One-solvent polymorph screen of carbamazepine. Int J Pharm. Feb. 4, 2008;348(1-2):3-9. Epub Oct. 22, 2007.
Grzesiak et al., Comparison of the four anhydrous polymorphs of carbamazepine and the crystal structure of form I. J Pharm Sci. Nov. 2003;92(11):2260-71.
Ha et al., Phase Behavior and Polymorphism of Organic Crystals Confined within Nanoscale Chambers. Cryst Growth Des. 2009;9(11):4766-77.
Hall et al., The crystal structure of metanilic acid. Acta Cryst. 1965;18:301-6.
Harada et al., Formation of highly ordered rectangular nanoparticle superlattices by the cooperative self-assembly of nanoparticles and fatty molecules. Langmuir. Jun. 2, 2009;25(11):6407-12. doi:10.1021/la900013r.
Henck et al., Disappearing and reappearing polymorphs. The benzocaine:picric acid system. J Am Chem Soc. Mar. 7, 2001;123(9):1834-41.
Hilden et al., Capillary Precipitation of a Highly Polymorphic Organic Compound. Cryst Growth Des. 2003:3(6):921-6.
Hillier et al., Epitaxial interactions between molecular overlayers and ordered substrates. Phys Rev B Condens Matter. Nov. 15, 1996;54(19):14037-14051.
Hiremath et al., Controlling molecular crystal polymorphism with self-assembled monolayer templates. J Am Chem Soc. Dec. 28, 2005;127(51):18321-7.
Hooks et al., Epitaxy and Molecular Organization on Solid Substrates. Adv Mat. Feb. 2001;13(4):227-41.
Kelly et al., Solvent Effects on the Crystallization and Preferential Nucleation of Carbamazepine Anhydrous Polymorphs: A Molecular Recognition Perspective. Org Process Res Dev. 2009;13(6):1291-300.
Lang et al., Form IV of carbamazepine. J Pharm Sci. Apr. 2002;91(4):1186-90.
Larhrib et al., Characterisation and deposition studies of engineered lactose crystals with potential for use as a carrier for aerosolised salbutamol sulfate from dry powder inhalers. Eur J Pharm Sci. Jul. 2003;19(4):211-21.
Last et al., The Physicochemical Origins of Coincident Epitaxy in Molecular Overlayers: Lattice Modeling vs Potential Energy Calculations. J Phys Chem. 1999;103(32):6723-33.
Levene, Note on the Preparation of crystalline d-mannose and of crystalline d-ribose. J Biol Chem. 1934;108(2):419-20.
Nichols et al., Physicochemical characterization of the orthorhombic polymorph of paracetamol crystallized from solution. J Pharm Sci. Jun. 1998;87(6):684-93.

(56) References Cited

OTHER PUBLICATIONS

Nicholson et al., Stable Polymorphs Crystallized Directly under Thermodynamic Control in Three-Dimensional Nanoconfinement: A Generic Methodology. Cryst Growth Des. 2011;11(2):363-6.

Nokhodchi et al., Dissolution and mechanical behaviors of recrystallized carbamazepine from alcohol solution in the presence of additives. J Crystal Growth. Feb. 1, 2005;274(3-4):573-84.

Olmsted et al., The role of chemical interactions and epitaxy during nucleation of organic crystals on crystalline substrates. Cryst Eng Comm 2011;13(4):1070-3.

Page et al., Crystallization controlled by the geometry of a surface. J Am Chem Soc. Dec. 9, 2009;131(48):17550-1. doi:10.1021/ja9085512.

Page et al., Heterogeneous nucleation in and out of pores. Phys Rev Lett. Aug. 11, 2006;97(6):065701. Epub Aug. 10, 2006.

Peppas et al., Hydrogels in Biology and Medicine: From Molecular Principles to Bionanotechnology. Adv Mat. Jun. 2006; 18(11):1345-60.

Rodríguez-Hornedo et al., Significance of controlling crystallization mechanisms and kinetics in pharmaceutical systems. J Pharm Sci. Jul. 1999;88(7):651-60.

Rubin-Preminger et al., 3-Aminobenzenesulfonic Acid: A Disappearing Polymorph. Cryst Growth Design. 2005;5(4):1343-9.

Santiso et al., A general set of order parameters for molecular crystals. J Chem Phys. Feb. 14, 2011;134(6):064109. doi:10.1063/1.3548889.

Savas et al., Large-area achromatic interferometric lithography for 100 nm period gratings and grids. Journal of Vacuum Science & Technology. 1996;B14:4167-70.

Singh et al., Concomitant Crystallization of ROY on Patterned Substrates: Using a High Throughput Method to Improve the Chances of Crystallization of Different Polymorphs. Cryst Growth Des. 2009;9(2):1182-5. doi:10.1021/cg801055x.

Steiner, Unrolling the hydrogen bond properties of C—H•••O interactions. Chem Commun. 1997:727-34.

Stewart et al., Imprint Materials for Nanoscale Devices. Mrs Bulletin. Dec. 2005;30(12):947-51.

Ten Wolde et al., Enhancement of protein crystal nucleation by critical density fluctuations. Science. Sep. 26, 1997;277(5334):1975-8.

Trujillo et al., Grafted Functional Polymer Nanostructures Patterned Bottom-Up by Colloidal Lithography and Initiated Chemical Vapor Deposition (iCVD). Chemistry of Materials. 2009;21:742-50.

Turnbull, Kinetics of heterogeneous nucleation. J Chem Phys. 1950;18:198-203.

Van Meel et al., Design principles for broad-spectrum protein-crystal nucleants with nanoscale pits. Phys Rev Lett. Nov. 12, 2010;105(20):205501. Epub Nov. 8, 2010.

Vekilov, Dense Liquid Precursor for the Nucleation of Ordered Solid Phases from Solution. Cryst Growth Design. 2004;4(4):671-85.

Ward, Bulk crystals to surfaces: combining X-ray diffraction and atomic force microscopy to probe the structure and formation of crystal interfaces. Chem Rev. Jun. 2001;101(6):1697-725.

Webb et al., Problems with crystals. J Chem Educ. 1978;55(10):644.

Xia et al., Monodispersed Colloidal Spheres: Old Materials with New Applications. Advanced Materials. May 2000;12(10):693-713.

Yin et al., Colloidal nanocrystal synthesis and the organic-inorganic interface. Nature. Sep. 29, 2005;437(7059):664-70.

Yu et al., Thermochemistry and Conformational Polymorphism of a Hexamorphic Crystal System. J Am Chem Soc 2000;122(4):585-91.

Yu, Polymorphism in molecular solids: an extraordinary system of red, orange, and yellow crystals. Acc Chem Res. Sep. 21, 2010;43(9):1257-66. doi:10.1021/ar100040r.

\* cited by examiner

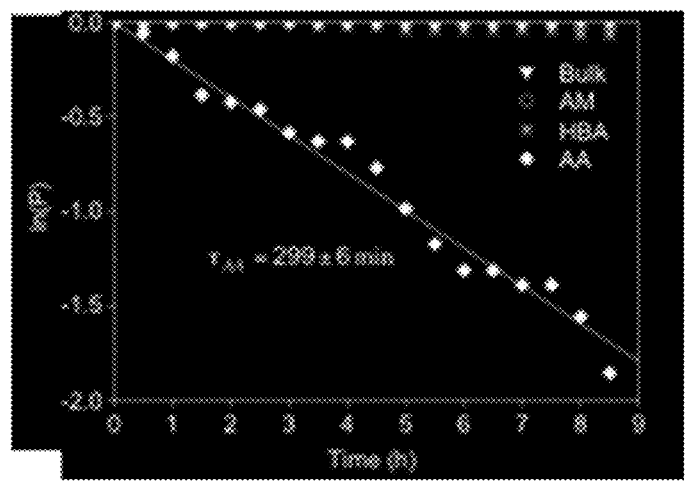
FIG. 18
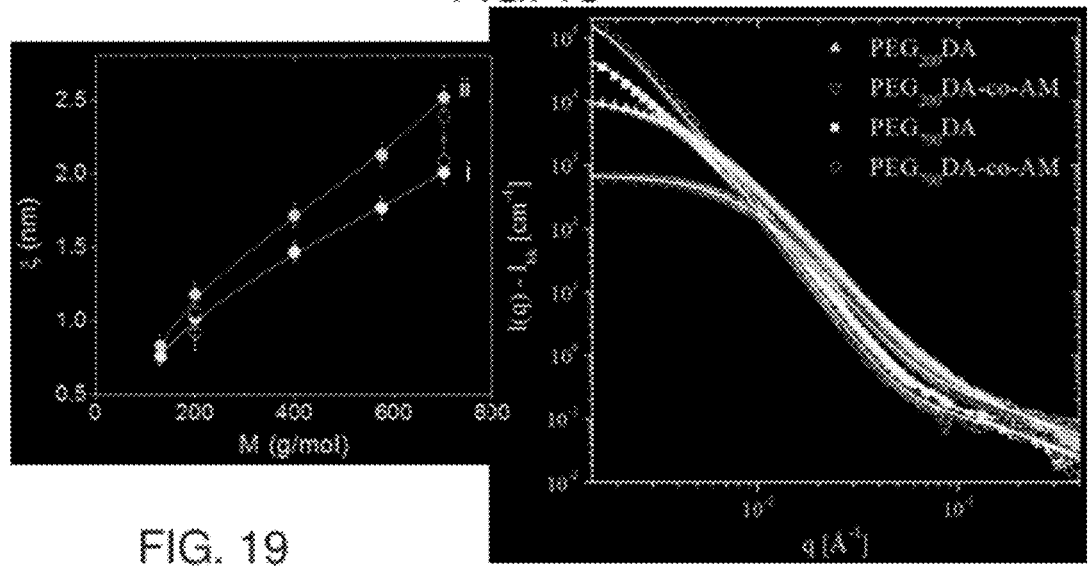
FIG. 19
FIG. 20

US 9,138,659 B2

COMPOSITIONS, METHODS, AND SYSTEMS RELATING TO CONTROLLED CRYSTALLIZATION AND/OR NUCLEATION OF MOLECULAR SPECIES

RELATED APPLICATIONS

This application claims priority to U.S. Provisional Patent Application Ser. No. 61/375,925, filed Aug. 23, 2010, and entitled "Compositions, Methods, and Systems Relating to Controlled Nucleation of Small Organic Molecules;" U.S. Provisional Patent Application Ser. No. 61/418,767, filed Dec. 1, 2010, and entitled "Compositions, Methods, and Systems Relating to Controlled Nucleation of Small Organic Molecules;" and U.S. Provisional Patent Application Ser. No. 61/466,759, filed Mar. 23, 2011, and entitled "Compositions, Methods, and Systems Relating to Controlled Nucleation of Small Organic Molecules," each of which are incorporated herein by reference in their entirety for all purposes.

FIELD OF THE INVENTION

The present invention generally relates to compositions, methods, and systems relating to controlled crystallization and/or nucleation of molecular species. In some cases, the molecular species is a small organic molecule (e.g., a pharmaceutically active agent).

BACKGROUND OF THE INVENTION

In many areas of science and technology, such as the production of pharmaceuticals, semiconductors, and optics, as well as the formation of biominerals, the ability to control crystallization is desired. As will be known to those of ordinary skill in the art, nucleation is generally a critical step in controlling the crystallization process. In most embodiments, crystallization starts with heterogeneous nucleation which occurs at random foreign surfaces. While many studies have been conducted regarding controlling crystallization of small organic molecules, crystallization is a complex and not well understood process. In addition, generally, small organic molecules may be crystallized in a variety of crystal patterns, and it is difficult, if not impossible, to predict under which conditions, a small organic molecule will crystallize in.

Accordingly, new compositions, methods, and systems are needed.

SUMMARY OF THE INVENTION

In some embodiments, a method of facilitating crystallization is provided comprising: exposing a substrate comprising pores to a molecular species; and causing molecular species to crystallize in the presence of at least a portion of the pores with an average induction time, wherein the average induction time is decreased by a factor of at least three, under substantially similar conditions, as compared to the average induction time using the substrate substantially free of pores.

In some embodiments, a method of facilitating crystallization is provided comprising exposing a substrate to a molecular species comprising a plurality of functional groups, wherein the substrate comprises a plurality of complimentary functional groups to the functional groups of the molecular species on at least one surface of the substrate; and causing the molecular species to crystallize on at least a portion of the substrate with an average induction time, wherein the average induction time is decreased by a factor of at least three, under substantially similar conditions, as compared to the average induction time using a polymeric material not comprising the complimentary functional groups.

In some embodiments, a method of facilitating crystallization is provided comprising exposing a substrate comprising a plurality of surface features, to a molecular species wherein the surface features have a cross section of at least 10 nm and have a shape and/or angle(s) which is selected to be complimentary to a known shape and/or angle(s) of a selected known crystal structure of the molecular species; and causing the molecular species to crystallize in at least a portion of the surface features, wherein molecular species is substantially formed having the selected crystal structure.

In some embodiments, a method of forming a plurality of particles comprising a crystallized molecular species is provided comprising providing a solution containing a plurality of polymeric particles having a plurality of pores and a molecular species; and causing the molecular species to crystallize in at least a portion of the plurality of pores.

In some embodiments, a composition is provided comprising a plurality of polymeric particles, wherein the particles comprise pores; and a pharmaceutically active agent crystallized in a least a portion of the pores.

In some embodiments, a method of administering a pharmaceutically active agent to a subject is provided comprising providing a plurality of polymeric particles comprising pores and a pharmaceutically active agent crystallized in at least a portion of the pores; and administering the plurality of polymeric particles to the subject.

In some embodiments, a method of making a pharmaceutical product is provided comprising crystallizing a pharmaceutically active agent in the presence of at least one excipient; forming a pharmaceutical product comprising the pharmaceutically active agent and the at least one excipient; wherein the process is free or essentially free of mechanical steps for altering the physical properties of the pharmaceutically active agent or the pharmaceutical product.

In some embodiments, a method is provided comprising providing a solution, a substrate comprising pores, and a pharmaceutically active agent, wherein the pharmaceutically active agent has a greater affinity to the substrate as compared to affinity between the solvent and the pharmaceutically active agent and compared to the affinity between the solvent and the substrate; and causing the pharmaceutically active agent to crystallize in at least a portion of the pores.

In some embodiments, a method of forming a plurality of particles comprising a crystallized active agent is provided comprising providing a solution, a substrate comprising a plurality of particles, and a pharmaceutically active agent, wherein the pharmaceutically active agent has a greater affinity to the substrate as compared to the affinity between the solvent and the pharmaceutically active agent and the affinity between the solvent and substrate; and causing the pharmaceutically active agent to crystallize associated with at least a portion of the substrate.

BRIEF DESCRIPTION OF THE DRAWINGS

FIG. 18 shows a statistical analysis of aspirin nucleation induction times with and without wells on the surface of a substrate, according to some embodiments.

FIG. 19 shows mesh sizes of polymer hydrogels estimated by equilibrium swelling measurements and SANS analysis, according to some embodiments.

FIG. 20 shows absolute SANS intensity spectra for polymer hydrogels, according to some embodiments.

Figure 1:
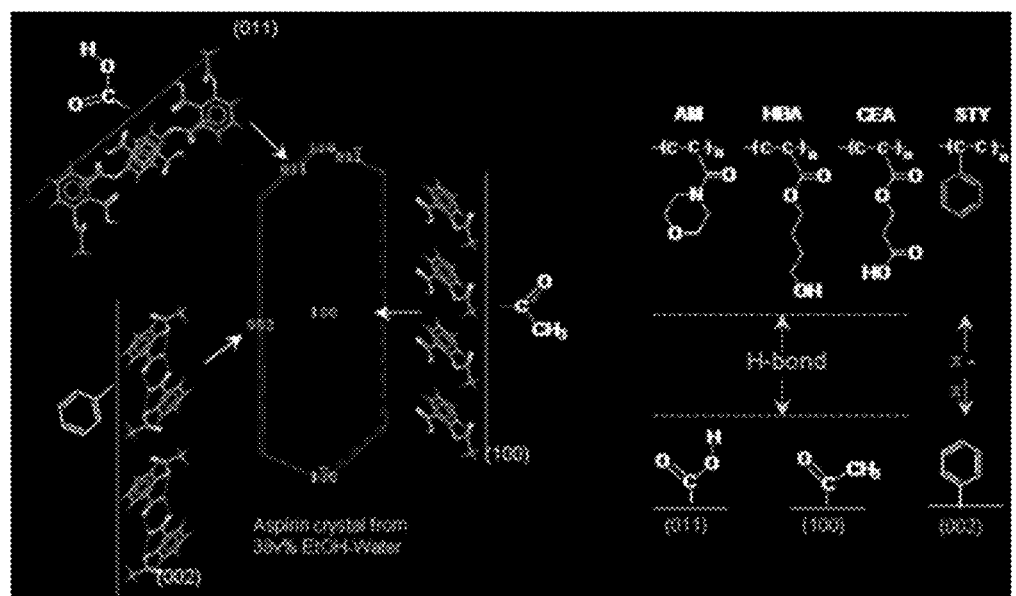
FIG. 1 illustrates varying interaction of a crystal phase of aspirin with different substrate functional groups, according to some embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to compositions, methods, and systems relating to the controlled crystallization and/or nucleation of molecular species (e.g., small organic molecules). The subject matter of the present invention involves, in some cases, interrelated products, alternative solutions to a particular problem, and/or a plurality of different uses of one or more systems and/or articles.

According to some aspects of the present invention, compositions, methods, and systems are provided for controlling the nucleation and/or crystallization of molecular species, e.g. from a solution by tuning the surface chemistry and/or morphology of crystallization substrates. The description provided herein describes how to select and/or vary a crystallization substrate (e.g., a material on which a molecular species is to crystallize) to affect the manner in which a molecular species crystallizes. The present invention recognizes that appropriate selection of the type of crystallization substrate (e.g., the chemical make-up of the substrate) as well as the morphology of the crystallization substrate (e.g., surface topology, porosity, etc.) used to promote nucleation of a small organic molecule can lead improve crystallization kinetics (e.g., reduced induction time) and/or crystallization of the molecular species in a selected crystal form. The methods and/or systems described herein can be used affect the crystallization rate and/or the type of crystal structure formed (e.g., the polymorph). For example, in some embodiments, the present invention recognizes that selection of the substrate as well as the porosity of the substrate used for nucleation of a small organic molecule can lead to a reduced average induction time as compared to a similar substrate that does have pores, under substantially similar conditions.

It should be understood that while many of the embodiments described herein discusses the use of a molecular species being a small organic molecule, this is by no way limiting and other molecular species may be employed (e.g., inorganic salts).

It is a feature of the invention that average crystallization induction times can be decreased significantly in all of the arrangements described herein for improved crystallization, for example, utilizing a porous substrate as compared to a non-porous substrate, utilizing a substrate with complimentary functional groups, utilizing a substrate with surface features complimentary to morphological features (shape, angle, etc.) of known crystal structures, etc., as compared to substrates not having those features. In all embodiments herein, one embodiment involves reducing the average induction time by a factor of at least 3 (or other factors described herein), under substantial identical conditions, as compared to the average induction time using a substrate substantially free of one or more (or all) of features described.

Selection, control, and/or modification of the crystallization substrate material (e.g., which forms the crystallization substrate) will now be described in more detail. In some embodiments, the substrate comprises a polymeric material. The polymeric material may form a hydrogel. In some cases, the polymeric material is porous. The polymeric material may also be formed such that at least one surface of the polymeric material comprises surface features to aid in the crystallization and/or nucleation processes. It should be understood, that while much of the discussion provided herein focuses on crystallization substrates comprising a polymer material (e.g., a hydrogel), this is by no means limited and other materials may be employed as crystallization substrate, providing the material is capable of comprising a selected surface chemistry and/or morphology (e.g., inner surface and outer surface morphologies).

As noted above, the crystallization and/or nucleation of a small organic molecule may be affected by the surface chemistry and/or morphology of a crystallization substrate. This discussion first focuses on the surface chemistry of the crystallization substrate. In some embodiments, the crystallization substrate material may be selected such that the surface(s) of the crystallization substrate material (e.g., outer surfaces and/or the surface of the pores, if present) comprises a plurality of at least one type of functional group which is complimentary to at least one functional group of the small organic molecule. That is, the functional groups of the substrate may be selected so as interact with a specific functional group of the organic small molecule of interest. The selection of complimentary combinations of functional groups can results in crystallization of the small organic molecule in 1) a particular crystal form (e.g., polymorph) and/or 2) with a faster induction time.

Without wishing to be bound by theory, selection of complimentary functional groups for the substrate (e.g. as a feature of the substrate material itself, and/or a surface coating and/or pattern of species on the substrate) may result in the formation of a particular crystal form of the small organic molecule due the preferential interactions between the portion of the small organic molecule having the function group and the substrate. The preferential interactions may cause the portion of the small organic molecule having the functional group to have a greater affinity for the surface of the substrate as compared to the other portions of the small organic molecule, thereby causing a plurality of the small organic molecules to associate with the substrate in a favored directional orientation. The alignment of a plurality of small organic molecules having the same approximate directional orientation can catalyze the nucleation/crystallization of the small organic molecule in a particular crystal phase. In embodiments where the crystal structure/form of the small molecule is known, the crystal structure/form can provide a basis for selecting the type of complimentary functional groups to be present on the surface of the crystallization substrate. That is, a known crystal structure may be examined to determine which functional groups of the small organic molecule are present on the surface of at least one face/edge of the crystal form and a type of functional group complimentary to that can be selected to be present of the substrate surface.

For example, as described in more detail in Example 1, a known polymorph of aspirin is associated with a substrate via different faces of the crystal depending on the functional groups on the surface of the substrate. As shown in FIG. 1, three different types of functional groups (e.g., —COOH, —COMe, and phenyl) are concentrated on three different faces of the crystal. Substrates were selected to comprise a plurality of complimentary functional groups to the three types of functional group present on each of the three crystal faces, and this resulted in aspirin crystallizing and associating with each of the substrates via different crystal faces. Thus, for molecular species with known crystal structures, the substrate can be selected comprising a plurality of functional groups on the surface which are selected to be complimentary to a functional group on/at the edge/face of the known crystal form of the molecular species. In embodiments where a crystal structure of the molecular species is not known (e.g., for a molecular species which has not been crystallized previously and/or for which a crystal structure has not yet been obtain), those of ordinary skill in the art will be able to select crystallization substrates with functional groups which are complimentary to the functional groups present for the molecular species, which may result in the formation of a variety of types of crystals. In addition, as described herein, the affinity for the small molecule for the substrate may also result in local regions of supersaturation.

Figure 13:
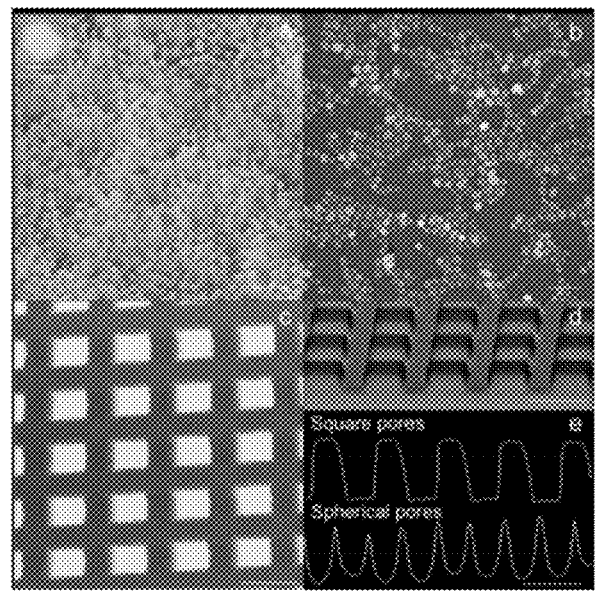
FIGS. 13a and 13c shows AFM images of hexagonal and square wells on the surface a substrate, according to some embodiments.
FIG. 13b shows a TEM image of iron oxide magnetic nanocrystals.
FIG. 13d shows a high resolution SEM image of Si square posts on Si wafer fabricated by AIL for templating square wells on the surface of a substrate, according to some embodiments.
FIG. 13e shows depth profiles of square and spherical wells of the surface of a crystallization substrate, according to some embodiments.

The selection of functional groups on the surface of the substrate may also be employed to improve the induction time for the crystallization of the molecular species. In such cases, the affinity for the molecular species to associate with the substrate may draw the molecular species towards the substrate, and hence increases the chances of nucleation, thus reducing the nucleation time. In some cases, the greater interaction between the small organic molecule and the substrate is embodied by higher concentrations of the small organic molecule in the pore of a substrate and/or near a surface of the substrate as compared to that in the bulk phase, for example, as illustrated by FIG. 13. That is, local area(s) of supersaturation may be present at the surfaces (e.g., outer surface and surface of the pores, if present) of the substrate.

In addition, in some embodiments of the present invention, the solvent, the crystallization substrate, and the small organic molecule may be selected such that the small organic molecule has a stronger interaction/affinity with the crystallization substrate as compared to the solvent. The rate of crystallization and/or nucleation may be increased in embodiments where the small organic molecule has preferred interactions with the crystallization substrate over the solvent, as compared to embodiments where there is no preferential interactions. In addition, the interaction/affinity between the substrate and the solvent may be greater than the interaction/affinity between the solvent and the substrate. Without wishing to be bound by theory, a greater interaction of the small organic molecule with the substrate as compared to any of the other interactions in the system (e.g., between the small organic molecule and the solvent, between the substrate and the solvent) may aid in reducing the average induction time, as the small organic molecule is drawn towards the substrate, and hence increases the chances of nucleation. Those of ordinary skill in the art will be capable of selecting combinations of solvents and crystallization substrate materials for a selected small organic molecule, based on the teaching described herein, which have the desired affinities/interactions between the solvent, the small organic molecule, and the crystallization substrate. In some embodiments, determining the concentration of a small organic molecule in the pores of a porous substrate may aid in determining an optimal substrate/solvent/small organic molecule combination.

Complimentary types functional groups (e.g., comprised on the surface of the substrate and the molecular species) will be known to those of ordinary skill in the art. The association may be based on formation of a bond, such as an ionic bond, a covalent bond (e.g., carbon-carbon, carbon-oxygen, oxygen-silicon, sulfur-sulfur, phosphorus-nitrogen, carbon-nitrogen, metal-oxygen, or other covalent bonds), a hydrogen bond (e.g., between hydroxyl, amine, carboxyl, thiol, and/or similar functional groups), a dative bond (e.g., complexation or chelation between metal ions and monodentate or multidentate ligands), Van der Waals interactions, or the like.

In some cases, the crystallization substrate material may be selected such that it comprises at least a plurality of hydroxyl functional groups, a plurality of carboxylic acid ester functional groups, a plurality of nitrogen containing base functional group, a plurality of aryl (e.g., phenyl) functional groups, a plurality of carboxyl functional group, a plurality of tertiary amide functional groups, or combinations thereof. As a non-limiting example, if the small organic molecule comprises an aryl group, the functional group on the surface of the substrate may be selected to be an aryl functional group, such that pi-interactions can occur between the surface of the substrate and the small organic molecule. As another example, if the small organic molecule comprises a hydrogen-bond donating group, the functional group on the surface of the substrate may be selected to be a hydrogen-bond accepting group. As a specific example, the small organic molecule may contain a carboxylic acid functionality and the surface of the substrate may contain a tertiary amide functionality. As another specific example, the small organic molecule may contain a carbonyl group and the surface of the substrate may contain a hydroxyl group. As yet another specific example, both the small organic molecule and the surface of the substrate may contain phenyl groups, and the interaction may be a pi-stacking interaction.

Those of ordinary skill in the art will be aware of methods of forming material comprising a plurality of a selected type of functional group. In some embodiments, the substrate comprises a polymer material, wherein a portion of the monomeric units forming the polymer each comprise a selected type of functional group. For example, the monomers shown below may be polymerized to form a polymer comprising the functional groups of the monomers:

In some embodiments, in addition to selecting a crystallization substrate based on the surface chemistry, the morphology of the crystallization substrate can also be varied to affect the crystallization and/or nucleation of a molecular species (e.g., small organic molecule). The morphology of a crystallization substrate may be varied by changing 1) the outer surface morphology (e.g., features such as wells) and/or 2) the inner surface morphology (e.g., such that the crystallization substrate is porous). While much of the discussion herein focuses on embodiments wherein only the outer surface morphology or the inner surface morphology is selected and/or optimized, this is by no means limiting, and those of ordinary skill in the art will be able to apply the teachings herein to embodiments where both the outer surface and the inner surface morphology are selected and/or optimized.

As described in more detail below, in some cases, the substrate may comprise a plurality of pores, wherein the small organic molecule may crystallize in at least some of the pores and/or the surface of the substrate may comprise a plurality of features (e.g., wells) wherein the small organic molecule may crystallize in at least a plurality of the pores and/or features. The pore and/or feature size and/or shape may be selected so as to increase the rate of crystallization (e.g., reduced induction time) and/or to promote crystallization of the small organic molecule is a selected crystal form.

Selection of the outer surface morphology will now be described in more detail. In some embodiments, the outer surface morphology of the crystallization substrate may be selected so as to promote crystallization (e.g., by increasing the induction rate and/or by promoting the formation of a certain crystal form) of a selected crystal form of a small organic molecule. At least one outer surface of the substrate may comprise a plurality of features having a shape which is complimentary to a known crystal form (e.g., polymorph) of the small organic molecule. For example, if a crystal form is known for a small organic molecule, the shape and/or angle(s) of the crystals are known or can be deduced/calculated. Based at least in part on the knowledge of the shape and/or angle(s) of the crystals, a complimentary shape and/or angle(s) of a plurality of features formed in the surface of the crystallization substrate may be selected. Without wishing to be bound by theory, selection of a complimentary shape and/or angle(s) of the features may promote the grown of the crystals as the features can direct the nucleation in a minimal-stress configuration due to a geometrical match between the crystal form and the features. As a non-limiting example, for a crystal form which is known to have an angle of approximately 120°, a hexagonal well on the surface of a substrate may promote the growth of that crystal form. As another non-limiting example, for a crystal form which is known to have an angle of approximately 90°, a square or well on the surface of a substrate may promote of the growth of that crystal form. As yet another non-limiting example, for a crystal form which is known to have an angle of approximately 60°, a triangular well on the surface of a substrate may promote the growth of that crystal form.

In some embodiments, the features formed on at least one surface of the substrate comprise a plurality of wells. The features formed in the outer surface of the crystallization substrate may be of any suitable shape and size. In some cases, each of the feature may have the shape of a circle, an oval, a triangle, a square, a rectangle, a trapezoid, a pentagon, a hexagon, an octagon, etc. In some cases, the shape does not comprise round edges. In some cases, the shape is not a circle or an oval. Generally, the features formed in the outer surface of the crystallization substrate have a cross section of at least 10 nm. In some cases, the cross section length is between about 10 nm and about 1000 nm, between about 10 nm and about 900 nm, between about 10 nm and about 800 nm, between about 10 nm and about 700 nm, between about 10 nm and about 600 nm, between about 10 nm and about 500 nm, between about 10 nm and about 400 nm, between about 10 nm and about 300 nm, between about 10 nm and about 200 nm, between about 10 nm and about 100 nm, between about 50 nm and about 500 nm, between about 100 nm and about 500 nm, or any range therein. In some cases, the features have an average depth of less than about 10 mm, or less than about 5 mm, or less than about 1 mm, less than about 500 um (micrometer), or less than about 100 um, or less than about 50 um, or less than about 1000 nm, or less than about 500 nm, or less than about 100 nm, or less than about 50 nm, or less than about 40 nm, or less than about 30 nm, or less than about 20 nm, or less than about 10 nm, or less than about 5 nm. In some cases, the features have an average depth of between about 10 mm and about 1 nm, between about 10 mm and about 100 nm, between about 10 mm and about 1 mm, between about 5 mm and about 1 mm, between about 5 mm and about 1 um, between about 50 nm and about 1 nm, between about 40 nm and about 1 nm, between about 30 nm and about 1 nm, between about 20 nm and about 1 nm, between about 10 nm and about 1 nm, or between about 10 nm and about 5 nm. The crystallization substrate may comprise any suitable number of features, for example, at least about or about 5 features, 10 features, 20 features, 50 features, 100 features, 200 features, 500 features, 1000 features, 2000 features, 5000 features, 10,000 features, 50,000 features, or more. In some cases, the features are formed in a single surface of the crystallization substrate. In some cases, the features are formed in more than one surface of the crystallization substrate. The size and/or shape of the crystallization substrate itself may be selected depending on the desired number, size, and/or shape of the features. Those or ordinary skill in the art will be aware of methods and systems for determining the size, shape, and/or number of features. Methods for forming suitable substrates comprising surface features will also be known to those of ordinary skill in the art and are described herein. In some embodiments, a substrate comprising a plurality of surface features is not porous.

Selection of the inner surface morphology will now be described in more detail. In some embodiments, the inner surface morphology of the crystallization substrate may be selected so as to promote crystallization of a selected small organic molecule (e.g., by increasing the crystallization kinetics). In some cases, a crystallization substrate may be porous (e.g., in addition to any surface wells). In some cases, a method comprises exposing a porous substrate to a small organic molecule and causing the small organic molecule to crystallize in at least a portion of the pores with a reduced induction time as compared to using the same substrate not having any pores under essential identical conditions (e.g., using the same or a substantially similar temperature, solvent(s), container(s), concentration of the molecular species, substrate shape, substrate size, substrate material, etc.). That is, the present invention recognizes that the porosity of the substrate used for nucleation of a small organic molecule can lead to a reduced average induction time as compared to a similar substrate that does not have pores. The term average induction time is given its ordinary meaning in the art and generally refers to the time elapsed prior to the formation of a detectable amount of a crystalline phase.

In some cases, the small organic molecule is crystallized in at least a portion of the pores of the substrate with an average induction time which is at least 2 times, at least 3 times, at least 4 times, at least 5 times, at least 6 times, at least 7 times, at least 8 times, at least 9 times, at least 10 times, at least 15 times, at least 20 times, at least 25 times, at least 50 times, at least 100, or greater, less than the average induction time using the substrate not having any pores, under essentially identical conditions. In some cases, the small organic molecule is crystallized in at least a portion of the pores of the substrate with an average induction time which is between about two times and about 1000 times, between about 2 times and about 100 times, between about 2 times and about 50 times, between about 2 times and about 40 times, between about 2 times and about 30 times, between about 2 times and about 10 times, etc., less than the average induction time using the substrate not having any pores, under essentially identical conditions. For example, according to the invention the average induction time for aspirin using a porous and non-porous substrate formed of 4-acryloylmorpholine polymer is, in one set of common conditions, 8.8 and 38.2 hours, respectively, and for a porous and non-porous substrate formed of 4-hydroxybutyl acrylate polymer are 54.6 and 243.9 hours, respectively. In some cases, the average induction time is the average of about 10, about 20, about 30, about 40, about 50, about 60, about 70, about 80, about 90, about 100, about 150, about 200, about 500, or more, experiment conducted under substantially similar conditions.

The pores formed in a crystallization substrate may comprise a range of sizes and/or be substantially uniform in size. In some cases, the pores may or might not be visible using imaging techniques (e.g., scanning electron microscope). The pores may be open and/or closed pores. In some cases, the substrate comprises pores having dimensions from 1-10 nanometers, and/or from 10-1000 nanometers and/or from 1-100 microns. In some embodiments, the average pore size is less than about 10 nm. In some embodiments, the average pore size is between about 1 nm and about 2 nm, between about 1 nm and about 5 nm, between about 0.1 nm and about 10 nm, between about 0.01 nm and about 10 nm, between about 0.5 nm and about 2.5 nm, or between about 1 nm and 20 nm. In some cases, the average pore size is about 0.1 nm, about 0.5 nm, about 1 nm, about 2 nm, about 3 nm, about 4 nm, about 5 nm, about 6 nm, about 7 nm, about 8 nm, about 9 nm, about 10 nm, about 20 nm, about 50 nm, about 100 nm, or about 200 nm. In some cases, the pore size may be selected so as to facilitate the crystallization (e.g., as described in the examples). Those or ordinary skill in the art will be aware of methods and systems for determining the size of the pores. Methods for forming suitable substrates comprising features will also be known to those of ordinary skill in the art and are described herein. In some cases, the substrate comprising a plurality of pores is provided as a plurality of particles. That is, the substrate comprises a plurality of porous particles. The size of the pores may be based on a variety of methods, including polymerizing a material in a plurality of substantially similar materials comprising different pore sizes (or mesh sized). In some cases, the optimal pore size may be estimated based on the critical nucleus size (e.g., see Examples).

In some embodiments, wherein the crystallization substrate comprises a hydrogel, the pore size may be better defined as a mesh size. In some embodiments, the average mesh size is less than about 10 nm. In some embodiments, the average mesh size is between about 1 nm and about 2 nm, between about 1 nm and about 5 nm, between about 0.1 nm and about 10 nm, between about 0.01 nm and about 10 nm, between about 0.5 nm and about 2.5 nm, or between about 1 nm and 20 nm. In some cases, the average mesh size is about 0.1 nm, about 0.5 nm, about 1 nm, about 2 nm, about 3 nm, about 4 nm, about 5 nm, about 6 nm, about 7 nm, about 8 nm, about 9 nm, about 10 nm, about 20 nm, about 50 nm, about 100 nm, or about 200 nm. Those of ordinary skill in the art will be aware of suitable methods and techniques for determining the mesh size of a hydrogel, including, but no limited to, small angle neutron scattering (SANS) measurements and equilibrium swelling measurements (e.g., see description of measurements described in Example 4).

SANS techniques and methods will be known to those of ordinary skill in the art. In some cases, SANS comprises forming a hydrogel in a scattering cell (e.g., by filling the cell with hydrogel precursors and initiating polymerization in the cell (e.g., by exposing the cell to UV irradiation)) or providing the hydrogel to the scattering cell. In some cases, the path length through the cell is about 1 mm SANS instruments are commercially available. In some cases, the cell may be maintained at about 25° C. and the samples may be equilibrized in this atmosphere for at least 30 minutes prior to the measurement. Scattering using incident neutrons of wavelength $\lambda=6$ Å and a wavelength spread (FWHM) of $\Delta\lambda/\lambda=11\%$ can be collected at detector distances of 1 m with 20 cm offset, 4 m, and 13.5 m for high-q measurements. Scattering using incident neutrons of wavelength $\lambda=8.09$ Å and a wavelength spread (FWHM) of $\Delta\lambda/\lambda=11\%$ can be collected at a detector distances of 15.3 m for low-q measurements. USANS measurements were performed on the BT5 perfect crystal diffractometer within the 6CB sample environment. Data may be reduced using a commercially available software program (e.g., NIST IGOR) to determine the mesh size. Further details of suitable calculations are described in Example 4.

The crystallization substrate may be of any suitable shape, size, or form. In some cases, the substrate may be a planar surface and/or a portion of a container. Non-limiting examples of shapes include sheets, cubes, cylinders, hollow tubes, spheres, and the like. In some cases, the maximum dimension of the substrate in one dimension may be at least about 1 mm, at least about 1 cm, at least about 5 cm, at least about 10 cm, at least about 1 m, at least about 2 m, or greater. In some cases, the minimum dimension of the substrate in one dimension may be less than about 50 cm, less than about 10 cm, less than about 5 cm, less than about 1 cm, less than about 10 mm, less than about 1 mm, less than about 1 um, less than about 100 nm, less than about 10 nm, less than about 1 nm, or less.

In some cases, the substrate may comprise a plurality of particles (e.g., polymeric particles). In some cases, a particle may be a nanoparticle, i.e., the particle has a characteristic dimension of less than about 1 micrometer, where the characteristic dimension of a particle is the diameter of a perfect sphere having the same volume as the particle. The plurality of particles, in some embodiments, may be characterized by an average diameter (e.g., the average diameter for the plurality of particles). In some embodiments, the diameter of the particles may have a Gaussian-type distribution. In some cases, the plurality of particles may have an average diameter of less than about an average diameter of less than about 5 mm, or less than about 4 mm, or less than about 3 mm, or less than about 2 mm, or less than about 1 mm, or less than about 500 um, or less than about 100 um, or less than about 50 um, or less than about 10 um, or less than about 1 um, or less than about 800 nm, or less than about 500 nm, or less than about 300 nm, or less than about 250 nm, or less than about 200 nm, or less than about 150 nm, or less than about 100 nm, or less than about 50 nm, or less than about 30 nm, or less than about 10 nm, or less than about 3 nm, or less than about 1 nm, in some cases. In some embodiments, the particles may have an average diameter of at least about 5 nm, at least about 10 nm, at least about 30 nm, at least about 50 nm, at least about 100 nm, at least about 200 nm, at least about 500 nm, at least about 800 nm, at least about 1000 nm, at least about 10 um, at least about 50 um, at least about 100 um, at least about 500 um, at least about 1 mm, at least about 2 mm, at least about 3 mm, at least about 4 mm, at least about 5 mm, or greater. In some cases, the plurality of the particles have an average diameter of about 10 nm, about 25 nm, about 50 nm, about 100 nm, about 150 nm, about 200 nm, about 250 nm, about 300 nm, about 500 nm, about 800 nm, about 1 mm, about 2 mm, about 3 mm, about 4 mm, about 5 mm, or greater.

Those of ordinary skill in the art will be aware of methods of forming materials having the desired surface chemistries and morphologies depending of the selected application and small organic molecule.

In some embodiments, the crystallization substrate comprises a polymer. Polymers generally are extended molecular structures comprising backbones which optionally contain pendant side groups, wherein the term backbone is given its ordinary meaning as used in the art, e.g., a linear chain of atoms within the polymer molecule by which other chains may be regarded as being pendant. Typically, but not always, the backbone is the longest chain of atoms within the polymer. A polymer may be a co-polymer, for example, a block, alternating, or random co-polymer. A polymer may also comprise a mixture of polymers. In some embodiments, the polymer may be acyclic or cyclic. A polymer may be crosslinked, for example through covalent bonds, ionic bonds, hydrophobic bonds, and/or metal binding. A polymer may be obtained from natural sources or be created synthetically.

An exemplary, non-limiting list of polymers that are potentially suitable for use in the invention includes polysaccharides; polynucleotides; polypeptides; peptide nucleic acids; polyurethane; polyamides; polycarbonates; polyanhydrides; polydioxanone; polyacetylenes and polydiacetylenes; polyphosphazenes; polysiloxanes; polyolefins; polyamines; polyesters; polyethers; poly(ether ketones); poly(alkaline oxides); poly(ethylene terephthalate); poly(methyl methacrylate); polystyrene; poly(lactic acid)/polylactide; poly(glycolic acid); poly(lactic-co-glycolic acid); poly(caprolactone); polysaccharides such as starch; poly(orthoesters); poly (anhydrides); poly(ether esters) such as polydioxanone; poly (carbonates); poly(amino carbonates); and poly (hydroxyalkanoates) such as poly(3-hydroxybutyrate) and poly(3-hydroxybutyrate-co-3-hydroxyvalerate) and derivatives and block, random, radial, linear, or teleblock copolymers, cross-linkable materials such as proteinaceous materials and/or blends of the above. Also suitable are polymers formed from monomeric alkylacrylates, alkylmethacrylates, alpha-methylstyrene, vinyl chloride and other halogen-containing monomers, maleic anhydride, acrylic acid, acrylonitrile, and the like. Monomers can be used alone, or mixtures of different monomers can be used to form homopolymers and copolymers. Other potentially suitable polymers are described in the Polymer Handbook, Fourth Ed. Brandrup, J. Immergut, E. H., Grulke, E. A., Eds., Wiley-Interscience: 2003, which is incorporated herein by reference in its entirety.

The polymer may have any suitable molecular weight. For example, in some embodiments, the polymer may have an average molecular weight greater than 1000 Da, in certain embodiments greater than 5000 Da, in certain embodiments greater than 10000 Da, in certain embodiments greater than 20000 Da, in certain embodiments greater than 50000 Da, in certain embodiments greater than 100000 Da, in certain embodiments greater than 500000 Da, or in certain embodiments greater than 1000000 Da. In some embodiments, the polymer may have at least 5 subunits, in certain embodiments at least 10 subunits, in certain embodiments at least 20 subunits, in certain embodiments at least 30 subunits, in certain embodiments at least 50 subunits, in certain embodiments at least 100 subunits, in certain embodiments at least 500 subunits, in certain embodiments at least 1000 subunits, or in certain embodiments at least 5000 subunits.

In some embodiments, a polymer may be biodegradable. In other embodiments, a polymer may be nondegradable. In embodiments where the particles are to be comprised in a composition for administration to a subject, the polymeric materials may be non-toxic and/or bioabsorbable.

In some cases, the polymeric material may form a hydrogel. As used herein, the term hydrogel is given its ordinary meaning as used in the art, e.g., a network of polymer chains in an aqueous dispersion medium. In some embodiments, a hydrogel may comprise a plurality of crosslinked polymer chains. In some cases, a hydrogel is formed by crosslinking the polymer chains. Non-limiting examples of polymers capable of forming hydrogels include, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups. In some cases, the polymeric materials may be an organogel, wherein the polymer network may be swollen by addition of an organic solvent. In some cases, the crystallization substrate comprising a plurality of porous hydrogel particles.

In some embodiments, the polymeric material may form a gel. As used herein, the term gel is given its ordinary meaning in the art and refers to polymer chains that may be crosslinked to form a network, wherein the network may be able to trap and contain fluids. Depending on the level of crosslinking, various properties of a particular gel can be tailored. For example, a highly crosslinked gel may generally be structurally strong and may resist releasing fluid under pressure. Those of ordinary skill in the art would be able to identify methods for modulating the degree of crosslinking in such gels.

Non-limiting examples of monomers which may be used for preparing polymeric materials for use with the invention are shown in Scheme 1. Scheme 1 also indicates possible functional groups. It should be understood that the monomers shown here are non-limiting, and those of ordinary skill in the art will be able to select other appropriate monomers and/or polymers for use with the invention.

Scheme 1:

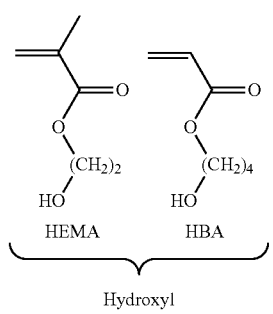

Hydroxyl

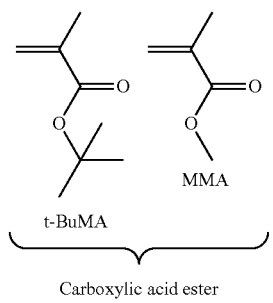

Carboxylic acid ester

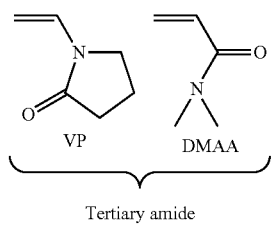

Tertiary amide

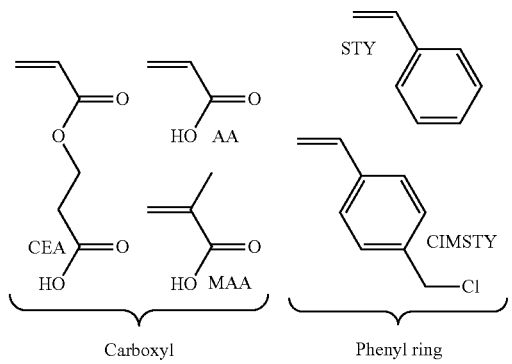

Carboxyl          Phenyl ring

-continued

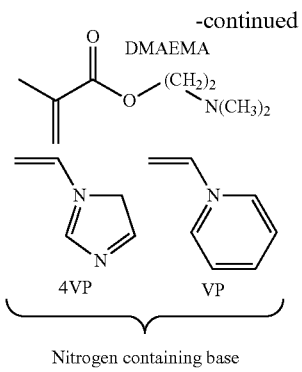

Nitrogen containing base

Those of ordinary skill in the art will be aware of a variety of methods for forming polymeric materials having a selected size and/or shape. In some embodiments, a polymeric material may be formed using UV polymerization. In some embodiments, a polymeric material may be formed by reacting at least one monomer and a crosslinking agent using UV irradiation. That is, the polymeric films may be synthesized by ultraviolet curing a mixture of one or more monomers and optionally a crosslinker (e.g., ethylene glycol dimethacrylate (EGDMA)). In some cases, a porous polymeric material (e.g., particles) can be formed using photopolmerization induce phase separation, polymerization with high molecular weight polymers or nanoemulsions as the porogen, chemical crosslinking, catalytic polymerization, etc.

In a particular embodiment, a polymer material may be formed by photopolymerization induced phase separation. Generally, a mixture of at least one monomer and a crosslinker are provided in a solvent. Upon exposure to electromagnetic radiation (e.g., UV irradiation), the polymerization of the monomer and reaction with the crosslinker occurs. As polymer chains reach a critical length, the dynamic asymmetry between the solvent molecules and the polymer cause local regions of high solvent concentration, which forms the pores. Removal of the solvent (e.g., via evaporation) leaves a porous polymer material.

Those of ordinary skill in the art will be aware of methods and techniques for forming polymeric materials comprising a desired outer surface morphology, including, but not limited to nanoimprint lithography, nanosphere lithography, and stop flow lithography. In some embodiments, the polymeric materials may be formed using a techniques termed herein as "nanoparticle imprint lithography" or NpIL. As described in more detail in Example 3, NpIL comprises providing a substrate and a plurality of particles and covalently linking (or otherwise immobilizing, e.g., via other strong bonding interactions, adhesion, etc.) the plurality of particles to the surface of a substrate to provide a lithography template. In some cases, this may be accomplished by crosslinking a functional group present on the surface of the substrate with a functional group on the particle. The particles may be associated with the substrate surface such that only a single layer of the particles is present on the substrate surface. This may be accomplished, in some embodiments, by selecting surface functionalities that are of such a length that they could not associate with a second layer of particles. Following association of the particles with the surface, any excess particles which do not become associated with the substrate can be removed (e.g., by washing the lithography template). General lithography techniques can then be carried out using the lithography template. For example, the lithograph template can be exposed to a polymeric precursor, wherein the polymeric precursor is cured (e.g., via exposure to UV irradiation) following the exposure. Thus, the polymeric material formed comprises an imprint of the lithography template. The polymeric material and the lithography template can then be separated (e.g., by physical manipulation), thus forming a crystallization substrate comprising a plurality of features. Other non-limiting techniques for forming features in the surface of a material comprise photofabrication, etching, electrodischarge machining, electrochemical machining, laser beam machining, wire electrical discharge grinding, focused ion beam machining, micromilling, micro-ultrasonic machining, and micropunching.

As noted above, while much of the discussion focuses on crystallization substrates comprising polymeric materials, this is by no ways limiting and a crystallization substrate may comprise non-polymeric materials. For example, in some embodiments the substrate may comprise a metal, an alloy, an inorganic material, etc. wherein the surface of the material comprises or is optionally functionalized with a plurality of functional groups, and wherein the material may be shaped and/or formed having the desired inner and/or outer morphologies. It should be understood that the functional groups may be a portion of the material, or may optionally be formed on the material (e.g., as a coating). For example, a material (e.g., polymeric or otherwise) may form a basis (e.g., core) of the substrate and the surfaces of the substrate may be associated with (e.g., coated) with a polymeric material as described herein comprising a plurality of functional groups.

Crystallization of molecular species (e.g., small organic molecules) may be carried out according to methods known to those of ordinary skill in the art. In some cases, a substrate (e.g., as described herein) may be exposed to a solution comprising a small organic molecule. Generally, the small organic molecule is substantially soluble in the solvent selected. In some cases, the solution comprising the solvent and the small organic molecule may be filtered prior to exposing the solution to the substrate. The small organic molecule may be present in the solvent at a concentration of about 0.05 M, about 0.1 M, about 0.2 M, about 0.3 M, about 0.4 M, about 0.5 M, about 0.75 M, about 1 M, about 2 M, or greater. Non-limiting examples of solvents include water, acetone, ethanol, acetonitrile, benzene, p-cresol, toluene, xylene, mesitylene, diethyl ether, glycol, petroleum ether, hexane, cyclohexane, pentane, dichloromethane (methylene chloride), chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and combinations thereof.

Those of ordinary skill in the art will be aware of methods for inducing crystallization. For examples, in some cases, a system comprising a substrate and a solution comprising the small organic molecule may be cooled. Alternatively, the solution comprising the small organic molecule may be concentrated (e.g., by evaporation of at least a portion of the solvent)

The methods and/or compositions of the present invention may find application relating to pharmaceutical compositions and/or methods, wherein the molecular species is a pharmaceutically active agent. As will be known to those of ordinary skill in the art, different polymorphs of pharmaceutically active agents can have significantly different properties including solubility, bioavailability, and/or stability Accordingly, the ability to control the formed polymorph of the pharmaceutically active agent (e.g., using the methods and systems described herein) provides the advantage of having the capability to form a selected polymorph based on the properties of the crystallization substrate. For embodiments where the crystals of the pharmaceutically active agent are not to be separated from the crystallization substrate (e.g., in embodiments wherein the pharmaceutically active agent is crystallized in the pore of the substrate), the substrate may be substantially non-toxic and/or bioabsorbable.

In some aspects of the present invention, methods are provided for forming a plurality of particles comprising a crystallized active agent (e.g., a crystallized pharmaceutically active agent). In some cases, the crystallized active agent is formed in at least a plurality of the pores, e.g., according to the methods described herein. For example, in some cases, the method comprises providing a solution containing a crystallization substrate comprising plurality of polymeric particles, wherein the polymeric polymers are porous. The polymeric materials used to form the polymeric particles may optionally be selected to comprise a plurality of functional groups to aid in the interaction between the polymeric particles and the active agent. The polymeric particles may be exposed to a solution comprising the pharmaceutically active agent. Using the methods and systems described herein, the pharmaceutically active agent may be crystallized in at least a portion of the plurality of pores of the polymeric particles. For example, a solution may be provided comprising the plurality of porous polymeric particles and the pharmaceutically active agent, and at least one method or system may be employed to induce crystallization, as described above. A composition comprising a plurality of polymeric particles and a pharmaceutically active agent crystallized in at least a portion of the pores may be formed and/or provided. The composition may be isolated and used in a variety of application. For example, for use in a pharmaceutical composition for administration to a subject.

The compositions, methods, and systems of the present invention may be find advantageous use in applications involving crystallized pharmaceutically active agents. Crystallization is a common technique used to purify pharmaceutically active agents in pharmaceutical manufacturing processes. Generally, after the pharmaceutically active agent has been crystallized, the crystals are granulated and blended with excipients in a series of solid state operations. The granulation and blending steps may be problematic for example, as the steps may be plagued by poor process control ability and/or final product uniformity, and/or the process parameters may be very sensitive to the properties of the specific type of pharmaceutically active agent. In addition, bulk crystallization of pharmaceutically active agents may not always provide a single type of polymorph of the pharmaceutically active agent and/or changes over time during a manufacturing process can cause different types of polymorphs to form. For example, a slight change in temperature may cause a pharmaceutically active agent to crystallize in a phase different than the desire phase. In addition, granulating and/or blending steps may induce changes in the crystal phase of the pharmaceutically active agent.

The methods, systems, and compositions as described may aid in reducing and/or eliminating typical processing steps such as granulation and/or blending, as well as reducing the probability that the pharmaceutically active agent crystallizes in an undesired polymorphic form. For example, as described herein, the methods and systems of the present invention can be used to promote the crystallization of a small organic molecule (e.g., a pharmaceutically active agent) and a specific polymorph, thus reducing the likelihood of the formation of an undesired polymorph. In addition, a pharmaceutically active agent may be crystallized in a plurality of polymeric particles, and these particles may be used directly in a pharmaceutical composition (e.g., they may be bound to form a tablet), thus reducing/eliminate typical processing steps.

Figure 2:
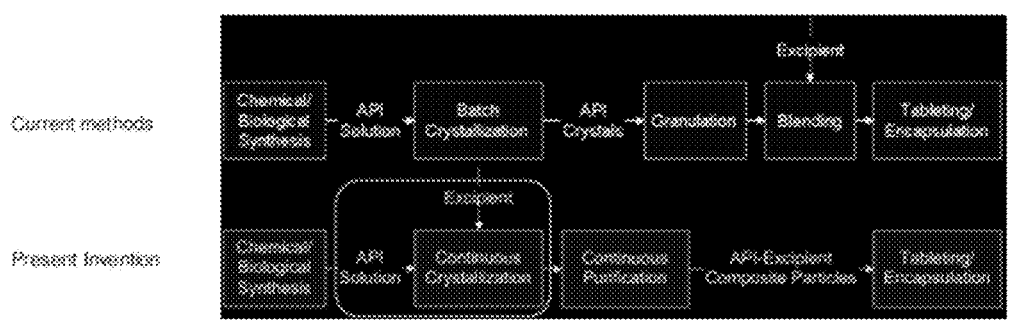
FIG. 2 provides flow charts of methods for manufacturing pharmaceutical compositions, according to known methods and methods of the invention, according to some embodiments.

Thus, the crystallization and/or nucleation techniques described herein can provide a greater ability to control the crystal phase of the pharmaceutically active agent, and/or the reduce or eliminate processing steps which may result in changes in the crystal phase that may occur during these steps (e.g., see FIG. 2).

In some embodiments methods are provided for making a pharmaceutical composition. In some cases, the method comprises crystallizing a pharmaceutically active agent in the presence of at least one excipient (e.g., a crystallization substrate comprising a plurality of polymeric particles, optionally porous, and optionally comprising a plurality of complimentary functional groups to the pharmaceutically active agent), forming a pharmaceutical composition comprising the pharmaceutically active agent and the at least one excipient. In some embodiments, the process is free or essentially free of mechanical steps for altering the physical properties of the pharmaceutically active agent or the pharmaceutical composition. In some cases, the process is essentially free of mechanical steps for reducing particle size of the pharmaceutically active agent and at least one excipient. That is, that the pharmaceutical composition may be prepared without the need for mechanical steps such as granulation and/or blending. The resulting pharmaceutical composition may be provided to a subject. In some cases, prior to administration to the subject, the pharmaceutical composition may be formed into a pharmaceutical product suitable for administration. For example, the particles may be contained in a capsule (e.g., including gel capsules), as a tablet, in a solution (e.g., for injection), etc.

In some embodiments, methods are provided for administering a pharmaceutically active agent to a subject. In some cases, the method comprises providing a crystallization substrate comprising a plurality of polymeric particles having a plurality of pores or features and a pharmaceutically active agent crystallized in at least a portion of the pores or features; and administering the plurality of polymeric particles to the subject (e.g., a human). Methods and compositions comprising a plurality of polymeric particles having a pharmaceutically active agent crystallized in at least a portion of the pores or features are described herein.

The term "small molecule" is art-recognized and refers to a composition which has a molecular weight of less than about 2000 g/mole, or less than about 1000 g/mole, and even less than about 500 g/mole. Small molecules may include, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides, or polypeptides. In some cases, the small organic molecule is a pharmaceutically active agent (i.e., a drug). A pharmaceutically active agent may be any bioactive agent. In some embodiments, the pharmaceutically active agent may be selected from "Approved Drug Products with Therapeutic Equivalence and Evaluations," published by the United States Food and Drug Administration (F.D.A.) (the "Orange Book"). In a particular embodiment, the pharmaceutically active agent is aspirin or acetaminophen.

The compositions and/or crystals described herein may be used in "pharmaceutical compositions" or "pharmaceutically acceptable" compositions, which comprise a therapeutically effective amount of one or more of the polymers or particles described herein, formulated together with one or more pharmaceutically acceptable carriers, additives, and/or diluents. The pharmaceutical compositions described herein may be useful for diagnosing, preventing, treating or managing a disease or bodily condition including conditions characterized by oxidative stress or otherwise benefiting from administration of an antioxidant. Non-limiting examples of diseases or conditions characterized by oxidative stress or otherwise benefiting from administration of an antioxidant include cancer, cardiovascular disease, diabetes, arthritis, wound healing, chronic inflammation, and neurodegenerative diseases such as Alzheimer Disease.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid, gel or solid filler, diluent, excipient, or solvent encapsulating material, involved in carrying or transporting the subject compound, e.g., from a device or from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, a "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition.

The following are herein incorporated by reference in their entirety for all purposes: U.S. Provisional Patent Application Ser. No. 61/375,925, filed Aug. 23, 2010, and entitled "Compositions, Methods, and Systems Relating to Controlled Nucleation of Small Organic Molecules;" U.S. Provisional Patent Application Ser. No. 61/418,767, filed Dec. 1, 2010, and entitled "Compositions, Methods, and Systems Relating to Controlled Nucleation of Small Organic Molecules;" and U.S. Provisional Patent Application Ser. No. 61/466,759, filed Mar. 23, 2011, and entitled "Compositions, Methods, and Systems Relating to Controlled Nucleation of Small Organic Molecules."

The following examples are intended to illustrate certain embodiments of the present invention, but do not exemplify the full scope of the invention.

Example 1

The following example provides both prophetic and working examples of methods and systems of the present invention. In this Example, exemplary methods and systems for controlling the nucleation of small organic compounds from solution by tuning the surface chemistry and morphology of amorphous substrates are described. Polymers are synthesized with various surface chemistries and pore structures to expedite the nucleation of small organic molecules.

In many areas of science and technology, such as the production of pharmaceuticals, semiconductors, and optics, as well as the formation of biominerals, the ability to control crystallization is desired. Nucleation is an important step in controlling the crystallization process. Generally, crystallization starts with heterogeneous nucleation which occurs at random foreign surfaces.

Controlling nucleation kinetics and nucleation density by adjusting surface chemistry: Nucleation is an activated process. The presence of interfaces may alter the free energy barrier of nucleation through various means (e.g., the degree of interaction between the substrate and the crystallizing molecule by adjusting the substrate surface chemistry).

To impart various surface chemistries, crosslinked polymers were prepared to heterogeneously nucleate the active pharmaceutical ingredient (API, also herein described as a pharmaceutically active agent) of interest. The polymers were crosslinked, resulting in minimized solvent uptake and stabilized surface functionality. Polymers were synthesized via photo polymerization method. UV curable monomers that could interact with the API of interest (e.g., via hydrogen bonds or pi-pi stacking) were selected.

One API employed was aspirin, and monomers with varying functional groups were selected and divided into a number of types according to the main functionality contained (e.g., see Scheme 1). Group (a) includes 2-hydroxyethyl methacrylate (HEMA), acrylic acid (AA) and methacrylic acid (MAA) which contain carboxyl or hydroxyl groups that provide both hydrogen bond donors and acceptors. Groups (b) and (c) include tertiary amides and amines that are rich in hydrogen bond acceptors, and they are N,N,-dimethylacrylamide (DMAA), vinylpyrrolidone (VP), 4-Acryloylmorpholine (AM) in group (b) and 4-vinylpyridine (4VP), vinylimidazole (VI), 2-dimethylamino ethyl methacrylate (DMAEMA) in group (c). Monomers in group (d), methyl methacylate (MMA) and tert-butyl methacrylate (t-BuMA), contain the carboxylic acid ester functionality that is also seen in aspirin. In group (e) are two phenyl-ring-containing monomers, styrene (STY) and chloromethylstyrene (CIMSTY).

To determine the relative nucleation activities of surfaces and to select the surface chemistries which best promote nucleation, a screening method was developed where the API of interest was crystallized on the candidate polymer films by static isothermal crystallization method and the nucleation area density on the polymer film was used as a parameter to indicate the nucleation activity of surfaces.

Specifically, the polymer films were synthesized by UV curing a mixture of a monomer and a crosslinker, ethylene glycol dimethacrylate (EGDMA), then immersed in supersaturated aspirin-toluene solution to perform static isothermal crystallization. The crystal densities on the polymer films are shown in FIG. 3.

Figure 3:
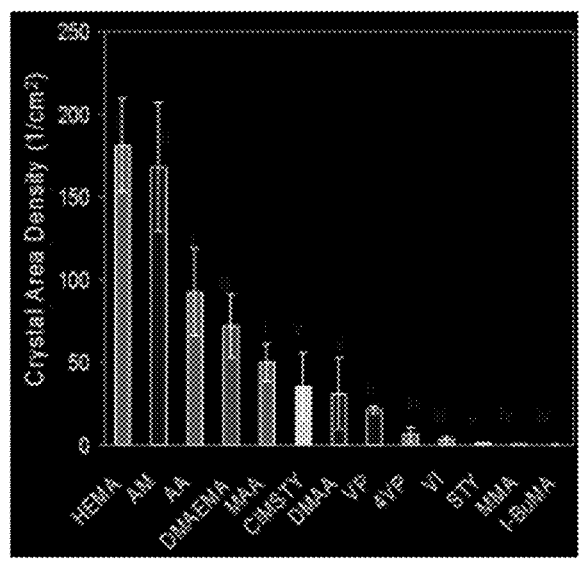
FIG. 3 shows the nucleation density of aspirin on a variety of substrate films, according to some embodiments.

In FIG. 3: Nucleation density of aspirin on polymer films. Columns representing polymers from groups (a), (b), (c), (d), (e) are numbered (i), (ii), (iii), (iv), and (v), respectively. Error bars were derived from three repeats.

To further quantify the surface chemistry effect on nucleation kinetics, nucleation induction time distribution was measured with the API of interest. Nucleation induction time is an indicator of the surface nucleation activity because it can be shortened when the presence of a surface lowers the free energy barrier of nucleation. Due to the stochastic nature of nucleation events, a significant number of experiments were performed to obtain the probability distribution of nucleation induction time.

As an example of induction time measurements, polymer plates were prepared by UV polymerizing the mixture of a monomer and the crosslinker divinylbenzene held by Teflon holders. Subsequent drying under vacuum removed unreacted monomer molecules. Monomers used to synthesize polymer plates were 4-Acryloylmorpholine (AM), 4-Hydroxybutyl acrylate (HBA), 2-Carboxyethyl acrylate (CEA), and styrene (STY). AM, HBA, and CEA served as positive controls, whilst STY a negative control. Each polymer plate was inserted together with the Teflon holder vertically into the aspirin solution, and then the solution was quenched to initiate nucleation. The starting concentration and the nucleation temperature were chosen such that the supersaturation produced was high enough to give reasonably short induction time but low enough to suppress bulk nucleation. 48 vials of each polymer sample were tested simultaneously and the fraction of vials crystallized was recorded as a function of time to produce a plot of cumulative probability distribution of induction time, as shown in FIG. 4.

Figure 4:
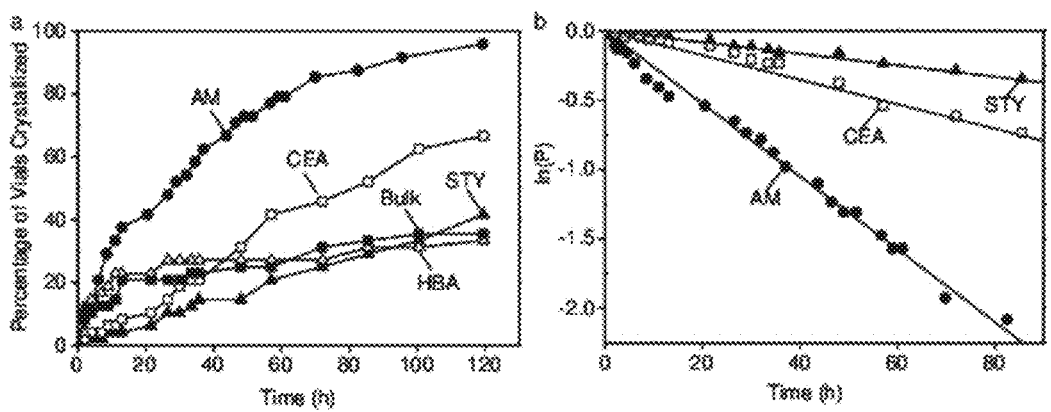
FIG. 4 shows cumulative probability distribution of nucleation induction time (a) and statistical analysis on the same data sets (b) obtained with polymers synthesized via bulk polymerization, according to some embodiments.

In FIG. 4: Cumulative probability distribution of nucleation induction time (a) and statistical analysis on the same data sets (b) obtained with polymers synthesized via bulk polymerization. Crystallization of aspirin was performed at supersaturation S=4.75. The linear regression in 2(b) follows the formula $\ln(P)=-t/\tau$ to obtain the average induction time $\tau$. P is the probability for no crystallization event to occur within time t. Since the STY, HBA and bulk samples produced comparable nucleation rate, only the STY data was regressed. The results of linear fitting are i) STY $\ln(P)=-t/243.9$, $R^2=0.987$; ii) CEA $\ln(P)=-t/113.6$, $R^2=0.978$; iii) HBA $\ln(P)=-t/38.2$, $R^2=0.995$.

Controlling nucleation kinetics by adjusting surface morphology: Besides surface chemistry, surface morphology, especially porous structures, may also play an important role in controlling nucleation kinetics and polymorphism. However, no study has been reported on controlling nucleation kinetics of small organic compounds with polymers of nanoscopic pores, nor a rigorous experimental method to evaluate the nucleation activity of the porous material.

The methods used to make porous polymer substrates or microparticles include photopolymerization induced phase separation (PIPS), polymerization with high molecular weight polymers or nanoemulsions as the porogen, etc. The method to measure nucleation kinetics is aforementioned.

For example, by the PIPS method, the mixture of a monomer and the crosslinker divinylbenzene dissolved in ethanol was subjected to UV irradiation to initiate the polymerization. As the molecular weight of the polymer increases to a critical point, dynamic asymmetry between solvent molecules and the polymer lead to nucleation and growth of solvent-rich regions within the polymer matrix. Subsequent evaporation of the solvent during the vacuum drying leaves pores on the polymer films. One common feature shared by most porous surfaces is a raised edge surrounding the pore region, which may be a sign of eruptional behavior caused by fast solvent evaporation under vacuum. As determined by AFM, the pores found on polymer sample AM were around 100 nm in width and 4 nm in depth. Comparatively, polymer sample HBA carried pores about 50 nm in width and 5-8 nm in depth. The non-porous AM and HBA samples were synthesized by bulk polymerization method and used as a control and had relatively smooth surfaces despite a few impurities. Table 1 showed that the presence of specific pore structure on polymer sample AM and HBA greatly shortened the nucleation induction time, and hence expedited nucleation.

TABLE 1

Comparison of the average nucleation induction time of aspirin with nonporous and porous polymers.

| Polymer type | Supersaturation | Average induction time $\tau$ (h) AM | HBA |
|---|---|---|---|
| Non-porous | S = 4.75 | 38.2 | 243.9 |
| Porous | S = 4.2 | 8.8 | 54.6 |

Controlling crystal orientation via specific molecular interactions: From the manufacturing point of view, it is desired to control the crystal morphology by designing the nucleation substrate. Researchers have oriented the Calcite crystals via electrostatic interactions and epitaxial relationships in the aqueous system. However, no study appears to have been completed on the orientation of small organic molecules on amorphous polymeric substrates. In this example, the API of interest was heterogeneously crystallized on polymer surfaces of various chemistries. The preferred orientation of the API crystal with respect to the top surface of the polymer film was identified with XRD and compared with bulk crystals. The configuration in the XRD measurement was such that only the crystal planes parallel to the polymer film surface was seen by the X-ray, thus the peak significantly more intense relative to the reference corresponds to the preferred nucleation face.

Figure 5:
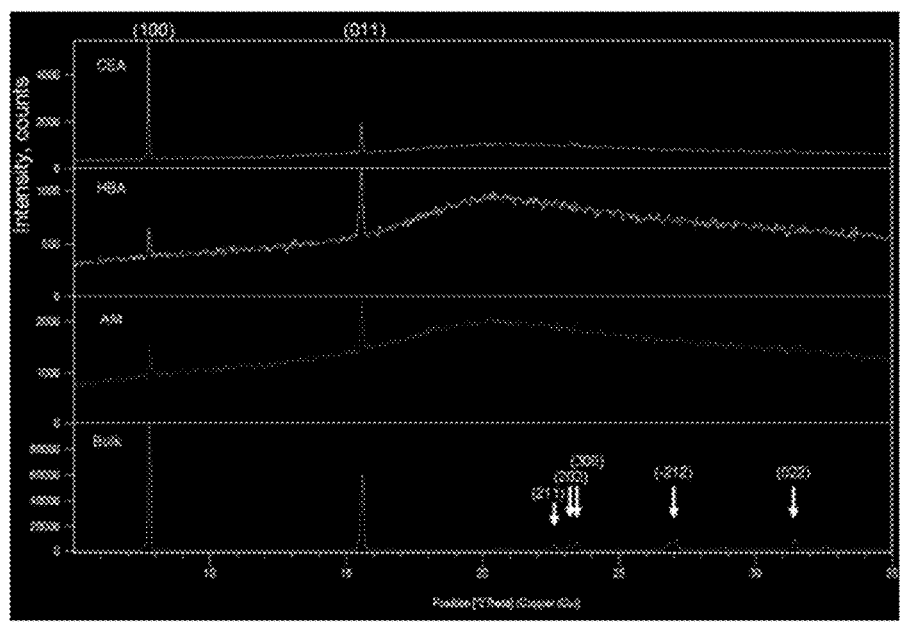
FIG. 5 shows X-ray diffraction patterns of aspirin crystals nucleated from polymer surfaces and from the bulk, according to some embodiments.

In a specific instance, the orientation of aspirin crystals on polymer films AM, CEA, and HBA was investigated. The representative XRD patterns are shown in FIG. 5. It is apparent from FIG. 5 that aspirin (011) face preferentially grows from polymer films HBA and AM, while (100) face on CEA. This result may be attributed, at least in part, to the underlying molecular interactions that steers the crystal orientation. The molecular structure of the corresponding crystal facet is shown in FIG. 18. The presence of carbonyl groups on aspirin (100) plane provides predominant hydrogen bond acceptors, and thus imparts slight Lewis basicity to the facet. Comparatively, the (011) plane is more acidic with the presence of undimerised carboxylic acid functional groups. Since CEA polymer surface mainly bares carboxyl groups, it is sensible for it to nucleate the (100) facet via hydrogen bonds with carbonyl groups. As for AM and HBA polymer surfaces which are rich in hydrogen-bond acceptors, they could preferentially nucleate the (011) facet through hydrogen bonds with carboxyl groups.

In FIG. 5: X-ray diffraction patterns of aspirin crystals nucleated from polymer surfaces and from the bulk. The (hkl) indices of the crystallographic planes are labeled over corresponding peaks. The broad peak around 20° C. seen in the top three diffraction patterns is attributed to the amorphous polymer film. Two primary peaks were observed in all the four patterns, one around 7.7°, and the other around 15.6°. Since the (011) peak is separated from the (002) peak by a 2θ angle of only 0.17 degree, the 2θ angle differences between the two primary peaks were carefully measured to determine that the peak around 15.6° matched with (011) plane. Current industrial practice to control nucleation from solution involves adjusting the nucleation temperature profile, supersaturation level, solvent to crystallize from, impeller designs, stirring speed, seeding, etc. However, the nucleation behavior remains largely unpredictable due to the presence of unregulated foreign surfaces present on impurities, the vessel wall or the impeller, because the foreign surfaces may possess the surface properties that happen to lower the nucleation energy barrier, etc. The methods described herein allows for the utilization of foreign surfaces with the surface chemistry and morphology designed to regulate the nucleation kinetics and crystal outcome.

Crystalline materials have been extensively studied for controlling crystallization on foreign surfaces. The epitaxy mechanism is well developed for nucleation on crystalline surfaces, such as self-assembled monolayers or SAMs, molecular single-crystal surfaces, crystalline polymer surfaces, etc. Compared with crystalline surfaces, amorphous surfaces such as crosslinked polymers as demonstrated in herein are easier, cheaper to fabricate, and the manufacturing protocol is already well established in the industrial practice. Furthermore, there is much greater flexibility to achieve complex morphologies with various surface chemistry, and there is no system compatibility issue with the crosslinked polymers, allowing the usage of virtually any solvent, unlike in the case of molecular crystals as the substrates.

This section focuses on the role of surfaces in crystallization from the perspective of nucleation kinetics, nucleation density, and crystal orientation in a quantitative manner, which is not reported before for small organic molecules. A method to systemically evaluate the nucleation activity of surfaces with various chemistry and morphology is demonstrated, which is a valuable tool to aid the design and selection of nucleation active surfaces.

Applications: The method described herein may be applied to designing interfaces or particles to regulate nucleation kinetics, to control the nucleation density and crystal orientation for pharmaceutical industry, food industry and other industries that require crystallization of small organic compounds.

1. Application in pharmaceutical manufacturing: Crystallization is extensively used to purify the active pharmaceutical ingredients in the pharmaceutical manufacturing process. After the crystallization step, the API crystals are generally granulated and blended with excipients in a series of solid state operations. The granulation and blending steps can be problematic. For example, they may be plagued by poor process controllability and final product uniformity, the process parameters may be sensitive to the properties of the drug crystals, etc. On the other hand, the properties of the drug crystals are constantly varying due to the difficulty in controlling crystallization.

The methods described herein allow for heterogeneous crystallization of API from solution on the surface of an amorphous excipient, so that the subsequent API compaction, granulation and blending with excipients can be ultimately eliminated or reduced. Furthermore, API nucleation kinetics and final crystal form have the potential to be tuned by designing the excipient surface properties.

2. Application in drug delivery: Recent years have seen great enthusiasm in making nanoscopic drug particles to improve the bioavailability of hydrophobic compounds and to release the drug in a controlled manner from a biocompatible nanoporous matrix. Generally, the drug particles are either broken down mechanically to reduce to desired sizes or are physically absorbed into nanoporous matrix in amorphous state. However, these methods are not ideal because the drugs are prone to phase transformation under mechanical stress or to recrystallize since the amorphous form is metastable. The methods described here allow for direct crystallization in the drug carrier and of making nanocrystals in nanoporous polymer matrix to enhance drug availability.

Example 2

The following example provides both prophetic and working examples of methods and systems of the present invention. This example describes exemplary methods and systems for the nanostructure and chemical makeup of polymer particles to control nucleation from solution. The methods and system may allow for the synthesis of unique composite particles comprised of crystalline active pharmaceutical ingredient and polymeric excipients.

As described above, in many areas of science and technology, such as the production of pharmaceuticals, semiconductors and optics, as well as the formation of biominerals, the ability to control crystallization is desired Synthesis of porous polymer particles with controlled porous microstructure: The polymer particles involved in this example are hydrogels. Hydrogels will be known to those of ordinary kill in the art and are generally defined by a chemically cross-linked network which swells in the presence of solvent such that the total volume fraction of polymer in the microstructure is much less than unity (e.g., typically less than 50%). Because mass transport and adsorption of chemical species within polymer hydrogels is important to their material function, in some embodiments, the porosity (pore structure) of hydrogels may be a critical aspect to their applications. Typically, porosity is categorized based on the length scale of the pore structure that controls various properties of the material. In this example, the term micropores refers to pores having characteristic dimensions less than 10 nanometers (e.g., 1-10 nm), which may influence the rate of diffusion of molecular species within the hydrogel interior. Similarly, the term mesopores refers to pores having dimensions from 10-1000 nanometers, and may primarily influence the overall surface area/volume ratio of the material, and control the diffusion of colloidal species within the microstructure. The term macropores refers to pores having dimensions from 1-100 microns may, which also may influence surface area/volume ratio, and may allow for flow and convective mass transport through the microstructure.

The polymer particles used in this example are chemically cross-linked hydrogels of poly(ethylene glycol) diacrylate with cube-like shape and dimensions of 30 μm×30 μm×23 μm prepared by Stop-Flow Lithography (SFL) (e.g., see FIG. 6a). The polymerizing fluid used was a composition of poly(ethylene glycol) diacrylate (PEG$_n$DA) as the monomer at various concentrations, 25 vol % PEG$_n$ as a molecular porogen (see below), and 5 vol % Darocur 1173 photoinitiator, with the remainder being ethanol. Upon irradiation with patterned UV light during SFL, the fluid undergoes free radical polymerization to produce a lithographically patterned cross-linked hydrogel microstructure.

Figure 6:
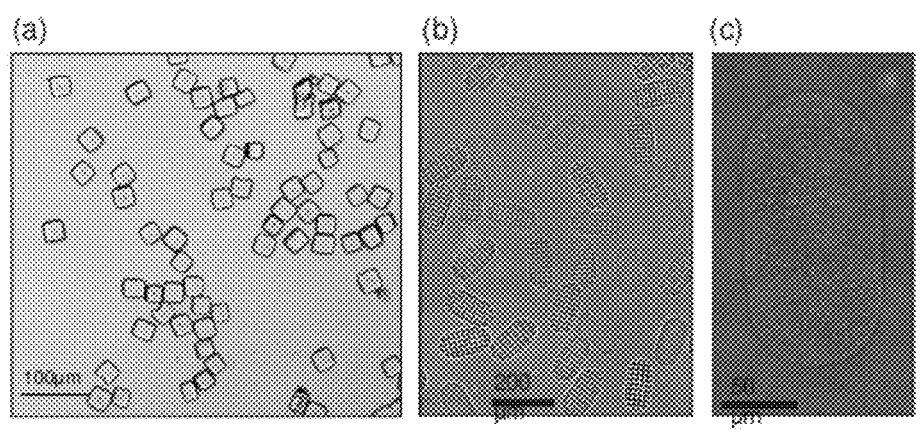
FIGS. 6a-6c show optical micrographs of hydrogel particles, according to some embodiments.

A primary aspect of this example involves development of a method by which these various levels of porosity may be independently controlled, and thus allowing for the synthesis of polymer hydrogel particles with widely tunable porous structure. Although methods currently exist to control one of these levels of porosity, no methods currently exist to control all three levels of porosity independently and at the same time. Previous methods use photolithography of a polymerizable fluid within a microfluidic device to create polymer microparticles and microstructures of well-defined shape (e.g., see FIG. 6). For example, FIG. 6a shows cube-like hydrogel microparticles created by SFL (see details below). In this example, SFL is also used to create lithographically patterned macroporous features within the particles. For example, FIG. 6b shows tablet-shaped microparticles of the same composition as those in FIG. 6a, but with regular arrays of square or circle-shaped holes of different size (e.g., down to about 2 microns) and density (e.g., up to 60% of the projected area of the particle).

In FIG. 6: Optical micrographs of hydrogel particles produced by the invented method: (a) cube-like particles with controlled microporous structure; (b) tablet-shaped particles with regular arrays of macroporous features and emulsion-templated mesopores; (c) tablet-shaped particles with emulsion-templated macropores with an average pore size of 0.8 micron (determined by image analysis).

Mesoporous structure may be controlled by addition of an inert, non-polymerizable templating agent to the polymerizing fluid, which can be removed upon completion of the polymerization to yield voids with similar size and shape of the templating agent. Emulsion droplets are frequently used as templating agents, as they are inexpensive, simple to prepare, and can be used to create large volume fractions of voids within the polymer microstructure. However, previous methods for incorporating emulsion droplets into a polymerizable fluid suffer two drawbacks. First, contemporary methods used to prepare the emulsion (e.g. mechanical mixing and ultrasonication) typically produce droplets in the range of 1-100 microns, which are inappropriate for templating of mesopores, and in the current method would interfere with macropore formation. Second, these methods typically produce droplets with significant polydispersity (CV>100%), which prevents the ability to precisely control the templated pore size.

Figure 7:
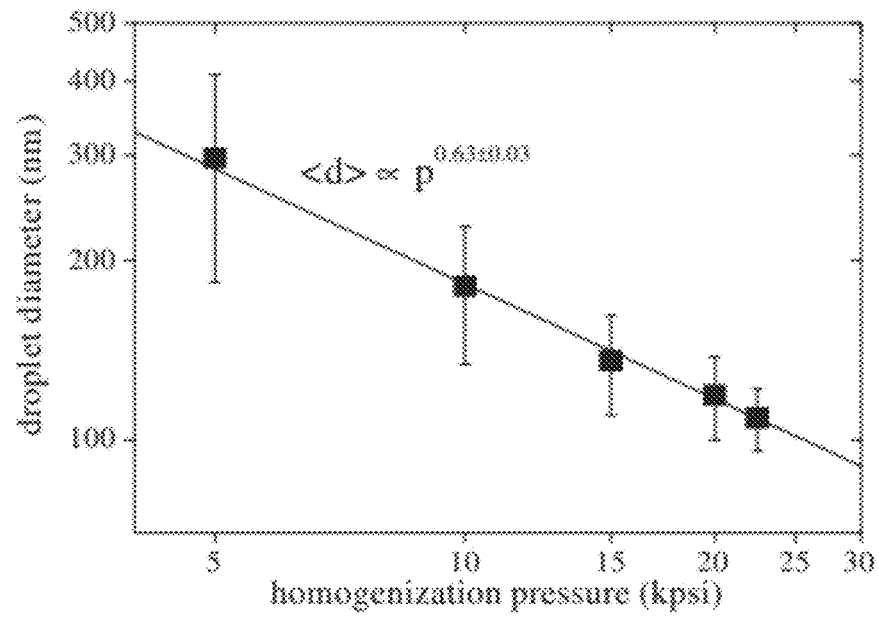
FIGS. 7 and 8 shows mesh sizes of hydrogel particles measured by equilibrium swelling measurements, according to some embodiments.

In the current method, high-pressure homogenization is used to produce "nanoemulsion" droplets characterized by low polydispersity and size appropriate for mesopores (e.g., less than 0.5 micron). FIG. 7 shows that high-pressure homogenization can be used to prepare nanoemulsions of inert silicone oil droplets suspended in a polymerizable fluid (e.g., as described herein) with controlled average drop size (in the range of 100-600 nm) and low polydispersity (CV<0.3). To demonstrate the use of emulsion-impregnated polymerizable fluids in the current method, FIG. 6b shows macroporous tablet-shaped particles polymerized in the presence of nanoemulsion droplets with an average diameter of about 110 nm at a volume fraction of 33%, demonstrating that the presence of the emulsion droplets does not significantly affect the ability to form macroporous features through lithographic patterning. Because the induced mesopores in FIG. 6b are not visible by bright field optical microscopy, FIG. 6c shows particles in which the emulsion droplets used to template pores have average size of about 570 nm and volume fraction of 33%, showing that the nanoemulsions can impart uniform pores within the particle interior.

In FIG. 7: Average size of nanoemulsions droplets (determined by dynamic light scattering) comprised of silicone oil with sodium dodecyl sulfate stabilizer produced by high-pressure homogenization versus applied homogenization pressure. Error bars represent coefficient of variation of the measured drop size distribution.

Figure 8:
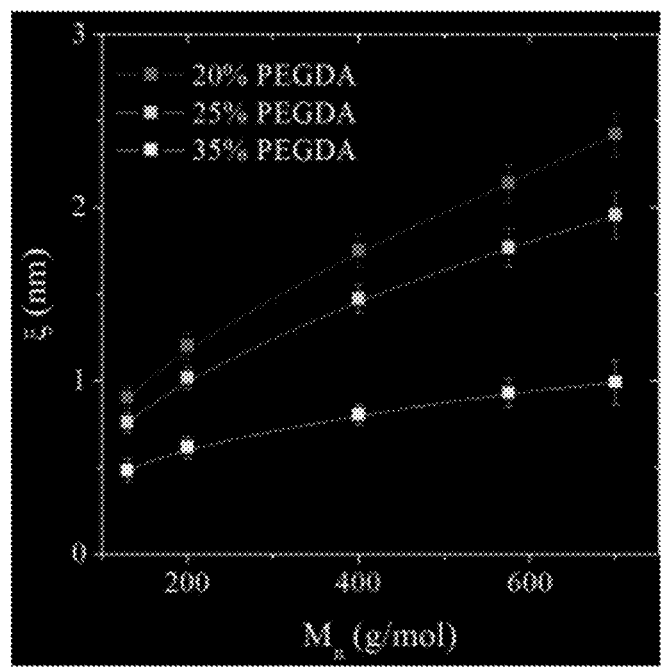

The porosity of cross-linked polymer hydrogels is typically characterized by the mesh size, which is related to the average polymer molecular weight between chemical cross-links. In the current method, this quantity may be controlled by adjusting the composition of the polymerizing fluid, including changes in the concentration and molecular weight of the monomer (e.g., in this case, $PEG_nDA$) as well as addition of porogens (e.g., in this case, PEW which can act as molecular pore-templating agents. To demonstrate this ability, FIG. 8 shows the estimated mesh size of hydrogel particles obtained from equilibrium swelling measurements for a series of $PEG_nDA$ molecular weight and concentration polymerized in the presence of $PEG_n$ with $M_n$ of 200 g/mol, yielding control of the mesh size in the range of 0.5-2.5 nm. Furthermore, when combined with other levels of porosity, the described method can produce polymer hydrogel particles with combined porosity of up to 95%, providing a large specific surface area while maintaining mechanical integrity of the particle.

In FIG. 7: Mesh size of PEGDA hydrogel particles suspended in 38/62 ethanol/water (v/v) measured by equilibrium swelling measurements as a function of $PEG_nDA$ concentration (% v/v) and molecular weight of the PEG chain ($M_n$) in the pre-polymer solution.

Controlling the nucleation kinetics by adjusting the polymer microporous structure: Surface morphology, especially porous structure, can play an important role in controlling nucleation kinetics and polymorphism in some embodiments. However, no study has been reported on controlling kinetics of nucleation from solution with polymers of tunable microstructure. Recent studies have shown mesoporous silica with 5-10 nm pores induced protein crystallization from aqueous solution. On the other hand, crystallization of benzyl alcohol and o-terphenyl from melt was suppressed in controlled pore glasses with 8.5 nm and 4 nm pores. A Monto Carlo simulation of nucleation in a square shaped open pore with 2D Ising model for one component system indicated the existence of an optimum pore size corresponding to a maximal nucleation rate. However, it has not been experimentally studied how the rate of nucleation from solution depends on the pore sizes. Moreover, the effect of pore chemistry on nucleation was largely neglected. Overall, mechanistic understanding is inadequate on nucleation from solution in nanoconfinement, which is a necessity for designing polymers with the proper microstructure and chemistry to control crystallization.

Figure 9:
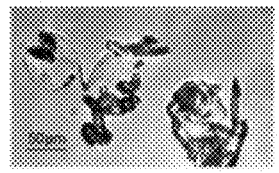
FIG. 9 shows an optical microscopy image of ASA crystals on $PEG_{700}DA$ particles, according to some embodiments.

The effect of nanoconfinement and pore chemistry on nucleation kinetics was investigated using a series of cube-like PEGDA hydrogel microparticles with $M_n$=130, 200, 400, 575, and 700 synthesized by the method described herein. The hydrogels are denoted with their corresponding $M_n$ of the monomers they are synthesized from for the rest of this example. In the crystallization solvent, the mesh sizes of these hydrogels range from 0.8 nm to 2.0 nm, as listed in Table 2. Aspirin (ASA) and acetaminophen (ACM) were used as model compounds for the crystallization studies. Crystallization of ASA or ACM from a 62/38 v/v water-ethanol mixture was induced by cooling, with or without PEGDA particles suspended in the solution by stirring. FIG. 9 shows an optical microscopy image of ASA crystals on $PEG_{700}DA$ particles as crystallized from 38 mg/ml ASA solution in 38/62 ethanol/water (v/v) with 15 μg/mL $PEG_{700}DA$ particles at 15° C., solution stirred at 700 rpm.

Nucleation kinetics of model compounds was investigated by measuring the nucleation induction time probability distribution. Nucleation induction time is generally time elapsed prior to the formation of a detectable amount of the new crystalline phase. It is a useful indicator of the surface nucleation activity because it can be dramatically shortened when the presence of an interface lowers the free energy barrier of nucleation. Due to the stochastic nature of nucleation events, a large number of experiments were performed to obtain the probability distribution of nucleation induction time. To obtain the average induction time $\tau$, statistical analysis on the induction time data was conducted based on the understanding that nucleation follows a Poisson distribution. According to Poisson statistics, the probability for a nucleation event to occur beyond time t is $P=\exp(-t/\tau)$, which implies that the fraction of vials without nucleation at time t exponentially decays as a function of time, where the scaling factor for time is the average induction time.

The statistical analysis of ASA nucleation induction time with or without PEGDA particles with a series of mesh sizes (denoted by $M_n$) suspended in a supersaturated aspirin solution was determined. The calculated average induction times are summarized in Table 2. Almost all PEGDA particles successfully promoted aspirin nucleation, except for $M_n=130$ g/mol. Specifically, the addition of particles with $M_n=400$ g/mol to the aspirin solution dramatically reduced the aspirin nucleation induction time to 60 minutes, while at the same experimental conditions, no nucleation event was detected in the absence of particle 400. Furthermore, the nucleation activity of the PEGDA particles decreased sharply by either increasing or decreasing the mesh size as indicated by the average induction times summarized in Table 2. This observation suggests that there exists an optimum mesh size for expediting nucleation from solution.

For determining the statistical analysis of aspirin nucleation induction time with PEGDA particles of various mesh sizes (particles denoted by $M_n$), 1.9 mL of 38 mg/ml ASA solution in 38/62 ethanol/water (v/v) with 15 µg/mL PEGDA particles was cooled at a rate of 5° C./min from 35° C. to 15° C. to achieve a supersaturation of 2.1. The solution was stirred at 700 rpm. The onset of nucleation was detected by an IR probe which measures the transmission signal through the solution. A total of 10 vials were cycled for 5-10 times to yield 50-100 nucleation induction time measurements for the statistical analysis.

Comparison of ASA nucleation rates in the presence of PEGDA particles of various mesh sizes at supersaturation of 2.1 and 3.3 were determined. The nucleation rate, J, is given by $J=1/\tau V$, where $\tau$ the average induction time (Table 1) and V the volume of solution. For this equation to be valid, the assumption is that the crystal growth rate is much faster than the nucleation rate, which is the case for ASA. At a supersaturation of 2.1, the crystallization temperature was 15° C., solution volume 1.9 mL; for a supersaturation of 3.3, the crystallization temperature was 8° C., solution volume 1.0 mL. Other crystallization conditions were kept the same.

Controlling nucleation kinetics by tuning the API-polymer interaction: Without wishing to be bound by theory, the success of the PEGDA particles in facilitating ASA nucleation may result from favorable interactions between aspirin and the PEGDA polymer matrix in the solution environment. This favorable interaction may have a positive impact on API nucleation in two ways. Firstly, may it lead to preferential partitioning of API into the PEGDA hydrogel interior relative to the bulk solution; hence, in the PEGDA phase, a higher API supersaturation may be achieved that favors nucleation. Secondly, it may reduce the free energy barrier associated with creating new interfaces during nucleus formation by replacing the nucleus-solvent interface with the nucleus-polymer interface, which may lower the free energy due to favorable interactions between the nucleus and the polymer.

This theory is exemplified by quantifying the partitioning of aspirin between the PEGDA gel phase and 38/62 ethanol/water (v/v), and determining the concentration of aspirin in the hydrogel particles. The partitioning experiments were performed at the same solution concentration and temperature as in the nucleation induction time experiments. In the partitioning experiment, both the concentrations of aspirin and ethanol were measured, as there are three species in the bulk solution, namely aspirin, ethanol and water, all of which partition in the gel phase to a certain degree determined by their relative interaction with the PEGDA polymer matrix. All the PEGDA particles concentrated aspirin for more than three times with respect to the bulk, while the ethanol concentrations remained comparable to that of the bulk. A slight increase in the aspirin concentration was observed as $M_n$ of the PEGDA particles increases from 130 g/mol to 700 g/mol. This phenomenon may be due, at least in part, to the fact that the crosslinking points and the subchain in the polymer matrix possess different chemical functionalities, hence they differ slightly in their degrees of interaction with aspirin and solvent molecules. Overall, the partitioning is consistently high for all the PEGDA particles and remained relatively insensitive to the variation in polymer mesh size. This result indicates that the interaction between aspirin molecules and the polymer matrix is favorable as compared to that between aspirin and solvent.

This theory was further exemplified in that the effectiveness of PEGDA particles in promoting API nucleation from solution was correlated with the interaction between the PEGDA and API. A second API compound which has weaker interactions with PEGDA was tested and the nucleation activity of the particles in this new system were assessed by performing nucleation induction time measurements. The study on a new API system also helps to demonstrate the generality of the existence of an optimum mesh size corresponding to the highest nucleation rate. The chosen API is acetaminophen (ACM), which was less concentrated in the PEGDA gel phase as compared to aspirin (FIG. 10), indicating a weaker interaction with the PEGDA polymer matrix.

Nucleation induction time measurements on the acetaminophen system) further attest to the overall success of PEGDA particles in facilitating nucleation. Table 1 shows that in most cases, the addition of particles in the acetaminophen solution led to a shorter average induction time compared with the bulk. This is not surprising given that acetaminophen partitions in PEGDA particles to approximately twice the bulk concentration (FIG. 10), thereby increasing the supersaturation leading to more favorable crystallization conditions for acetaminophen.

Furthermore, as in the aspirin system, an optimum pore size was also observed corresponding to the shortest nucleation induction time. However, unlike the aspirin system, the effect of PEGDA particles was not affected as dramatic in the case of acetaminophen as evidenced by the following observations. Firstly, the addition of PEGDA particles at best resulted in about ten-fold enhancement in the nucleation kinetics of acetaminophen, while in the case of aspirin, the degree of enhancement is by many orders of magnitudes (Table 2). Secondly, the particles were unable to induce acetaminophen nucleation at a supersaturation less than 3.7 within the experimental time frame, and at this supersaturation level, bulk nucleation started to occur at a detectable frequency, implying that the solution was fairly close to the upper bound of the metastable zone. As for aspirin, the PEGDA particles began to show effects at a much lower supersaturation (2.1). The fact that there was no detectable bulk nucleation at these conditions indicates that the solution was far from the boundary of the metastable zone, in these embodiments. These observations suggest that the PEGDA particles are less effective in inducing acetaminophen nucleation due to decreased partitioning compared with aspirin.

The results discussed above supported the theory that in addition to their nanostructures, the nucleation activity of the crosslinked polymeric particles also their interactions with the API. The mechanism of PEGDA particle-induced nucleation was partially explained by the higher API supersaturation inside the particles due to the effect of preferential partitioning of the API.

Composition of aspirin solution in the PEGDA gel phase were compared with the bulk phase. PEGDA gels sufficiently large for convenient handling were synthesized by UV polymerization, following the same formulation as the synthesis of PEGDA particles used in the crystallization study. The PEGDA gels were washed with ethanol and vacuum dried to remove unreacted species. The gel was then immersed in excessive 38 mg/ml aspirin solution in 38/62 ethanol/water (v/v) and allowed sufficient time to reach equilibrium swelling at 15° C. before taken out, pad dried, and put in excessive water. After 5 hours immersed in water, the concentrations of aspirin and ethanol in the aqueous phase were analyzed by UV-Vis spectroscopy and Gas Chromatography, respectively.

Figure 10:
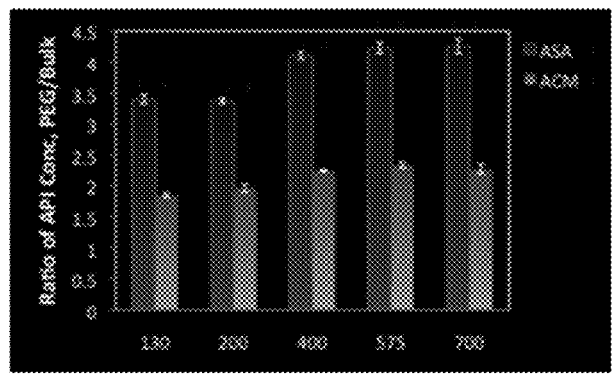
FIG. 10 shows partitioning of aspirin vs. acetaminophen in the PEGDA gel, according to some embodiments.

In FIG. 10: Partitioning of aspirin vs. acetaminophen in the PEGDA gel. Y axis represents the relative API concentration in the PEGDA, normalized by the bulk concentration. The aspirin partitioning experiment was conducted in 38 mg/ml aspirin solution in 38/62 ethanol/water (v/v) at 15° C. As for acetaminophen, 95 mg/ml acetaminophen solution in 38/62 ethanol/water (v/v) was used and the equilibration temperature was 8° C. In both cases, the experimental conditions were kept the same as used in the nucleation induction time study.

Statistical analysis of acetaminophen nucleation induction time with PEGDA particles was determined as follows: 1 ml 95 mg/ml aspirin solution in 38/62 ethanol/water (v/v) with 15 ug/ml PEGDA particles was cooled at a rate of 5° C./min from 35° C. to 8° C. to achieve a supersaturation of 3.7. The solution was stirred at 700 rpm. The onset of nucleation was detected by an IR probe which measures the transmission signal through the solution. A total of 10 vials were cycled for 5-10 times to yield 50-100 nucleation induction time data for the statistical analysis.

For the comparison of nucleation rates of aspirin and acetaminophen: Nucleation rate is in the number of nucleus per unit time per unit volume, as calculated from the average induction time by $J=1/\tau V$, where J is the nucleation rate, $\tau$ the average induction time, V the volume of solution. For this equation to be valid, the assumption is that the crystal growth rate is much faster than the nucleation rate, which is true for both aspirin and acetaminophen. The nucleation rate corresponds to supersaturation of 2.1 for aspirin, and 3.7 for acetaminophen.

Design principles for making API-excipient composite particles: Based on the fundamental understanding obtained from the above described methods and systems, general guidelines may be followed and design the chemistry and the structure of excipient and for selecting an appropriate solvent in order to maximize the likelihood for crystallizing a given API on/in the excipient.

To facilitate API nucleation on the excipient, the chemical makeup of the excipient and the solvent should be selected such that the API interacts stronger with the excipient than with solvent molecules (the interaction criterion). In the cases studied here, this was achieved by interactions between the polymer and API that led to equilibrium partitioning of API into the hydrogel particle phase relative to bulk solution. This yields increased supersaturation within the hydrogel interior, which is a significant driving force in classical theories of nucleation. Further tuning of the polymer chemistry to enhance this effect for a given API may be achieved by incorporating other chemical functional groups into the polymer network by co-polymerization of $PEG_nDA$ with other species capable of participating in the photopolymerization used to create the particles.

Figure 11:
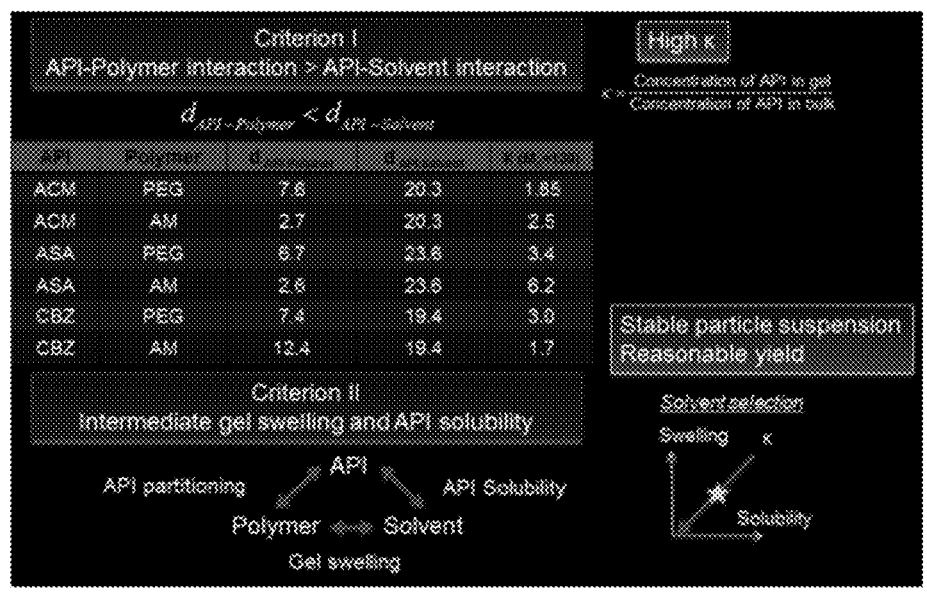
FIG. 11 shows Hansen parameters, according to some embodiments.

Shown in FIG. 11: Hansen parameters can aid the selection of the polymer chemistry that satisfy the interaction criterion. The distance 'd' in the Hansen parameter space provides a semi-quantitative measure for the extent of interaction. 'd' has been shown to be correlated with '$\kappa$', the partition coefficient of API in the polymer gel from solution, which serves to measure the interaction between API and the polymer. The interaction between the API and solvent is indicated from the API solubility, and that between the polymer and the solvent from gel swelling. According to the 'Interaction Criterion', it is desired to have API partitioning as high as possible, and API solubility and gel swelling as low as possible. However, practically speaking, a stable microgel suspension is needed

TABLE 2

Comparison of the average nucleation induction times ($\tau$) for API crystallization with PEGDA microparticles of various mesh sizes. The aspirin (ASA) crystallization was performed at two supersaturation levels (S), 2.1 and 3.3. The acetaminophen (ACM) crystallization was conducted at the supersaturation of 3.7. The PEGDA particle mesh sizes were calculated from the swelling ratio in 38/62 ethanol/water (v/v) based on the Flory-Rehner theory for swollen cross-linked gels. The standard errors of average induction times were calculated from the standard error values for the slopes regressed from the lnP vs. t plots (FIG. 6) following the formula $lnP = -t/\tau$.

| PEGDA $M_n$ (g/mol) | Bulk (no particles) | 130 | 200 | 400 | 575 | 700 |
|---|---|---|---|---|---|---|
| Mesh size (nm) | N/A | 0.8 ± 0.1 | 1.0 ± 0.1 | 1.5 ± 0.1 | 1.8 ± 0.1 | 2.0 ± 0.1 |
| ASA $\tau$ (min) S = 2.1 | ∞ | ∞ | 910 ± 40 | 63 ± 3 | 1900 ± 100 | 6600 ± 1100 |
| ASA $\tau$ (min) S = 3.3 | 2500 ± 600 | 330 ± 60 | 52 ± 3 | 123 ± 7 | NA | 240 ± 20 |
| ACM $\tau$ (min) S = 3.7 | 6500 ± 1600 | 920 ± 70 | 540 ± 20 | 1720 ± 150 | NA | 6500 ± 1600 | as well as a reasonable API crystal yield, which require high degree of gel swelling and high API solubility. To balance the two requirements, the second criterion for selecting appropriate polymer chemistry is to have intermediate gel swelling and API solubility.

Furthermore, the rate of crystallization was found to vary by orders of magnitude depending on the mesh size of the cross-linked polymer network within the particle. This suggests that the particle microstructure can be rationally tuned for a specific API in embodiments where the critical nucleus size is known, and can act as a screening tool for favorable nucleation conditions if it is not known. Additionally, the mesh size can be controlled by a number of factors in the particle synthesis method, including the concentration and molecular weight of both monomer and molecular porogen species, as well as the conversion of the polymerization reaction. Thus, the mesh size can be controlled over a very wide range while at the same time providing flexibility to changes in other properties of the excipient particles.

Current industrial practice to control nucleation from solution involves adjusting the nucleation temperature profile, supersaturation level, crystallization solvent, impeller designs, stirring speed, seeding with existing API crystals, etc. However, the nucleation behavior remains largely unpredictable due to the presence of unregulated foreign surfaces present on impurities, the vessel wall or the impeller, because the foreign surfaces may possess characteristics that happen to lower the nucleation energy barrier. The methods and systems described herein enable utilization of excipient particles with surface chemistry and morphology designed specifically to directly control the nucleation kinetics and crystal outcome.

Crosslinked polymers and functionalized glass have been used to control the polymorphs of pharmaceutically related small molecular compound. However, the methods described herein use the role of surfaces in crystallization from the perspective of nucleation kinetics, nucleation density and crystal orientation in a quantitative manner, which is not reported before for small organic molecules. Furthermore, methods to systemically evaluate the nucleation activity of surfaces with various chemistry and morphology were provided, which is a valuable tool to aid the design and selection of nucleation active surfaces.

Crystalline materials have been extensively studied for controlling crystallization on foreign surfaces. The epitaxy mechanism is well developed for nucleation on crystalline surfaces, such as self-assembled monolayers (SAMs), molecular single-crystal surfaces, crystalline polymer surfaces, etc. A primary disadvantage of crystallization on these materials is that the resulting crystals are immobilized to a surface, and generally are broken if they are to be used in further process steps. This effects the crystal size distribution, which may be detrimental to the eventual formulation of the substance. Because the methods/systems described herein use suspendable particles as the excipient surface, the particles can easily be flowed through devices and further process components while maintaining the mechanical integrity of the particle and API crystals.

Furthermore, compared with crystalline surfaces, amorphous surfaces such as the cross-linker polymers demonstrated here are easier and cheaper to fabricate. The synthesis method described herein for polymer excipients is also much more flexible toward excipients with complex morphologies and different surface chemistries. Because the polymers particles are cross-linked, they can be used with virtually any solvent, unlike the case of molecular crystal excipients, for which the solvent should be carefully chosen so that neither excipient nor API is soluble under the crystallization conditions.

Finally, the ability of the polymer hydrogel excipients to absorb and concentrate API due to equilibrium partitioning within the interior of the particles is a novel and unique ability. In other methods, the production of a commensurate increase in supersaturation is either by adding more API to solution, which may not be possible if the substance is scarce, or by changing the solvent in or temperature at which the crystallization is performed, which may result in incompatibilities with subsequent process steps.

In this example, the optimum mesh size for inducing ASA nucleation was found to be approximately 15 Å, and the diameter of ASA molecules about 6 Å (estimated from the crystal density). Without wishing to be bound by theory, the optimum mesh size may allow for aspirin molecules associated with polymer chains to come within sufficient proximity to form a nucleus, given the proper orientation (as would also be the case with ACM). However, as the mesh size becomes smaller, a solute 'sees' more polymer chains than other solute molecules, which may prevent the formation of large enough solute clusters; for larger mesh sizes, the solutes associated with the polymer chain are further separated from each other, hence the solute-solute interaction may not be enhanced. Therefore, in some embodiment, the ability to control nucleation by nanoconfinement may lie in manipulating the effective solute-solute interaction, which can be strongly affected by polymer-solute interactions and the spatial confinement imposed by the polymer microstructure, the interplay of which can give rise to the observed optimum mesh size for expediting nucleation.

Accordingly, a series of experiments were performed in which the ASA crystallization temperature was lowered from 15° C. to 8° C., thereby increasing the supersaturation from 2.1 to 3.4. Since this change in supersaturation is significant whilst the absolute temperature was only altered by 2%, this experiment primarily probes the effect of increased supersaturation, which may enhance effective solute-solute interactions due to increased density fluctuations. As a result, the observed optimum mesh size decreased from 15 Å to 10 Å at the higher supersaturation level (Table 2). Accordingly, in this experiment, fewer solute molecules were needed to overcome the nucleation barrier, which was lowered due to higher density fluctuations.

Example 3

It is well recognized that surfaces may play an important role in liquid-solid phase transformations, and surface morphology has been shown to impact nucleation and crystallization. However, current fundamental understanding is insufficient to allow the rational design of surfaces for nucleation/crystallization control. It is generally accepted that surface roughness helps promote nucleation, although little is known of the role that cavity shape of the rough surface plays in the nucleation process. This example shows that the shape of surface nanopores (e.g., which are described in the specification as features or wells) can affect the nucleation behavior. Contrary to common belief, a rough surface may inhibit nucleation of a molecular crystal from solution depending on surface morphology. The role played by surface chemistry in nanopore-induced nucleation, in some embodiments, is demonstrated in this example. Direction regarding surface-induced crystallization is provided, which may be applied to many areas of science and technology from designing 'seed' particles for regulating crystallization of various fine chemicals, to controlling pharmaceutical polymorphism, to orient biominerals on organic substrates, to promote protein nucleation for structure determination, and/or to inhibit ice nucleation on airplanes.

Crystallization from solution generally initiates from a solid-liquid interface, and "bulk" nucleation is generally thought to occur on microscopic surface in the liquid phase, However, various surface properties impact nucleation have not been well understood, particularly at the microscopic level. It is widely accepted and presented in the literature that roughening of the surface present in the crystallization system leads to accelerated nucleation, and in industrial practice, surface scratching has long been used to promote nucleation. However, without knowledge of the topological features of the surface cavities at a microscopic scale relevant to nucleation, the surface roughness alone, as a macroscopic parameter, may be insufficient, and even misleading, to describe the effect of surface morphology on nucleation. Recently, there has been an increase in the number of studies on crystal nucleation in sub-100 nm pores, which were demonstrated to affect nucleation kinetics, polymorphism, and/or crystal orientation. These studies focused mainly on the effect of pore size in the context of nanoscopic confinement, but the role of pore shape was not studied.

This example demonstrates that nanopore shape can play a key role in determining the kinetics of nucleation from solution. The importance of favorable surface chemistry, in some embodiments, in mediating the observed 'pore shape effect' is also demonstrated.

In this example, the effects of angular pores are compared to those of spherical pores of similar size. For this purpose, a fabrication technique was required to control both the feature geometry and the pore size down to length scales relevant to nucleation, i.e., to enable surface patterning with pores from a few to hundreds of nanometers. Nanoscopic pores with high area density may be preferred, providing a sufficient number of pores to ensure statistical significance of the observed effects on nucleation. Sub-10 nm pores were avoided in this example because, in some cases, reported volume confinement effects on nucleation may mask the effects of pore shape. In addition, the resolution requirement for the fabrication technique was set by the length scale of molecular events preceding nucleation, namely the molecular clustering and re-orientation that occur in domains of, probably, a few nanometers for small organic molecules. To meet these requirements, a 'Nanoparticle Imprint Lithography' (NpIL) technology was developed, which was used to fabricate nanopatterned polymer surfaces with nanopore arrays of various shapes ranging from ten to hundreds of nanometers, using nanoparticle assemblies as templates.

Figure 12:
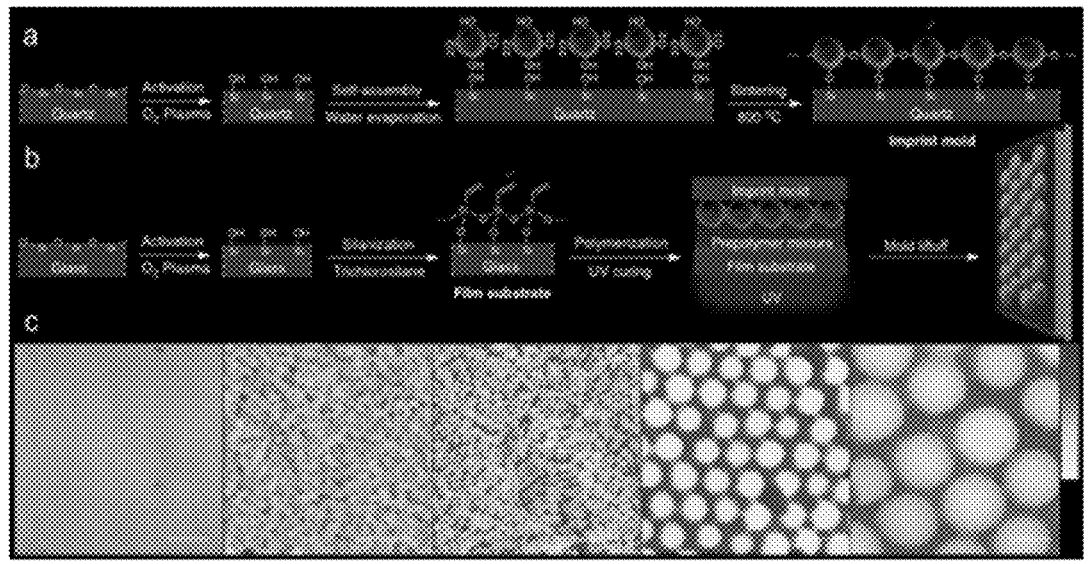
FIGS. 12a and 12b illustrate fabrication methods for polymer films using spherical wells on the surface of a substrate by nanoparticle imprint lithography (NpIL).
FIG. 12c shows AFM images of polyacrylic acid films crosslinked with divinylbenzene (AA-co-DVB) with and without spherical wells, accordingly to some embodiments.

The fabrication of polymer films with spherical nanopores by NpIL is illustrated in FIG. 12. First, spherical silica nanoparticles were self-assembled on a quartz slide driven by capillary forces during water evaporation, and then anchored to the substrate via calcination to form the imprint mold (FIG. 12a). Second, a mixture of monomer, crosslinker and initiator was sandwiched between the imprint mold and the substrate, and subsequently polymerized under UV irradiation. The imprint mold was then easily peeled off to reveal a polymer film conforming to the substrate, with the nanopattern inversely transferred from the imprint mold (FIG. 12b). Polymer films with spherical nanopores ranging from 15 nm to 300 nm were fabricated in this manner (FIG. 12c), templated by commercially available monodispersed colloidal silica of various sizes. This method combines many of the advantages of NSL and ultraviolet-assisted NIL, such as low cost, high throughput, and high-resolution. Moreover, in contrast to the commonly practiced NSL technique, where hydrofluoric acid is needed to dissolve the silica nanoparticles, the above-described method removes the template nondestructively by a simple liftoff from the polymer film, allowing the mask to be recovered easily and reused.

In FIG. 12: Fabrication of polymer films with spherical nanopores by NpIL; (a) Template preparation via colloidal silica self-assembly and its anchoring to the quartz substrate; (b) Film substrate preparation and polymer film synthesis by UV polymerization; (c) AFM height images of polyacrylic acid films crosslinked with divinylbenzene (AA-co-DVB) with and without spherical nanopores templated with colloidal silica of various sizes. The average pore size is (from left to right) none, 15 nm, 40 nm, 120 nm, and 300 nm. The scale bar is 200 nm. The data scale in height is (from left to right) 50 nm, 50 nm, 50 nm, 100 nm, and 400 nm.

Polymer films with hexagonal pores (FIG. 13a) were also prepared by NpIL following a similar procedure, templated with iron oxide magnetic nanocrystals with well-defined facets (FIG. 13b). Nanopores of various other shapes can be achieved by NpIL. In an alternative approach, a top-down fabrication of square nanoposts on a silicon wafer was explored (FIG. 13d) by Achromatic Interference Lithography (AIL) for templating square nanopores (FIG. 13c). AIL offers efficient patterning over a large area with sharply delineated features (minimum radius of curvature <5 nm). The resulting square pores in the polymer film are comparable to the spherical ones in width and depth (FIG. 13e), which enables unambiguous differentiation of the effects of pore shape on crystal nucleation.

In FIG. 13: Angular nanopores on AA-co-DVB polymer films and their templates; (a) AFM height image of hexagonal nanopores on the polymer surface templated with iron oxide magnetic nanocrystals via NpIL. The scale bar is 50 nm. (Inset) Higher resolution image of a hexagonal nanopore. The scale bar is 10 nm (b) TEM image of iron oxide magnetic nanocrystals as synthesized. The scale bar is 50 nm; (c) AFM height image of square nanopores on the polymer surface templated with Si square posts. The scale bar is 200 nm; (d) High resolution SEM image of Si square posts on Si wafer fabricated by AIL for templating square pores. The scale bar is 200 nm. (e) Depth profiles of square and spherical nanopores of similar sizes. The scale bar is 200 nm. The square pores are 125 nm in width, 48 nm in depth, and the spherical pores are 120 nm wide, 45 nm deep on average.

The effect of nanopatterned polymer films on the kinetics of nucleation from solution was quantified by measuring the nucleation induction time of aspirin, a representative small organic molecule. The polymer film was made from acrylic acid crosslinked with divinylbenzene (AA-co-DVB), with which aspirin could interact via hydrogen bonding. Polymer crosslinking was designed to avoid solvent uptake and to maintain the surface morphology when in contact with the solution. Due to the stochastic nature of nucleation events, 20 to 50 samples were tested simultaneously to obtain the probability distribution for the nucleation induction time. The average induction time, $\tau$, was determined from a statistical analysis on the induction time data assuming that nucleation follows a Poisson distribution, $P(t)=\exp(-t/\tau)$. The nucleation rate, J, was calculated from $\tau$ via $J=1/\tau V$, where V is the volume of solution, with the assumption that the time scale of nucleation is much longer than that of crystal growth, valid for this system.

Figure 14:
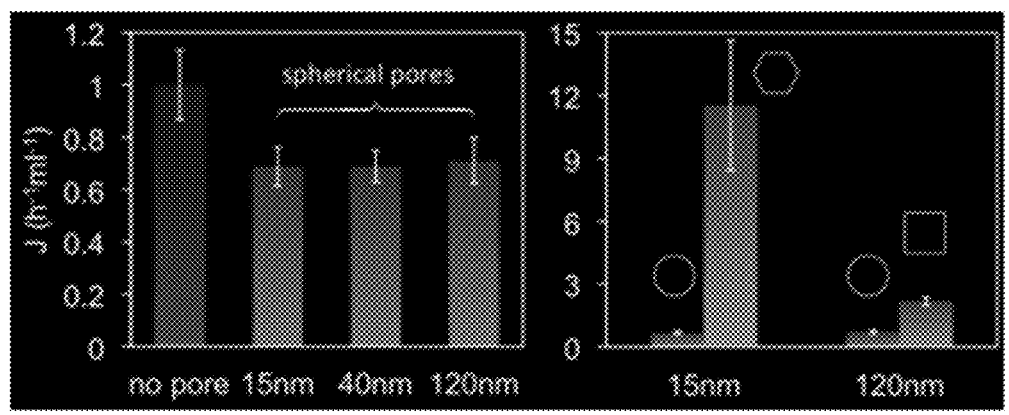
FIG. 14 illustrates the effect of the feature shape in AA-co-DVB polymer films on the nucleation kinetics of aspirin, according to some embodiments.

In FIG. 14: Effect of the nanopore shape in AA-co-DVB polymer films on the nucleation kinetics of aspirin: flat vs. spherical pores (left); spherical pores vs. hexagonal pores and square pores of the same size (right). J is the nucleation rate, in number of nuclei per ml of solution per hour, calculated from the average nucleation induction time τ by J=1/τV, where V is the volume of solution. The standard errors of J were calculated from the regression on the induction time probability distribution following the Poisson distribution.

As shown in FIG. 14, increasing the surface roughness by modifying the nonporous film with spherical nanopores surprisingly inhibited nucleation. The size of the spherical nanopores appeared to have little effect on the nucleation kinetics, within the range tested, but nucleation was promoted when angular pores of the same size were used, as shown in two cases. With hexagonal pores, the polymer film enhanced aspirin nucleation rates by more than an order of magnitude relative to those observed with spherical pores, while in the case of square pores, a three-fold enhancement was observed. These results indicate that the ledges and/or corners that distinguish angular from spherical pores acted as nucleation sites, in this embodiment, which was verified via Atomic Force Microscopy (AFM) and X-ray Diffraction (XRD), as discussed later.

These observations may be interpreted in terms of recent computational results. Simulations have shown that freezing of optimum wedge angle corresponds to an intrinsic angle within the crystal, formed by two close-packed planes, at which the crystal can grow defect-free along both sides of the wedge. This scenario can be considered as a case of angle-directed epitaxy, where an angle characteristic of the topological feature on the substrate directs the crystal nucleation in a minimum-stress configuration, exhibited as a geometrical match between the substrate and the crystal.

Angle-directed epitaxy is a possible mechanism in this case because the aspirin crystal possesses intrinsic angles formed by close-packed, low-index facets close to the characteristic angles in the nanopores tested (FIGS. 15c, 15d, and 15f). In the square nanopore, the ledge at the intersection of the pore wall and the pore floor ($L_{wf}$, its dihedral angle abbreviated as α) could induce the growth of either (011) and (100), or (002) and (100) facets of aspirin ((011)∧(100) or (002)∧(100), with dihedral angles abbreviated as $\theta_{011}\wedge_{100}$ and $\theta_{002}\wedge_{100}$, respectively) (FIGS. 15c and 15d), where (100), (011) and (002) are the three major facets of aspirin crystallized from bulk solution. To estimate the extent of angular epitaxy, the cross-section of the square nanopore was examined via High Resolution Scanning Electron Microscopy (HRSEM), and α was measured to be 96±7° C. in one corner of the cross-section and 101±5° C. in the other. This asymmetry was consistent through the cross-section, which may have arisen from the asymmetric stress applied to the polymer film during the template liftoff. Both $\theta_{011}\wedge_{100}$ and $\theta_{002}\wedge_{100}$ fall in the vicinity of the smaller α, 96±7°, with $\theta_{002}\wedge 100$ being the closer match ($\theta_{002}\wedge_{100}$=95.84°, $\theta_{002}\wedge_{100}$=92.94°). Specifically, about 30% of pores contained an angle α of within 1° C. of $\theta_{002}\wedge_{100}$, and around 8% within 1° C. of $\theta_{002}\wedge_{100}$. If angle-directed epitaxy were the only factor dictating nanopore-induced nucleation, (002)∧(100) would be nucleated from the ledge within the pore. The AFM images of aspirin crystals grown from the pores suggest it was the (011)∧(100) facets that emanated from the ledge, whereas the (002) facet was not in contact with the pore surface (FIGS. 15a and 15b). A layered growth mode is evident in both the crystal grown out from the pore (FIG. 15a) and the crystals contained in the pore (FIG. 15b), which originates from the aspirin dimerization via the carboxyl group within the layer, and a much weaker Van de Waals interaction between the layers. FIG. 15b shows that these crystal layers seem to extend from the pore wall with which the (011) face is in contact. Moreover, the layer extension direction is consistent in all pores containing crystals, indicating nucleation occurs predominantly from one side of the pore. In addition, only a fraction of the pores induced nucleation. These observations provide evidence that the (011)∧(100) and not (002)∧(100) facets were nucleated from $L_{wf}$, but may be from those ledges with the appropriate angle α. These growth patterns can be attributed to the favorable interactions between (011)∧(100) and the polymer surface, as inferred from the characteristic functionalities displayed on their respective surfaces (FIGS. 15c and 15e). (011) and (100), rich in carboxyl and carbonyl groups, can form hydrogen bonds with the carboxyl groups on the AA-co-DVB polymer surface, whereas the nonpolar (002) plane may interact with the polymer much more weakly. This result suggests that solute-polymer interactions can play an important role in determining nucleation behavior in angular pores, in addition to angle-directed epitaxy.

Figure 15:
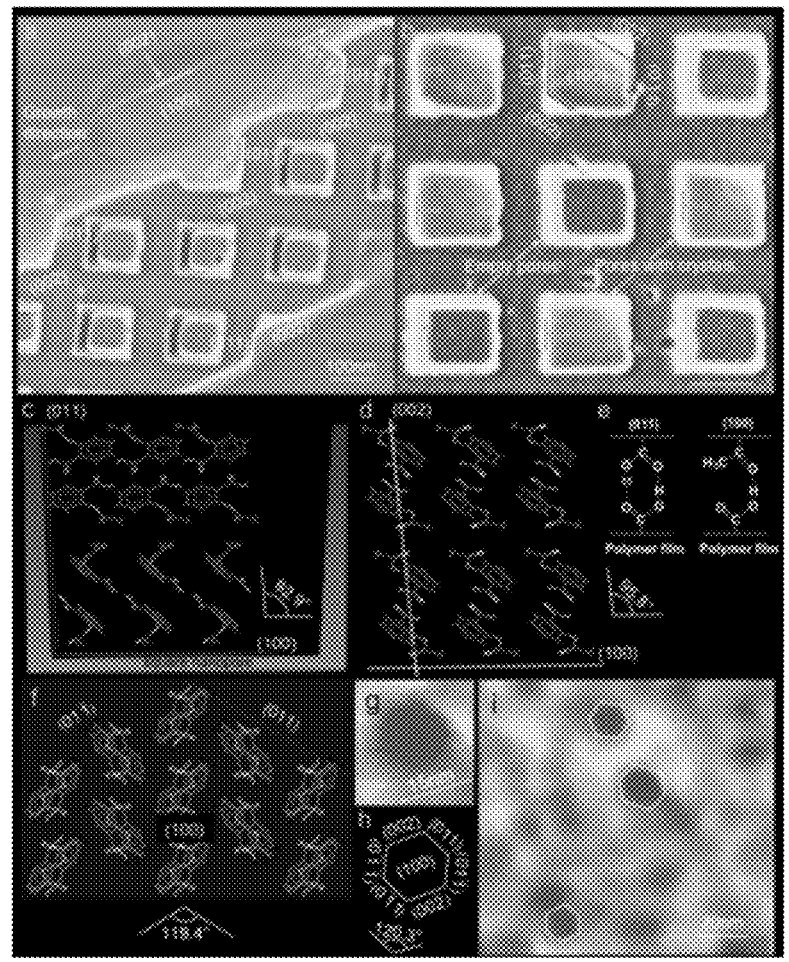
FIG. 15a shows an AFM phase image of aspirin crystals grown in square wells on the surface of a substrate, according to some embodiments.
FIG. 15b shows an AFM phase image showing (100) layers of aspirin crystals nucleated at ledges in the square wells on the surface of a substrate, according to some embodiments.
FIGS. 15c-15d illustrate representative epitaxy configurations of aspirin crystal facets along the ledge of a square wells on the surface of a substrate, according to some embodiments.
FIG. 15e shows proposed aspirin-polymer interactions at a crystal-polymer interface, according to some embodiments.
FIG. 15f shows a proposed epitaxy configuration of aspirin crystal facets at the corner of hexagonal wells on the surface of a substrate, according to some embodiments.
FIGS. 15g-15h show AFM phase images of an aspirin crystallite grown from hexagonal wells on the surface of a substrate and possible orientations, according to some embodiments.
FIG. 15i shows an AFM height image of the surface of an aspirin crystal grown on and detached from an AA-co-DVB polymer film having hexagonal wells on the surface of a substrate, according to some embodiments.

In FIG. 15: Angle-directed epitaxy of aspirin crystals induced by angular nanopores; (a) AFM phase image of aspirin crystals grown out from the square pores; (b) AFM phase image showing (100) layers of aspirin crystals nucleated at ledges in the square pores. The scale bar is 100 nm; (c, d) Representative epitaxy configurations of aspirin crystal facets along the ledge of the square pore; (e) Proposed aspirin-polymer interactions at the crystal-polymer interface; (f) Proposed epitaxy configuration of aspirin crystal facets at the corner of an hexagonal pore; (g, h) AFM phase image of an aspirin crystallite grown from the 15 nm hexagonal pores and its possible orientation; (i) AFM height image of the surface of an aspirin crystal grown on and detached from the AA-co-DVB polymer film with hexagonal pores.

Following the principles of angle-directed epitaxy assisted by favorable interactions of the crystal facets with the substrates, the corners within hexagonal pores may act as nucleation sites to induce the growth of (011)∧(01$\bar{1}$)∧(100) with (100) in contact with the pore floor, and (011)∧(01$\bar{1}$) with the pore walls (FIG. 15f). This may be because the angle mismatch is very small in this configuration, and all three faces of aspirin could interact with the polymer surface via hydrogen bonding. If nucleation ensued from the corner, the growth thereafter may have resulted in an aspirin crystallite that fit comfortably inside the pore and took on the shape of a hexagon, given that other intrinsic angles of the crystal also matched quite well with the pore geometry (FIG. 15h). Indeed, crystallites with comparable shape and size to those of the pore were observed via AFM on the surface of aspirin crystals detached from the polymer film (FIGS. 15g and 15i). In addition, XRD results verified that the (100) face was in contact with the pore floor. These observations support corner-induced nucleation from hexagonal pores in this embodiment.

Figure 16:
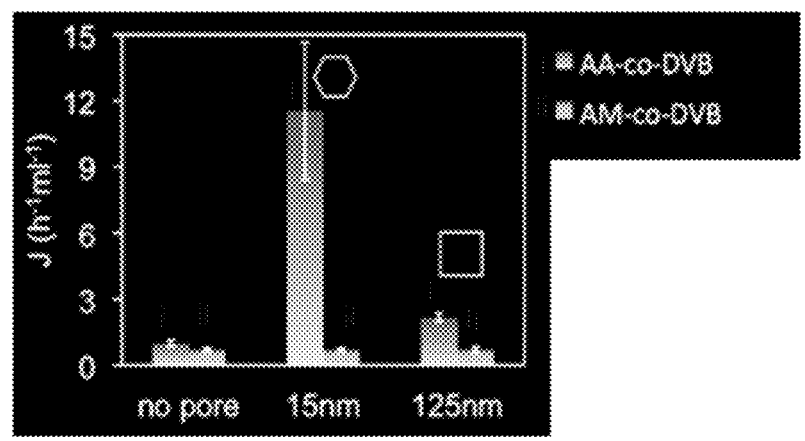
FIG. 16 illustrates the effect of polymer surface chemistry on the kinetics of angular features-induced nucleation of aspirin, according to some embodiments.

Based on the experimental and computational evidence, a molecular mechanism to interpret the pore shape effect on nucleation is now described. Crystal nucleation from solution is preceded by molecular cluster formation via density fluctuations and molecular re-orientation through structure fluctuations; both may be required for nucleation. The rate of nucleation can be modified in two ways by the presence of an amorphous, nanoporous surface in a metastable solution. First, favorable surface-solute interactions can enrich solute concentrations near the surface, facilitating molecular cluster formation. Second, ledges/corners in the pore can induce partial orientational order of the solute in domains close to the surface via specific interactions and geometrical confinement, which enhances the solute molecular realignment. When the molecular orientation imposed by the ledge/corner geometry resembles that in the crystal, the rate of nucleation is increased to the greatest extent, the macroscopic expression of which is angle-directed epitaxy. This can also implies that for angular nanopores to promote nucleation, favorable surface-solute interaction may be required, in some embodiments. To verify this point, the chemical makeup of the polymer film was altered from AA-co-DVB to AM-co-DVB (FIG. 16). This chemistry was selected out of the polymer films tested because, in the absence of pores, it exhibited no effect on aspirin nucleation from butyl acetate, indicating that surface-solute interactions are not sufficiently strong to affect nucleation under these conditions. Patterning of the AM-co-DVB surface with the same angular nanopores did not lead to enhanced nucleation kinetics relative to nucleation on non-porous films (FIG. 16).

In FIG. 16: Effect of polymer surface chemistry on kinetics of angular nanopore-induced nucleation of aspirin: AA-co-DVB vs. AM-co-DVB. J is the nucleation rate, in number of nuclei per ml of solution per hour. AM denotes 4-acryloyl-morpholine. AA denotes acrylic acid. AM-co-DVB refers to poly 4-acryloylmorpholine crosslinked with divinylbenzene.

In summary, nanopore shape can play a key role in determining the kinetics of surface-induced nucleation probed with a small organic model compound. Angular pores of chosen geometry and surface chemistry promoted nucleation, while spherical pores of the same size did not in this example. Ledges in the square pores and corners in the hexagonal pores were active nucleation sites, following the principle of angle-directed epitaxy. The pore geometry and specific surface-solute interactions may jointly determine which crystal facets would nucleate preferentially. Favorable surface-solute interactions may be required for angular pores to promote nucleation. A molecular mechanism may be present by which the pore shape affects nucleation by altering the molecular orientational order near the ledges/corners of the pores.

Methods

Fabrication of polymer films with spherical nanopores: Quartz slides (75 mm×25 mm) were treated with $O_2$ plasma to enrich the surface in hydroxyl groups. Two hundred microliters of 5 w % colloidal silica (commercially available) were spread on the quartz slide and allowed to self-assemble during slow water evaporation over 12 hours. The self-assembled $SiO_2$ and the quartz slide were then sintered at 800° C. for 5 min to coalesce the particles with the quartz slide and form the imprint mold. The film substrate (25 mm×5 mm) was prepared by treating a glass slide with $O_2$ plasma followed by silanization with trichlorosilane in a vacuum oven at 40° C. Silanization is necessary to adhere the polymer film to the substrate and avoid film cracking and peeling. One microliter prepolymer mixture of monomer acrylic acid (AA), crosslinker divinylbenzene (DVB), and initiator IRGACURE 2022 were sandwiched between the imprint mold and the film substrate. The molar ratio of monomer to DVB was 2:1. The concentration of IRGACURE 2022 was 4 v % with respect to DVB. The prepolymer mixture was then polymerized under UV irradiation for 15 min, at 72 mW/cm$^2$. After irradiation, the imprint mold was peeled off and the polymer films were annealed at 70° C. in a vacuum oven for 3 h to remove unreacted species. Parts were generally pre-cleaned and assembled in a Bio-safety cabinet to reduce contamination by impurities, which may interfere with polymer film induced nucleation.

Fabrication of polymer films with angular nanopores: Polymer films with hexagonal nanopores were synthesized following a procedure similar to that described above, templated with iron oxide magnetic nanoparticles (MNP). The presence of sufficient surfactants (oleic acid) during synthesis was important to obtain sharply defined facets of MNP crystals. As in the case of making spherical nanopores, colloidal self-assembly was utilized for preparing the imprint mold, which was made by spreading 20 µl MNP-decane solution (~9 w %) on a plasma cleaned quartz slide (75 mm×25 mm) and allowing the decane to evaporate over a period of 6 hours. The excessive surfactants present in the nanocrystal dispersion also participated in the assembly process leaving space for polymers to form between the nanocrystals. After polymerization, the imprint mold was peeled off from the polymer film, the nanocrystals on the film were subsequently dissolved with dilute hydrocholoric acid (~1 N), and the film was rinsed with deionized water followed by acetone and vacuum drying. The imprint mold for making square pores was fabricated by Achromatic Interference Lithography at the MIT Research Laboratory of Electronics. The mold took the form of 120 nm Si square pillar arrays with 200 nm pitches covering a 3-inch Si wafer. The top edges of the pillars were sharply defined with radii of curvature less than 5 nm. Large area patterning is necessary for making sufficient copies of polymer films to obtain the induction time probability distribution. The polymer film synthesis and post-processing procedures were the same as those used in the preparation of spherical nanopores. The effects of polymer films with pores on nucleation kinetics were compared against those in the absence of pores, which were synthesized following the same procedure with the quartz surface as with the template.

Nucleation Induction Time Measurement: Once synthesized, the polymer film with its substrate was inserted vertically into a 1 ml glass shell vial containing 200 µl 47 mg/ml aspirin solution in butyl acetate. For each polymer sample, 20-50 vials were assembled and immersed in a circulator stabilized at 50±0.1° C. to dissolve any pre-existing crystals, and then the solution was quench cooled to 5±0.1° C. by immersing into a second circulator. The number of vials in which crystallization occurred was recorded as a function of time. All the operations involving exposing polymer films, aspirin solutions and shell vials to the atmosphere were conducted inside a Bio Safety Cabinet to reduce impurity contamination to the lowest level. Efforts were made to clean all components before usage and aspirin solutions were filtered with an Acrodisc 0.2 µm PTFE syringe filter.

Characterization: Atomic Force Microscopy (AFM) and Powder X-ray Diffraction (XRD) were employed to study the aspirin crystal orientation inside the angular nanopores on the polymer films after the nucleation induction time study. AFM images were obtained with a Dimension 3100 XY closed loop scanner (Nanoscope IV, VEECO) equipped with NanoMan software. Height and phase images were obtained in tapping mode in ambient air with silicon tips (VEECO). The crystal orientation was verified with XRD to identify the specific crystallographic planes parallel to the polymer film. The X-ray diffraction patterns were recorded with a PANalytical X'Pert PRO Theta/Theta Powder X-Ray Diffraction System with Cu tube and X'Celerator high-speed detector. No less than five polymer films were examined with XRD on each type of polymer sample.

Synthesis of faceted $Fe_3O_4$ nanoparticles: Materials: Iron tri(acetylacetonate) (Fe(acac)$_3$) (97%), 1,2-tetradecanediol (90%), oleic acid (OA) (90%), and benzyl ether (99%) were purchased from Sigma Aldrich. n-Decane (99%) was purchased from Alfa Aesar. Methanol (99.8%) was purchased from Mellinkrod. All chemicals were used as received. All water utilized in the experiments was Milli-Q (Millipore) deionized water. Synthesis method: Colloidal dispersions of faceted $Fe_3O_4$ nanoparticles were prepared by a slightly modified procedure of these method for the synthesis of spherical $Fe_3O_4$ nanoparticles reported previously (e.g., see Harada, T.; Hatton, T. A. *Langmuir* 2009, 25, 6407). In brief, iron tri(acetylacetonate) (2 mmol), 1,2-tetradecanediol (10 mmol), oleic acid (12 mmol), and benzyl ether (20 mL) were mixed and stirred magnetically under flowing nitrogen. The mixture was heated gradually to 200° C. and kept at this temperature for 2 h. Then, the temperature was increased up to the reflux condition (300° C.) under a blanket of nitrogen, and kept for 1 h at reflux. The black reacted liquid was cooled to room temperature by air-cooling and transferred from the reaction flask to a centrifugation bottle. On addition of methanol (40 mL) to the reaction mixture, the black nanoparticles precipitated and were separated via centrifugation (9000 rpm, 10 min). To remove the residual reacting materials, the precipitated nanoparticles were rinsed with methanol several times. After the precipitated nanoparticles were well-dried, 10 mL of n-decane was added to the precipitate and the mixtures were ultrasonicated.

Nucleation induction time study to select polymer chemistry: In this study, polymers with smooth surfaces were synthesized directly in the glass shell vials used for crystallization, instead of on a glass substrate as in the case of polymer films with nanopores. In this way, the impurities and active nucleation sites from the glass substrates were substantially eliminated.

30 μl prepolymer mixture of monomer, crosslinker divinylbenzene (DVB), initiator IRGACURE 2022 were injected into the 1 ml pre-cleaned glass shell vials under the Bio-Safety Cabinet. The monomers tested were 4-acryloylmorpholine (AM), 4-Hydroxybutyl acrylate (HBA), and acrylic acid (AA). The molar ratio of monomer to DVB was 2:1. The concentration of IRGACURE 2022 was 4 v % with respect to DVB. The prepolymer mixture was subsequently polymerized under UV inadiation under $N_2$ protection for 30 min, at ~10 $mW/cm^2$. Less UV intensity and longer inadiation time were applied to avoid polymer cracking after synthesis. After polymerization, the polymers and the shell vials were allowed to slowly cooled down for 30 min before annealed at 70° C. in a vacuum oven for 5 h to remove unreacted species.

The nucleation induction time study followed the same procedure as stated in the methods section. In some cases, the bottom of the vials were attached ⅜-inch thick rubbers to block heat transfer from the bottom of the vials. This may be necessary in some cases because the polymers conformed to the bottom of the vials differ in heat conductivity, resulting in different cooling rate in the solution if the heat transfer were allowed through the bottom of the vial, and the cooling rate significantly impacts the nucleation induction time. In addition, enough vial spacing was designed to allow equivalent cooling rate around each vial.

Supplementary Results and Discussion

Figure 17:
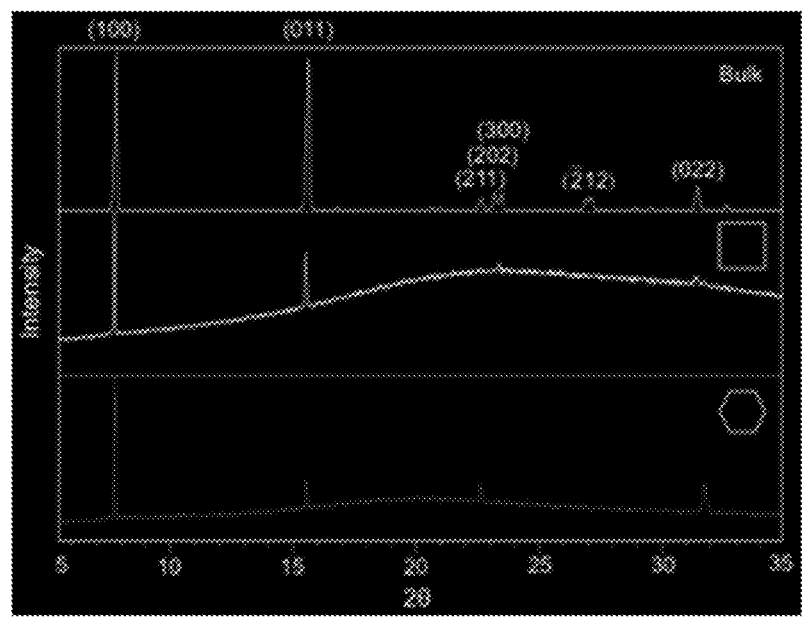
FIG. 17 shows X-ray diffraction patterns of aspirin crystals grown from a butyl acetate bulk solution (top), on substrates having square wells on the surface of a substrate (middle), and hexagonal wells on the surface of a substrate (bottom), according to some embodiments.

Crystal orientation by XRD: In FIG. 17: X-ray diffraction pattern of aspirin crystals grew from the butyl acetate bulk solution (top), on AA-co-DVB films with 125 nm square nanopores (middle), and on AA-co-DVB films with 15 nm hexagonal nanopores (bottom).

In this embodiment, as shown in FIG. 17, (100) facet of aspirin was identified as the preferred orientation on AA-co-DVB films with angular pores, relative to the random orientation of bulk crystals. This result indicates that (100) facets grew parallel to the polymer surface, which is in line with the observation by AFM (FIG. 15) and the inference from angle-directed epitaxy and favorable polymer-solute interactions. The XRD pattern in the case of square pores also suggests that a fraction of crystals grew with (011) facet parallel to the polymer surface. It is made possible when aspirin nucleates from ledge inside the pore with (011) facet in contact with the pore floor and (100) with the pore wall, which also satisfies the rules of angle-directed epitaxy assisted with favorable polymer-solute interactions.

Assignment of aspirin crystal facets: The crystal facets in the AFM images (FIG. 15) were assigned based on the following observations. First, a layered growth mode is evident from both the overgrown crystal (FIG. 15a) and the crystals contained in the pore (FIG. 15b), which originates from the aspirin dimerization via the carboxyl group within the layer, and a much weaker Van de Waals interaction between the layers. It is these layers that constitute the aspirin (100) plane, which was confirmed by XRD that the (100) plane grew parallel to the film surface (FIG. 17). Second, the terrace formed by the edges of developing layers points towards the crystal growth direction (FIG. 15a), which is along the (010) axis, and the slow growing face (002) is left to define the crystal edges. This assignment is in agreement with the dihedral angles exhibited by the crystals in the pore (FIGS. 15a and 15b).

Nucleation inhibition by spherical nanopores: Monte Carlo simulation have shown that freezing of hard sphere colloids are frustrated on curved surfaces, on which crystals cannot grow free of stress, and the resulting defects increased the nucleation barrier to nucleation. Concave surfaces with radius of curvature ($R_S$) from 10 to 150 times the diameter of the colloids (σ), which overlaps with the range that was investigated ($R_S$=12.5, 33, 100σ; σ, the size of aspirin, is 6 Å estimated from the crystal density were previously investigated). However, this trend was generally not observed, suggesting in this study that the nucleation on a curved surface becomes increasingly difficult on a more strongly curved surface. It may be due, at least in part, to the practical limitations in the experiment. Particularly, it is very hard to eliminate unintended nucleation sites from the system, either on the film substrate or residue dust particles, which could trigger nucleation and prevent measurement of the real extent of nucleation inhibition by the spherical pores. It is evidenced by the observation that crystals mostly precipitated from elsewhere in the system, rather than grew out from the film with spherical pores. Attempts were made to avoid and remove as much impurities as possible from the system and to silence the nucleation sites on the film substrate by coating or functionalizing with inert moieties, but the average nucleation induction time could not be further lengthened. Nonetheless, the observation is largely in line with the implication from the computational study, and the inhibition effect by the spherical pores is most likely greater than experimentally observed. In contrast to simulations, the inhibition effect of nanopatterned surfaces was measured against imperfect flat surfaces in practice. Thus the nucleation inhibition could also be attributed to the elimination of active nucleation sites from the flat surface by replacing them with inactive spherical nanopores.

Comparison of polymer chemistry effect on aspirin nucleation: In FIG. 18: Role of surface chemistry in nanopore-induced nucleation; Statistical analysis of aspirin nucleation induction times with and without nonporous polymers. The linear regression follows the formula ln(P)=−t/τ to obtain the average induction time τ. P is the probability for no crystallization event to occur within time t. The standard error of τ was obtained from linear regression of the slope.

FIG. 18 illustrates the polymer chemistry effect on aspirin nucleation. Compared with the bulk, polyacrylic acid crosslinked with DVB (AA-co-DVB) showed marked effect on aspirin nucleation kinetics, yielding an average induction time consistent with that observed with nonporous AA-co-DVB films on glass substrate (FIG. 14 left). In contrast, HBA-co-DVB slightly affected nucleation, and AM-co-DVB virtually no effect. Thus, AM-co-DVB was chosen as a negative control to demonstrate the effect of polymer chemistry on the angular-nanopore-induced nucleation (FIG. 16). The observed average nucleation induction times with polymer films on the glass substrate (FIG. 16) were much shorter than that measured with polymer surfaces without substrates because of the interference from the active nucleation sites on the substrate and the impurities brought in by the substrates, aforementioned.

The effect of surface chemistry on nucleation kinetics could result from a competition between the solute-polymer interaction and the solute-solvent interaction. Specifically, for aspirin molecules to nucleate on the polymer surface, aspirin needs enrich near the polymer surface driven by specific solute-polymer interactions, however, such interaction is shield by the solvent-solute interactions to certain extent. In the case of AM-co-DVB, the carbonyl group of solvent butyl acetate could complete with that of the polymer to interact with the carboxyl group of aspirin via hydrogen bonding, imposing strong shielding effect; as for AA-co-DVB, it can form carboxylic dimers with aspirin molecules, with which the strength of butyl acetate-aspirin interaction might not complete with.

Comments on the nucleation activities of hexagonal pores vs. square pores: The observed difference in nucleation activities of hexagonal pores vs. square pores may arise from several factors. First, the polymer films with hexagonal pores have higher pore area density (Table 3), which may have contributed to its higher nucleation activity. However, the area density of pores is not equivalent to the area density of active nucleation sites. Specifically, corners in the hexagonal pores are most likely to be the nucleation sites, whereas in the case of square pores, ledges are identified to be responsible for induction aspirin nucleation. One-dimensional nucleation sites (corners) cannot be directly compared with two-dimensional ones (ledges) in terms of the area density. Second, aspirin grows from the corners in hexagonal pores with three facets in contact with the pore wall, which is likely to be more energetically favorable compared with nucleation from ledges where two out of these three facets are in contact with the ledge planes. To further the investigation, nanopores of various geometries with the same size will be fabricated and molecular dynamic simulation is being performed to gain insight.

TABLE 3

Nucleation induction time of aspirin induced by AA-co-DVB films patterned with angular nanopores.

| Pore shape | Hexagonal | Square |
|---|---|---|
| Pore size | 15 nm | 125 nm |
| τ (min) | 26 ± 7 | 138 ± 12 |
| # of pores/μm$^2$ | 700 | 25 |
| # of corners/μm$^2$ | 4200 | 100 |

Example 4

This Example described the role of polymer-solute interactions in gel-induced nucleation.

INTRODUCTION: Interfaces present in a metastable liquid are believed to have a profound impact on nucleation behavior. Considerable strides have been made over the last few decades towards understanding the effect of interfaces on nucleation and several mechanisms have been proposed. The epitaxy mechanism has been established to describe crystal formation on crystalline surfaces or surfaces with two-dimensional symmetry. Surfaces may also affect nucleation via polarization matching with the crystallizing molecule when both the surface and the crystal exhibit net dipole across the surface/crystal interface. These mechanistic understanding should provide guidance for designing surfaces to control crystal nucleation. However, the applicability of these approaches is restricted to a large extent, because the surface properties involved may not be adjustable catering to the system of interest, and one may be limited to surfaces with 3D or 2D symmetry, such as crystal facets, self-assembled monolayers, and Langmuir-Blodgett films, etc. Non-crystalline polymeric materials offer a promising alternative, whose structure, topology and chemistry are easily tunable over a wide range by a variety of established fabrication methods. Particularly, polymer gels with tunable microstructures can aid in controlling nucleation kinetics. Polymer gels are unique in their ability to concentrate solute molecules via thermodynamic partitioning driven by favorable polymer-solute interactions, and intermolecular interactions may aid in promoting nucleation.

Intermolecular interactions have been demonstrated to play an important role in dictating the nucleation behavior at interfaces. However, mechanistic understanding is still insufficient to enable rational design of surface chemistry for controlling nucleation of molecular crystals from solution. The complexity partially arises from weak intermolecular interactions in molecular systems relative to ionic, metallic, and/or covalent crystals, flexible molecular conformations, and/or intricate solvent effects. In practice, the influence of intermolecular interactions on nucleation is often convoluted with other factors such as surface lattice structures, surface morphology, etc., making it more challenging to study.

This example helps to elucidate the role of intermolecular interactions in gel-induced nucleation and its interplay with the effect of polymer microstructures on nucleation. Chemically modified polymer microgels via copolymerization were synthesized and were studied and were studied its effect on nucleation kinetics as compared to unmodified microgels. Nucleation kinetics of model compounds was very sensitive to the polymer-solute interactions, and dramatic acceleration of nucleation was observed when the strength of polymer-solute interactions was increased markedly. The functionalized microgels left signatures on nucleation induction time distribution, in some embodiments, featuring two characteristic time scales, which may suggest chemical heterogeneity at nanometer scale due to copolymerization. The underlying mechanism from the perspective of adsorptive partitioning and templating effect was explored to interpret the role of intermolecular interactions in gel-induced nucleation.

Results and Discussion

Synthesis of the polymer microgels: Two model polymer chemistries were chosen for synthesis of microgel particles to use in gel-induced nucleation studies. The first were crosslinked homopolymer gels of poly(ethylene glycol) diacrylate (PEG$_M$DA) of various monomer molecular weight, M (g/mol). The second were co-polymers of PEGDA and 4-acryloylmorpholine (AM). AM was selected as a co-monomer to functionalize the PEGDA gel because it contains multiple hydrogen-bond acceptors, which may interact favorably with the hydrogen-bond donors of aspirin (ASA) and acetaminophen (ACM), the model compounds employed in this example.

Synthesis of model microgel PEGDA and PEGDA-co-AM microgels was carried out using Stop Flow Lithography as described in herein. Cube-shaped microgels were prepared to facilitate imagining such that the orientation of surface-attached crystals was unambiguous.

PEGDA microgels were prepared from a range of monomers with M=130-700 g/mol using pre-cursor fluids containing a fixed concentration of PEGDA of 25 vol %. Similarly, PEGDA-co-AM microgels were prepared using the same range of monomer molecular weights containing 15 vol % PEGDA and 15 vol % AM. The range of PEGDA molecular weights thus represents a range of crosslinking density across the different microgel particles, resulting in a range of the average mesh size, $\xi$, of the crosslinked gel; i.e., the average distance between crosslinks within the polymer network. The particular pre-cursor concentrations of PEGDA and AM used were chosen to closely match $\xi$ between the two systems in order to isolate the effect of polymer chemistry on nucleation kinetics.

Characterization of polymer microstructure: The microstructure of PEGDA and PEGDA-co-AM gels was characterized in order to better elucidate the nature of polymer-API interactions and their effect on nucleation. Estimates of $\xi$ were obtained from equilibrium swelling measurements using a procedure described previously. FIG. 19 compares the apparent mesh size from swelling measurements (closed symbols) obtained previously measured for PEGDA microgels (i) to that obtained for PEGDA-co-AM microgels (ii) with increasing M. The incorporation of AM into the PEGDA hydrogel network resulted in a mild increase in mesh size on the order of 10-25% over the range of PEGDA molecular weights studied. This is expected, since the effective lengthening of the acrylic polymer backbone by insertion of AM monomers is small compared to the overall length of PEG chains.

In FIG. 19: Mesh size of PEGDA (i) and PEGDA-co-AM (ii) hydrogels measured in 38/62 (v/v) ethanol/water at 23° C. using estimated by equilibrium swelling measurements (closed symbols) and SANS analysis (open symbols).

In order to examine the microstructure of the PEGDA and PEGDA-co-AM gels in further detail, as well as to validate several assumptions made in the equilibrium swelling measurements, small angle neutron scattering (SANS) measurements were performed on representative hydrogel samples with M=200 g/mol and 700 g/mol. The corresponding absolute intensity spectra, $I(q)-I_{bk}$ are shown in FIG. 20, where the incoherent background intensity, $I_{bk}$, has been subtracted. The data were fit to a generalization of the Debye-Bueche model:

$$I(q) = \frac{A}{1+(\xi q)^m} + \frac{B}{[1+(\Xi q)^n]^2} + I_{bk}. \quad (1)$$

The first term is used to describe local fluctuations of individual chains with excluded volume constrained by crosslinks, whose length scale is set by the mesh size, $\xi$. The scaling exponent m is related to the solvent quality of the polymer chains; e.g., m=2 for Gaussian chains, whereas m<2 for chains in a good solvent. The second term describes the low-q structure, and arises from large-scale heterogeneity (either static or dynamic) within the material, where $\Xi$ is the characteristic length scale of structural inhomogeneity. The scaling exponent n is related to the nature of the interface between inhomogeneous regions of the material. It is typically assumed that n=2, corresponding to sharp interfaces between inhomogeneities. This restrictive assumption generally resulted in poor fits to the SANS data collected for both PEGDA and PEGDA-co-AM microgels. Therefore, the Debye-Bueche model were generalized by leaving n as an adjustable parameter. This is empirically equivalent to assuming that the density profile between homogeneities can be described by scattering with a surface fractal dimension of $n^2$; i.e., $n^2=4$ for a sharp interface, whereas $3<n^2<4$ for a diffuse interface.

In FIG. 20: Absolute SANS intensity spectra for the polymer hydrogels indicated. Solid lines give best fits to the Debye-Bueche model Eq. (1).

TABLE 4

Structural properties of PEGDA and PEGDA-co-AM hydrogels from SANS analysis.

| Polymer | $M_n$(g/mol) | $\xi$ (nm) | m | $\Xi$ (nm) | n |
|---|---|---|---|---|---|
| PEGDA | 200 | 0.92 ± 0.06 | 1.88 | 23.3 ± 1.4 | 1.88 |
|  | 700 | 2.09 ± 0.08 | 1.59 | 53.6 ± 1.4 | 2.16 |
| PEGDA-co-AM | 200 | 1.05 ± 0.06 | 1.38 | 10.4 ± 1.6 | 1.80 |
|  | 700 | 2.39 ± 0.08 | 1.34 | 61.6 ± 1.2 | 2.04 |

Eq. (1) was fit to the experimental data, and the best-fit model predictions are shown in FIG. 20, with the corresponding model parameters are listed in Table 4. The generalized Debye-Bueche model gave a quantitatively accurate description of the data. Thus, the microstructure of both PEGDA and PEGDA-co-AM microgels exhibited significant structural heterogeneity over length scales ranging from 10-60 nm. The length scale for heterogeneity, given by $\Xi$, ranges from 10-20$\xi$ for the PEG$_{200}$DA polymers, and decreases upon addition of the AM co-monomer. By contrast, $\Xi$ is approximately equal for both the PEG$_{700}$DA homopolymer and its AM co-polymer, with a value that of $\Xi$~25$\xi$. Furthermore, the Porod exponent n~2 for the PEG$_{700}$DA gels suggest sharp interfaces between structural inhomogeneities, whereas n~1.8-1.9 for the PEG$_{200}$DA samples suggests a transition to more diffuse interfaces at low PEGDA molecular weight.

Although the nature of this heterogeneity is unknown, such structure typically arises from microphase separation within the hydrogel, where the structure exhibits distinct regions of different density. For the PEGDA and PEGDA-co-AM gels studied here, the phase separation could either be between the polymer and solvent, between the various constituent moieties of the polymer (ethylene glycol, acrylate, and AM), or a combination of both phenomena. For example, previous studies have shown that formation of PEGDA hydrogels in the presence of high molecular weight PEG porogens leads to polymer phase separation and the formation of micron-scale pores within the hydrogel. However, optical imaging of the microgel particles considered here exhibited no evidence of such large-scale porosity. Turning to the SANS results, note that both and n are found to primarily depend on the PEGDA monomer molecular weight, and not the presence of AM co-monomer. Since the primary chemical difference between the PEG$_{200}$DA and PEG$_{700}$DA monomers is the relative amount of acrylic groups compared to ethylene glycol units, therefore the structural heterogeneity within the hydrogels may be driven by microphase separation of the polymerized acrylic groups.

Figure 21:
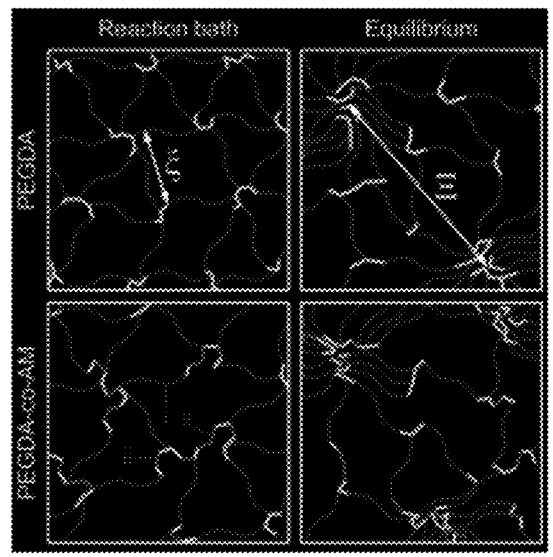
FIG. 21 shows schematics of microgel structures inferred from SANS measurements, according to some embodiments.

In FIG. 21: Schematics of microgel structures inferred from SANS measurements. Long light grey chains (e.g., i), short black chains, and short dark grey chains (e.g., ii) denote the PEG subchain, acrylate and AM segments, respectively.

FIG. 21 shows diagrams of possible structures for the PEGDA (top) and PEGDA-co-AM (bottom) hydrogels under such a scenario. In the so-called reaction bath in which the crosslinked network is formed (left), the nascent hydrogel exhibits homogeneous microstructure. At equilibrium (right), however, phase separation of the acrylic backbone chains leads to phase separation, where acrylate-rich regions coexist with acrylate-poor regions. This depiction of the microstructure is consistent with the observed trends in SANS data, as follows. Since the poly(ethylene glycol) strands of the gel is attached at the ends by acrylic groups, the length scale Ξ will be primarily determined by the length of PEG chains (blue) between neighboring acrylic backbone chains (red). This explains the observed trend in Ξ, which increases for 3-5 fold as the PEGDA molecular weight is increased from 200 g/mol to 700 g/mol. Since the addition of AM co-monomer (green) within the gel generally occur along the acrylic backbone chains, the AM groups will thus primarily be contained within the AM-rich regions. This explains the fact that neither Ξ nor n change significantly upon co-polymerization with AM, since the AM groups does not significantly affect the structure of the AM-poor regions.

Regarding the smaller length scale structure of the gels, given by the mesh size ξ and free volume exponent m, given the previous discussion, the definition of a uniform average mesh size, such as that obtained from swelling measurements, is insufficiently describe the microstructure of the microgels. The measured values of ξ from the SANS measurements are generally in fair quantitative agreement with those measured by equilibrium swelling measurements (FIG. 19). It is reasonable to presume that averaging of the mesh size over various polymer-rich and polymer-lean regions within the gel may result in an average mesh size that is similar to that measured in a macroscopically-averaged measurement such as swelling.

In contrast to the large-scale heterogeneous structure, m depended significantly on the presence of AM co-monomers within the hydrogel. For the PEGDA homopolymer gels, m~1.6-1.8, indicating that the polymer exhibits behavior characteristic of flexible chains in a good solvent, as expected for PEG in aqueous solution. By contrast, m~1.3-1.4 for the PEGDA-co-AM co-polymer gels. This value of m is significantly outside the range of 5/3<m<2 expected for flexible chains in a good solvent, and in the range of 1<m<1.5 expected for semi-flexible chains. Although the source of such behavior is unclear, one possible explanation is a change in stiffness of the acrylic backbone chains upon co-polymerization of the bulky AM co-monomers, resulting in an overall decrease in flexibility of the polymer at length scales less than the mesh size.

Quantification of polymer-solute interactions: The strength of intermolecular interactions between the PEGDA-co-AM polymer network and the molecule to crystallize was characterized with the solute equilibrium partition coefficient at the same condition as used in the crystallization study. Solute partition coefficient κ, defined as the ratio of solute mass fraction in solution confined in the gel to that in the bulk, is a relevant parameter because it informs the solute concentration in the gel at the crystallization condition, which is an important factor affecting nucleation. Shown in FIG. 22, κ of ASA increased by 60% on average after introducing AM into the PEGDA gel, and the ASA concentration in the PEGDA-co-AM gels reached as high as six times as that in the bulk solution. This result indicates much stronger interactions between ASA and the polymer matrix after functionalization. Before chemical modification, κ climbed from 3.4 to around 4.2 with the increase of $M_n$, the PEG molecular weight of the PEGDA monomer, while after modification, κ became insensitive to M. This observation suggests that ASA mainly interacted with AM segments of PEGDA-co-AM polymer in the solution environment, for reasons discussed as following.

The PEGDA polymers are comprised of the PEG subchain and the acrylate crosslinkers. As $M_n$ increases, the mass ratio of PEG to acrylate increases, so does κ in the case of PEGDA system, indicating that ASA primarily associates with the PEG subchain. This inference is further supported by the fact that the molar ratio of ethylene oxide units in PEG to ASA remained constant (7.7) for all mesh sizes, calculated from the partition experiments. In the case of PEGDA-co-AM, the mass fraction of AM doesn't change with $M_n$, and correspondingly, κ also turned invariant yielding a constant AM to ASA molar ratio of around unity. This result provides evidence that ASA preferred to interact with AM than with PEG or acrylate groups constituting the polymer gel.

Figure 23:
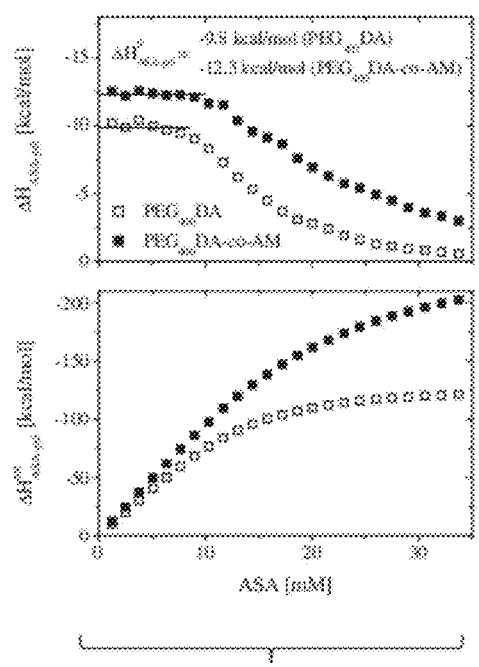
FIG. 23 shows enthalpy isotherms for adsorption of ASA onto hydrogels, including instantaneous (top) and cumulative (bottom) enthalpies of adsorption, according to some embodiments.

The ASA-polymer interactions were further quantified with the solute adsorption enthalpy via Isothermal Titration calorimetry (ITC), which also helps to deepen the understanding of partitioning effect. FIG. 23 shows the results of ITC measurements, where the enthalpy of interaction between ASA and both $PEG_{400}DA$ and $PEG_{400}DA$-co-AM microgels is plotted versus the equilibrium concentration of ASA. The data are presented both as instantaneous enthalpies at a given concentration, $\Delta H_{ASA-gel}$ (top), and as cumulative enthalpies up to a certain concentration, $\Delta H_{ASA-gel}^{tot}$ (bottom). At low ASA concentrations, $\Delta H_{ASA-gel}$ exhibits a plateau for both PEGDA and PEGDA-co-AM gels. After titration of ASA to a concentration of 10 mM or greater, $\Delta H_{ASA-gel}$ decreases monotonically, approaching zero at large ASA concentrations. This behavior suggests that the mechanism of ASA-polymer interactions is by adsorption of ASA onto the polymer network. This is particularly apparent when examining the cumulative interaction enthalpy, $\Delta H_{ASA-gel}^{tot}$, which exhibits the qualitative features of an adsorption isotherm, such that $\Delta H_{ASA-gel}^{tot}$ is related to the equilibrium surface coverage of ASA on the polymer hydrogel. At low concentrations, the increase of $\Delta H_{ASA-gel}^{tot}$ with ASA concentration is roughly linear, corresponding to ideal adsorption of ASA where a majority of the injected solute molecules adsorb to the surface. However, at sufficiently large ASA concentrations, $\Delta H_{ASA-gel}^{tot}$ tends toward a plateau value, suggesting saturation of the hydrogel surface due to monolayer coverage of ASA. Attempts to fit simple, one-site adsorption isotherms to the data in FIG. 23 were unsuccessful, most likely due to the complicated structure and chemistry of the hydrogel surface. Nevertheless, the considerable range of concentration over which $\Delta H_{ASA-gel}^{tot}$ increased linearly with ASA concentration allowed for calculation of the enthalpy of adsorption of ASA at infinite dilution, $\Delta H_{ASA-gel}^{\infty}$ by averaging $\Delta H_{ASA-gel}$ over ASA concentrations in the plateau region (FIG. 23), resulting in $\Delta H_{ASA-gel}^{\infty} = -9.8$ kcal/mol for $PEG_{400}DA$ and $\Delta H_{ASA-gel}^{\infty} = -12.3$ kcal/mol for $PEG_{400}DA$-co-AM. This confirms that ASA-polymer interactions were more favorable for PEGDA-co-AM hydrogels compared to PEGDA hydrogels, and further suggests that the presence of the AM co-monomer enhanced adsorption of ASA.

Compared with the ASA system, the ACM-polymer interactions turned out to be much weaker in both the microgels (FIG. 22b), indicated from lower κ values. A marginal increase in κ was seen with modified gels, ranging from 35% ($M_n=130$ g/mol) to 14% ($M_n=700$ g/mol). Similar to ASA, ACM partitioned to a similar extent into the modified gel of all mesh sizes, whereas in unmodified gels, κ exhibited more apparent variation as a function of $M_n$. This result may also imply that ACM interacts stronger with AM than with PEGDA. Comparing the ASA to ACM systems, it is not apparent why ASA interacted stronger with both the polymers than ACM. One might expect the reverse since the ACM molecule carries more hydrogen-bond donors, and both PEGDA and AM are rich in hydrogen-bond acceptors. Complimentary functional group interactions, commonly solicited for interpreting the substrate effect on nucleation from solution, did not explain these observations, possibly because this approach does not account for the fact that both the polymer and the solute are well solvated. Increased cost of de-solvation required for ACM adsorption onto the polymer may have led to its decreased partitioning, since solute-solvent interactions are stronger for ACM than for ASA indicated by higher ACM solubility in 38/62 (v/v) ethanol/water mixture (90 mg/ml at 25° C.) than that of ASA (32 mg/ml at 25° C.).

Figure 22:
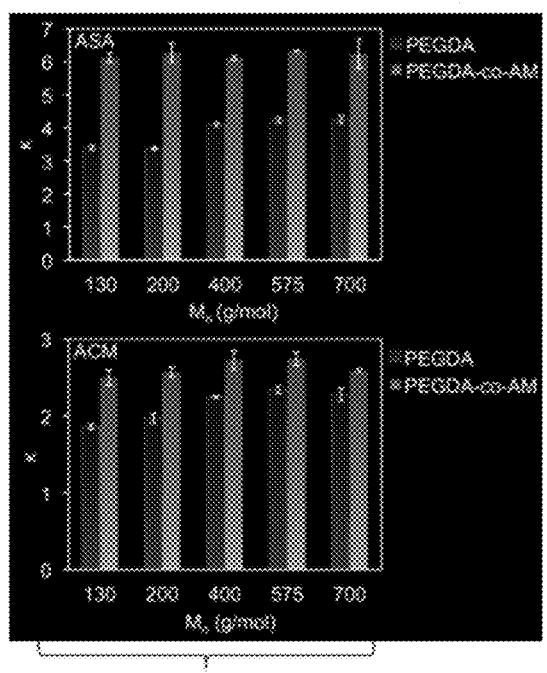
FIG. 22 graphs a comparison of partition coefficient, $\kappa$, in hydrogels for ASA (top) and ACM (bottom), according to some embodiments.

In FIG. 22: Comparison of partition coefficient, κ, in the PEGDA gels vs. PEGDA-co-AM gels for ASA (top) and ACM (bottom) systems. κ is defined as the ratio of solute mass fraction in solution confined in the gel to that in the bulk. The error bars are calculated from three to four independent repeats.

In FIG. 23: Enthalpy isotherms for adsorption of ASA onto $PEG_{400}DA$ (open symbols) and $PEG_{400}DA$-co-AM (closed symbols) microgels, including instantaneous (top) and cumulative (bottom) enthalpies of adsorption. Straight line gives fit to obtain the infinite dilution enthalpy of adsorption. Solid lines show the region over which the infinite dilution enthalpy of adsorption was calculated.

Effect of polymer gels on nucleation induction time statistics: To evaluate the impact of polymer-solute interactions on nucleation kinetics, induction times of ASA and ACM were measured with microgels of a series average mesh sizes before and after chemical modification suspended in respective supersaturated solutions. The volume fraction of microgels in the solution is so small ($\sim 10^{-5}$) that the solute partitioning in the gels does not affect the bulk concentration. For each system, a large number of experiments (50-100) were conducted to obtain the induction time probability distribution. The nucleation induction time generally follows the Poisson distribution. However, deviations can occur, as observed in this study, when there is more than one type of nucleation sites in a sample, giving rise to multiple Poisson processes with different characteristic time scales.

For samples with $PEG_MDA$ microgels, the nucleation induction time distributions reported in previous work can be faithfully described by stretched exponentials (Tables 5 and 6), $P=\exp[-(t/\tau)^\beta]$, where P is the probability to observe no crystallization event within time t, τ the average induction time. The stretched exponential exponent β served as a measure for the spread of time scales characterizing the nucleation process, or the distribution of kinetic barriers arisen from the heterogeneity of the system. Such heterogeneity can be attributed to the heterogeneity of the polymer microstructure identified using SANS, which resulted from a distribution of nucleation sites arising from spatial variations in both the mesh size and chemical composition of the hydrogel at nanometer length scales. Note that β varies with the average mesh size of the microgel. Polymer mesh size can impact the nucleation kinetics and an optimum average mesh size can be determined which corresponds to the fastest nucleation rate. At the optimum average mesh size, β is found to be the highest in both the cases of ASA and ACM (Table 5, M=400 g/mol; Table 6, M=200 g/mol). This is probably because, out of various types of nucleation sites in the microgel, the one with the optimum mesh size and conformation is dominant in quantity and activity, such that the majority of nucleation events take place at this type of nucleation site, leading to a narrower distribution of nucleation time scales. Taking this scenario to extreme, β should approach unity when the activity of a single type of nucleation site is so high that other nucleation sites are inactive by comparison.

Modification of PEGDA microgels with AM resulted in much faster nucleation kinetics of ASA overall. The nucleation induction time distributions were better described by two-exponential models (Table 7, FIG. 24) instead of the stretched exponentials obtained with PEGDA microgels (Table 5). Two exponential processes yielded two distinct time scales, $\tau_1$ and $\tau_2$, with $\tau_1$ an order of magnitude faster than $\tau_2$. Both the two exponential processes were much faster than those obtained with PEGDA microgels, indicating that strong polymer-solute interactions led to overall success of polymer gels in promoting nucleation. Two time scales possibly result from the presence of two dominant types of active nucleation sites on PEGDA-co-AM microgels. Recalling the hypothesized polymer microstructure as determined by SANS (FIG. 21), it is likely that the segregation of AM functional monomers into regions of high local acrylate density results in two largely different types of active sites for nucleation. One type, in the acrylate-lean (and thus AM-lean) regions of the gel, are such that interactions between the solute and PEG subchain dominate the nucleation process. The other, in the acrylate and AM-rich regions of the gel, are such that interactions between the solute and AM dominate the nucleation process. The latter AM-rich domains may serve as the more active nucleation sites due to favorable solute-AM interactions (as characterized by higher partition coefficient and adsorption enthalpy), which correspond to the shorter average induction time of ASA, and the vise-versa for the AM-lean domains. This interpretation is also consistent with the observation that the shorter time scale $T_1$ is much less sensitive to the variation in the PEG molecular weight M than $\tau_2$, the longer time scale (Table 7), since the AM-rich domain should be less affected by variation in the PEG subchain length than the AM-lean domain. In the case of PEGDA microgels, although there also exists structural heterogeneity due to microphase separation between acrylate-rich and acrylate-lean domains, such dramatic split of nucleation times scales was not observed, probably because only the acrylate-lean domains are nucleation active given that ASA mainly interacts with the PEG subchain in PEGDA, as discussed earlier.

Similarly, nucleation of ACM in the presence of PEGDA-co-AM microgels split into two exponential processes as well, probably for the same reasons discussed above. In contrast to the observations from ASA systems, the slower time scale $\tau_2$, possibly associated with the PEG rich, AM lean nucleation sites, was not reduced from those obtained with PEGDA microgels, although the faster time scale $\tau_1$ was shortened by at least an order of magnitude as in the case of ASA. This observation indicates that modification of PEGDA with AM promoted nucleation of ACM in terms of the overall effect, however, to a lesser extent compared with the ASA system. The data also suggest that the AM-rich nucleation sites are much more active than the AM-lean ones, evidenced by the two orders of magnitude difference between $\tau_1$ and $\tau_2$. However, such difference was not reflected in the partitioning results, where no significant improvement in the partition coefficients was seen after chemical modification. Others factors such as the templating effect may play a more important role in this case, which are discussed later.

TABLE 5

Average nucleation induction times of ASA with the presence of PEGDA microgels.

| | M (g/mol) | | | | |
| --- | --- | --- | --- | --- | --- |
| | Bulk/130 | 200 | 400 | 575 | 700 |
| τ (min) | Not detectable | 1052 | 66.7 | 3500 | 210000 |
| B | NA | 0.52 | 0.69 | 0.52 | 0.36 |
| $R^2$ | NA | 0.99 | 0.96 | 0.96 | 0.92 |

Supersaturation S=2.1. Detailed experimental conditions were described elsewhere.[9] Induction time distribution data were fitted with stretched exponentials via nonlinear least square regression: $P=\exp[-(t/\tau)^\beta]$, where P is the probability to observe no crystallization event within time t. The $R^2$ value corresponding to $PEG_{700}DA$ samples is lower since much fewer samples crystallized within the experimental time frame.

TABLE 6

Average nucleation induction times of ACM with the presence of PEGDA microgels.

| | M (g/mol) | | | | |
| --- | --- | --- | --- | --- | --- |
| | Bulk | 130 | 200 | 400 | 700 |
| τ (min) | 37000 | 1600 | 480 | 5300 | 37000 |
| B | 0.50 | 0.54 | 0.72 | 0.50 | 0.50 |
| $R^2$ | 0.97 | 0.96 | 0.96 | 0.97 | 0.97 |

Induction time distribution data were fitted with stretched exponentials via nonlinear least square regression: $P=\exp[-(t/\tau)^\beta]$.

TABLE 7

Average nucleation induction times of ASA with the presence of PEGDA-co-AM microgels.

| | M (g/mol) | | | | |
| --- | --- | --- | --- | --- | --- |
| | 130 | 200 | 400 | 575 | 700 |
| $\tau_1$ (min) | 170 | 21 | 39 | 51 | 33 |
| $\tau_2$ (min) | 4900 | 99 | 400 | 470 | 720 |
| A | 0.52 | 0.05 | 0.62 | 0.79 | 0.68 |
| $R^2$ | 0.98 | 0.99 | 0.99 | 0.99 | 0.99 |

Bulk solution is at the same crystallization condition as that with PEGDA microgels. Induction time distribution data were fitted with two exponentials via nonlinear least square regression: $P=a\times\exp(-t/\tau_1)+(1-a)\times\exp(-t/\tau_2)$.

TABLE 8

Average nucleation induction times of ACM with the presence of PEGDA-co-AM microgels.

| | M (g/mol) | | |
| --- | --- | --- | --- |
| | 130 | 200 | 400 |
| $\tau_1$ (min) | 55 | 88 | 70 |
| $\tau_2$ (min) | 1360 | 12400 | 35000 |
| a | 0.23 | 0.36 | 0.29 |
| $R^2$ | 0.91 | 0.96 | 0.97 |

Bulk solution is at the same crystallization condition as that with PEGDA microgels. Induction time distribution data were fitted with two exponentials via nonlinear least square regression: $P=a\times\exp(-t/\tau_1)+(1-a)\times\exp(-t/\tau_2)$.

Figure 24:
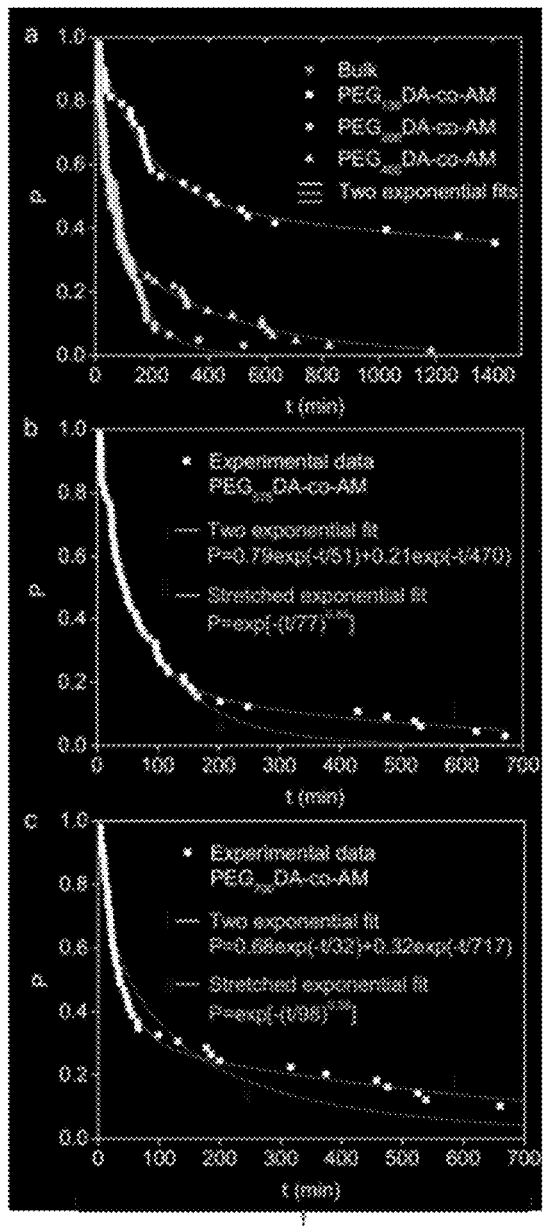
FIG. 24a graphs the effect of polymer mesh sizes on nucleation kinetics, according to some embodiments.
FIGS. 24b-24c graphs comparison of two exponential vs. stretched exponential models using $PEG_{575}DA$-co-AM (b) and $PEG_{700}DA$-co-AM (c) as representative examples.

In FIG. 24: Effect of PEGDA-co-AM microgels on nucleation induction time statistics of ASA. P is the probability for no nucleation event to occur within time t; a) Effect of polymer mesh sizes on nucleation kinetics. Fitted parameters following the two-exponential model are listed in Table 7. Data for $M_n$=575 and 700 g/mol are shown separately for clarity; b) and c) Comparison of two exponential vs. stretched exponential models using $PEG_{575}DA$-co-AM (b) and $PEG_{700}DA$-co-AM (c) as representative examples.

Several effects may have contributed to the observed enhancement in nucleation kinetics with chemically modified polymer gels. First, preferential partitioning can increase solute concentration in the gel. Particularly, given the adsorptive partitioning mechanism discussed earlier, the solute molecules are likely to be enriched around the polymer matrix. The resultant increase in local concentration may enhance effective solute-solute interactions. Higher solute concentration can lead to higher supersaturation in the gel, and hence larger driving force for nucleation. However, this is not necessarily the case, as described herein. Supersaturation (S) is the chemical potential difference (Δμ) in relationship $\Delta\mu=\mu_s-\mu_c=kT\ln S$, where $\mu_s$ and $\mu_c$ are chemical potentials of solute in the solution or gel phase and in the crystal phase. Since the gel and the solution are at equilibrium, the solute molecules possess the same chemical potential in the two phases, and therefore the supersaturation is not different in the gel from that in solution. Although the thermodynamic driving force may not increase due to the presence of the polymer, the polymer may still serve as a catalyst, which reduces the kinetic barrier to nucleation by concentrating the solute molecules to facilitate molecular cluster formation. PEGDA-co-AM gels were more effective than PEGDA in promoting ASA nucleation, which can be partially credited to higher average solute concentration in the gel (FIG. 22a), especially considering that the concentration in local domains may be even higher due to chemical heterogeneity of the gel, as discussed earlier. As for the ACM system, the average solute concentration increased only marginally in the modified gel (FIG. 22b), and as such its contribution to overall nucleation expedition is less significant than in the case of ASA. However, it is still remarkable that by incorporating AM into the PEGDA matrix, a fast nucleation process was created with average induction times orders of magnitude shorter than those obtained with PEGDA alone (Table 8). This phenomenon may not be attributed solely to the concentration effect at the chemical heterogeneity may polarize the solute concentration between the AM-rich and AM-lean segments but the extent of concentration polarization should be small, based on the fact that the partitioning coefficient did not increase much after replacing 50 v % of PEGDA with AM. Other contributing factors may include the difference in specific polymer-solute interactions (templating effect), or the nanoscale structural heterogeneity of the polymer gel. The templating effect by studying preferred crystal orientation on PEGDA and PEGDA-co-AM polymer films via X-ray diffraction was investigated.

Templating effect of the polymer gel on nucleation: The templating effect may affect crystal nucleation by aligning the solute molecules along the polymer chain via specific polymer-solute interactions. To capture specific polymer-solute interactions in a solvent environment, the crystal facets preferentially grown from a polymer surface in the solvent of interest were determined and the complimentary functional group interactions were inferred by inspecting the molecular structures of surfaces in contact. Smooth and flat polymer films were prepared following the same formulation as used in the microgel synthesis, except that no porogen and solvent were added to the pre-polymer mixture so as to minimize the variation in polymer mesh sizes, allowing the focus to be on the polymer chemistry effect.

Shown in FIG. 25a, PEGDA films preferentially templated the growth of (002) plane of ASA, and PEGDA-co-AM the (011) plane, judging from the relative peak intensities in the XRD patterns compared with those of the bulk crystals. This result was verified by the observations under the optical microscope that ASA crystals with elongated plate-like shapes lay on their sides on the PEGDA surface via the (002) planes (FIGS. 25d and 25e), and stood tilted on the PEGDA-co-AM film via the (011) plane (FIG. 25c). Comparing the molecular structures of (002) and (011) planes, it can be deduced that the methyl and phenyl groups of ASA dominating the (002) plane mainly interact with the PEGDA polymer, and the carboxyl group characteristic of the (011) plane may be responsible for interacting with the AM segments of PEGDA-co-AM. Such complimentary interactions between PEGDA and ASA are possible, because the phenyl and methyl hydrogens of ASA, being next to electron-withdrawing groups, have increased tendency to interact with the oxygen of PEGDA. This type of C—H . . . O interactions, though much weaker than primary hydrogen bonding, is abundant in many crystal systems, such as the aspirin crystal in which the methyl hydrogen interacts with the carbonyl oxygen in the ester group to form a dimer-like supermolecular synthon. However, one might expect that the carboxyl group of ASA should primarily interact with PEGDA via hydrogen bonding instead of phenyl and methyl groups. This scenario is not observed probably because the ASA carboxyl group is well solvated by ethanol and water, and as such its interaction with PEGDA is hindered. Compared with PEGDA, the AM segments in the PEGDA-co-AM polymer carry higher density of stronger hydrogen bond acceptors in amide moieties, which may be more effective in completing with ethanol and water to form hydrogen bonds with ASA carboxyl groups. To summarize, the observed preferred crystal orientation induced by specific polymer-solute interactions provides strong evidence for the templating effect of the polymer film on nucleation. ASA interacts with PEGDA via weak C—H . . . O interactions, whereas its interaction with PEGDA-co-AM is much stronger, possibly via hydrogen bonds formed between ASA and AM. This result is consistent with the observed higher ASA partitioning in PEGDA-co-AM, and stronger binding between the two as measured by the ASA adsorption enthalpy on the polymer. Given stronger interactions with one end of the ASA molecule, AM was found to be more effective in aligning ASA molecules along the polymer chain, and thereby lowered the entropic penalty during nucleus formation, leading to further shortened induction times.

Figure 25:
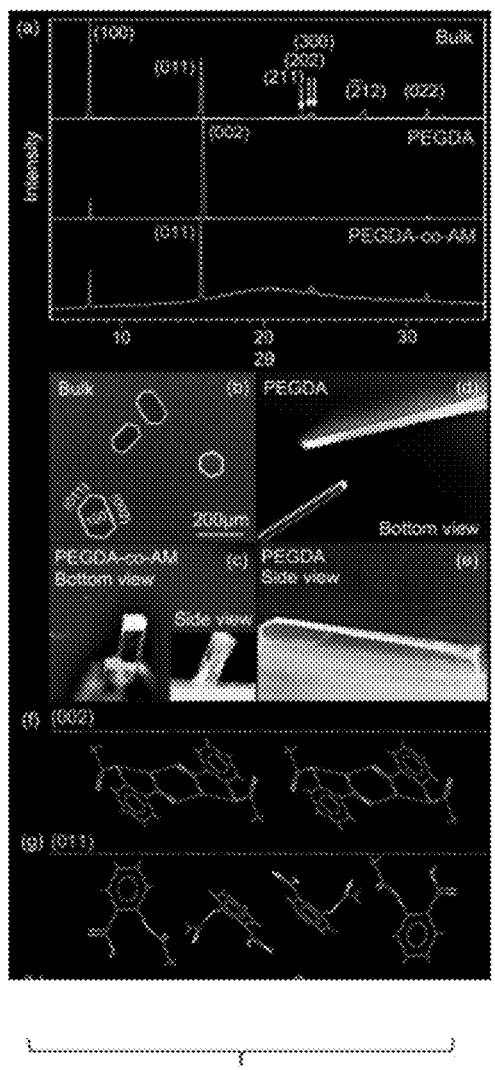
FIG. 25a shows XRD patterns of ASA crystals grown from PEGDA polymer films, PEGDA-co-AM polymer films, and from a bulk solution, according to some embodiments.
FIGS. 25b-25e show optical images of ASA crystals nucleated from bulk (b), a PEGDA-co-AM surface (c), and a PEGDA surface (d-e), according to some embodiments.
FIGS. 25f-25g illustrate molecular structures of (002) and (011) facets of ASA crystals, according to some embodiments.

In FIG. 25: Preferred orientation of ASA crystals on polymer films; (a) Comparison of XRD patterns of ASA crystals grew from PEGDA and PEGDA-co-AM polymer films to that of bulk crystals. The results are not sensitive to variation in $M_n$ and representative patterns are shown. (002) peak is separated from the (011) peak by a 2θ angle of 0.17 degree (calculated from Cambridge Structure Database). The two peaks can be unambiguously identified given that the resolution of XRD measurement is 0.02°; (b-e) Optical images of ASA crystals nucleated from bulk (b), the PEGDA-co-AM surface (c), and the PEGDA surface (d-e); Scale bar is the same for all images; (f-g) Molecular structures of (002) and (011) facets of ASA crystal. The dotted line indicates the top surface of the corresponding facet.

Similarly, preferred orientation of ACM crystals on polymer films was also observed, which further verifies the existence of templating effect imposed by the polymer network. XRD study showed that PEGDA induced growth of (011) and its higher index plane (022) almost exclusively, while PEGDA-co-AM preferentially templated (10$\bar{1}$) and its higher index plane (20$\bar{2}$) as well as (11$\bar{1}$) (FIG. 26a). It is evident from the optical images (FIGS. 26b-26e) that the prism-shaped ACM crystals exhibited random orientations when crystallized from bulk, and seemed to assume certain through-plane orientations when nucleated on the respective films, judging from similar crystal morphology from the top view. Seen from molecular structures of templated crystal facets (FIGS. 26f-26h), all planes present phenolic hydroxyl groups to the surface, on the other hand, (10$\bar{1}$) and (11$\bar{1}$) planes are different in chemistry from (011) in that they better expose the amide group, although the difference is not as apparent as that between (002) and (011) of ASA. Such difference implies that after introducing AM into the PEGDA network, the polymer strengthens its interactions with ACM by forming hydrogen bonds with the amide group of ACM, in addition to with the phenolic hydroxyl group. These observations help explain the moderate increase in partition coefficients after gel modification. Interestingly, both the amide and phenolic hydroxyl groups that AM preferentially interacts with are also used for forming the ACM crystal structure (Form I), which is essentially a network of intermolecular hydrogen bonding between the two groups. This may suggest that, with the ability to hydrogen bond with both the groups in the solvent of interest, the AM segment could act like a 'catalyst' for crystal nucleation by facilitating hydrogen bond formation among the aligned ACM molecules, and lead to a fast nucleation process observed in the induction time study with modified gels (Table 8).

Figure 26:
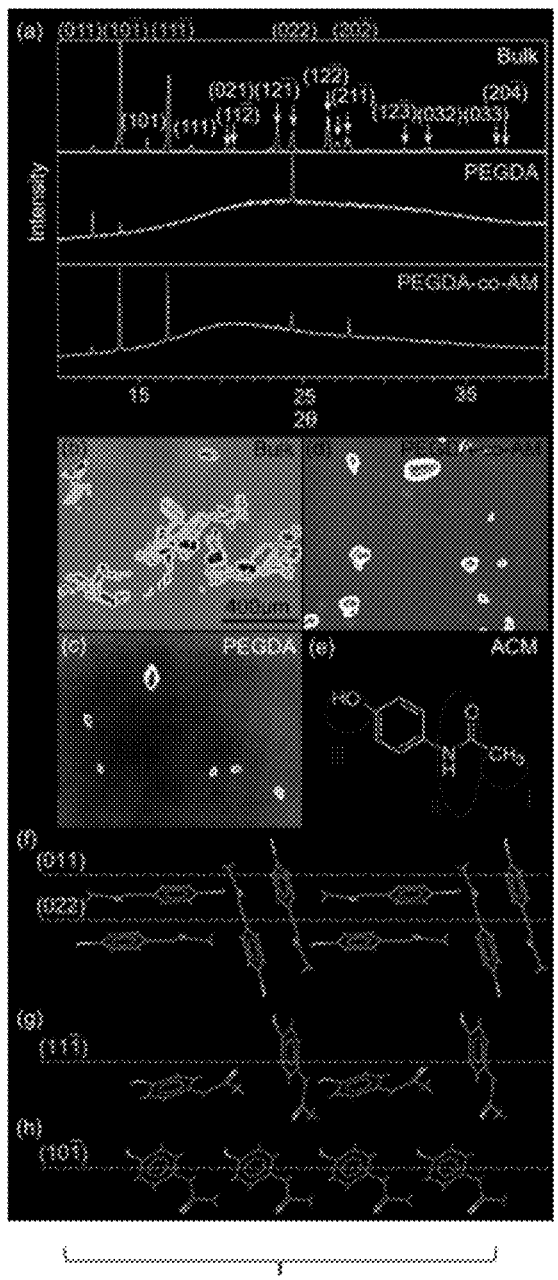
FIG. 26a shows XRD patterns of ACM crystals grown from PEGDA films, and PEGDA-co-AM polymer films, and bulk solution, according to some embodiments.
FIGS. 26b-26d show optical images of ACM crystals nucleated from bulk (b), a PEGDA surface (c), and a PEGDA-co-AM surface (d), according to some embodiments.
FIG. 26e shows the ACM molecular structure.
FIGS. 26f-26h show the molecular structures of the (011), (022), (11$\bar{1}$) and (10$\bar{1}$) facets of ASA crystals.

In FIG. 26: Preferred orientation of ACM crystals on polymer films; (a) Comparison of XRD patterns of ACM crystals grew from PEGDA and PEGDA-co-AM polymer films to that of bulk crystals. All ACM crystals are form I, the monoclinic form. (b-d) Optical images of ACM crystals nucleated from bulk (b), the PEGDA surface (c), and the PEGDA-co-AM surface (d). Scale bar is the same for all images; (e) ACM molecular structure. The functional group (i) preferentially interacts with PEGDA, (ii) with AM, and (iii) interacts with both PEGDA and AM. (f-h) Molecular structures of (011), (022), (11$\bar{1}$) and (10$\bar{1}$) facets of ASA crystal. Above the dotted line is the top surface of the corresponding facet.

In conclusion, the role of polymer-solute interactions in controlling solute nucleation was demonstrated by tuning the chemical composition of the polymer microgels used for inducing nucleation. When AM co-monomer was introduced into the PEGDA matrix via co-polymerization, ASA nucleation kinetics was promoted by up to four orders of magnitude, while nucleation of ACM was also enhanced by up to two orders of magnitude. Comparing the ASA and ACM systems, the extent of nucleation acceleration generally correlated with the strength of polymer-solute interactions as characterized by solute partition coefficients and adsorption enthalpy. The effect of polymer-solute interactions on nucleation further manifested in the split of nucleation time scales due to the presence of nucleation sites of distinct chemical compositions in the microgels, inferred from SANS data. Favorable polymer-solute interactions promoted nucleation by two means. First, it led to higher solute concentration in the gel, which enhanced the effective solute-solute interactions. Second, specific polymer solute interactions, as evidenced by the preferred crystal orientation on polymers, facilitated molecular alignment along the polymer chain.

EXPERIMENTAL SECTION

Materials: Poly(ethylene glycol) diacrylate with average molecular weights of M=200, 400, 575, and 700 g/mol and tri(ethylene glycol) diacrylate (M=130 g/mol), 4-acryloyl morpholine, poly(ethylene glycol) with M=200 g/mol (PEG$_{200}$), 2-hydroxy-2-methyl-1-phenyl-propan-1-one (DC1173) photoinitiator, Tween20 non-ionic surfactant, and ethanol (99.9%) were purchased from Sigma Aldrich Chemical Co. and used as received with no further purification. Deionized water (18.3MΩ) was obtained using a Millipore MilliQ purification system. For PEGDA microgel pre-cursors, solutions containing 25% PEG$_M$DA, 25% PEG$_{200}$, and 5% DC1173 by volume in ethanol were prepared for each of the values of the molecular weight M used. Similarly, for PEGDA-co-AM microgels, solutions containing 15% PEG$_M$DA, 15% AM, 25% PEG$_{200}$, and 5% DC1173 photoinitiator by volume in ethanol were prepared for each of the values of the molecular weight M used. Aspirin (99%) was purchased from Alfa Aesar and acetaminophen (99.0%) from Sigma Aldrich, both used with no further purification. Per-deuterated ethanol (d-ethanol, 99.9%), was purchased from Cambridge Isotope Laboratories, and used without further purification.

Microgel synthesis: Cuboid microgel particles were synthesized by stop flow lithography (SFL). Microfluidic channels with straight, rectangular cross-section (width=300 µm, height=30 µm) were prepared by soft lithography. Briefly, polydimethylsiloxane (PDMS, Sylgard 184, Dow Corning) was poured on an SU-8 photoresist patterned silicon wafer and cured to create a bas-relief microchannel device. Channels with end reservoirs were cut from the wafer with a scalpel and inlet and outlet ports were punched into the device with a blunt syringe (Small Parts, Inc.) to introduce the hydrogel pre-cursors. A photomask featured with square shapes was designed using AUTOCAD and printed at 50,800 dpi by FineLine Imaging (Colorado Springs, Colo.). For SFL, the microfluidic device was placed on a translating stage inverted microscope. The inlet channel was loaded with a hydrogel pre-cursor using a pressure-controlled manifold. The mask was placed in the field-stop of the microscope and square features were projected to the pre-cursor by ultraviolet (UV) exposure from a Lumen 200 lamp (Prior) through a wide excitation UV filter set (11000v2: UV, Chroma) while the flow of pre-cursor was stopped. The ultimate feature sizes of the patterned squares were 30 µm×30 µm, determined through fluorescence imaging of the microchannel during UV illumination. Pulses of UV exposure were obtained by a computer-aided UV shutter (UniBlitz). Incident UV intensities were measured using a UVA Power and Dose meter (ACCU-CAL-30 UVA, DYMAX). In all experiments, the measured exposure was 0.89 µW, and the UV exposure time was fixed at 200 msec. Particles were collected through the outlet channel into a microcentrifuge tube reservoir containing 0.2% v/v Tween20 in a mixture of 62/38 water/ethanol (v/v). Tween20 was added to the outlet reservoir in order to render the microgels colloidally stable during purification.

SFL was performed until approximately 50,000 particles were synthesized. The reservoir tube containing particles was then removed from the microfluidic device. The tube was placed in a minicentrifuge (Galaxy MiniStar, VWR Scientific) at 6000 rpm for 8 seconds in order to sediment the microgels. The supernatant was removed, and the particles were re-suspended in 1 mL of a rinsing fluid and vortex mixed for 10 seconds. This procedure was repeated several times in order to eliminate any remaining unreacted pre-polymer solution. The first 3 washes were performed using 62/38 water/ethanol (v/v) with 0.2% Tween20, and 3 final washes were performed using 62/38 water/ethanol (v/v) with no Tween20 to eliminate excess surfactant.

Equilibrium swelling measurements: Equilibrium swelling measurements were carried out as follows. Briefly, it was assumed that the as-synthesized dimensions of the microgels within the preparative microfluidic device were in the "relaxed" state (corresponding to a θ-solvent for the polymer), and their side length, L$_0$, was measured in situ. After purification and transfer into the appropriate crystallization solvent, the swollen side length, L, dimensions of the microgels were measured using DIC microscopy. These measurements were used to obtain the volumetric swelling ratio, R=(L/L$_0$)$^3$, assuming isotropic swelling of the microgel. Finally, the apparent average mesh size ξ was estimated using Flory-Rehner theory, which gives the average PEG$_M$DA molecular weight between cross-links, $\overline{M}_c$, as $$\frac{1}{\overline{M}_c} = \frac{2}{M} - \frac{\ln(1-R\phi_{p,0}) + R\phi_{p,0} + \chi(R\phi_{p,0})^2}{\phi_{p,0}\rho_p \underline{V}_s \left(R^{1/3} - \frac{R}{2}\right)} \quad (2)$$

where χ is the Flory chi parameter, ρ$_p$ is the density of the polymer, and $\underline{V}_s$ is the molar volume of the solvent. The quantity $\phi_{p,0}$ is the volume fraction of polymer in the microgel, where it is assume that the polymerization proceeds to completion, and thus $\phi_{p,0}$ is equal to the volume fraction of monomers in the hydrogel pre-cursor. Subsequently, the apparent, average mesh size of the hydrogel, ξ, is given by $$\xi = R\phi_{p,0}^{1/2}\left(\frac{2C\overline{M}_c}{\overline{M}_n}\right)^{1/2} l \quad (3)$$

where C is the characteristic ratio and l is the average bond length of the polymer. Estimations of ξ were carried out using model parameters for PEGDA in a water-ethanol. It was assumed that these model parameters were unchanged by either the PEG$_M$DA molecular weight or the presence of the co-monomer AM. The latter is a particularly significant approximation, and will be evaluated subsequently.

Small angle neutron scattering (SANS): SANS was performed at the National Institute of Standards and Technology Center for Neutron Research (NCNR). Samples were prepared by loading hydrogel pre-cursors (with the compositions previously described) for the PEG$_{200}$DA, PEG$_{700}$DA, PEG$_{200}$DA-co-AM, and PEG$_{700}$DA-co-AM microgels into standard titanium scattering cells with a path length of 1 mm. In order to polymerize the material, samples were irradiated with a handheld UV lamp with an output intensity of 0.2 mW/cm$^2$ for 1 minute, resulting in a total UV dose which is approximately equivalent to that supplied during SFL of microgel particles.

SANS measurements were carried out on the NG7 30 m SANS instrument with the 10CB sample environment. Temperature control was obtained using a Julaba temperature bath unit at 25° C., and samples were left to equilibrate for at least 30 min prior to measurement. Scattering using incident neutrons of wavelength λ=6 Å and a wavelength spread (FWHM) of Δλ/λ=11% was collected at detector distances of 1 m with 20 cm offset, 4 m, and 13.5 m for high-q measurements. Scattering using incident neutrons of wavelength λ=8.09 Å and a wavelength spread (FWHM) of Δλ/λ=11% was collected at a detector distances of 15.3 m for low-q measurements. USANS measurements were performed on the BT5 perfect crystal diffractometer within the 6CB sample environment. Temperature control was obtained using a Julaba temperature bath unit, and samples were left to equilibrate for at least 30 min prior to measurement. Data were reduced using NIST IGOR software package in order to obtain the absolute scattered intensity, I(q). The incoherent background intensity, $I_{bk}$, was determined using a Porod analysis of the data at high q-values.

Partition coefficient measurements: Partition coefficients of ASA in PEGDA-co-AM gels from its bulk solution were determined as follows. In brief, a series of gels with varying mesh sizes of approximately 5 mm in diameter and 0.5 mm in thickness were synthesized via UV polymerization following the same formula as used in the microgel synthesis. The residue solvent, porogen and monomer molecules were removed by extensive washing with solvent ethanol and subsequent vacuum drying. The dry gels were then immersed in excessive volume of 38 mg/ml ASA solution in 38/62 (v/v) ethanol/water at 15° C. for overnight. After equilibrium swelling was reached, the swollen gels were pad dried and dropped into excessive volume of water to release ASA. The total mass of ASA released was determined by measuring the equilibrium concentration of its degradation product in water, salicylic acid (SA), with UV-Vis spectroscopy, after ASA aqueous solution was aged for a week to achieve complete hydrolysis. The ASA partition coefficient was calculated as the ratio of ASA mass fraction in solution absorbed by the gel to that in bulk solution. Partition coefficient of ACM was determined by the same method. The gels were immersed in 95 mg/ml ACM solution at 8° C. instead. Since ACM is stable in water, its concentration was determined directly after the swollen gel was immersed in water for 24 hours. Three to four independent repeats were carried out for each type of sample to obtain the standard error of the partition coefficient.

Isothermal titration calorimetry (ITC): ITC measurements were performed on a TA Instruments NanoITC calorimeter. All experiments were performed at 23° C. using injections of $\Delta V=10$ μL of titrant, with a waiting time of 1000 sec in between injections and 25 injections per measurement. For all measurements, The differential heat input, q(t), was measured as a function of time t over all injections, followed by integration of q(t) over each individual injection to obtain the molar heat of injection, Q(T,P,c). The molar heat of injection can then be cumulatively added over all previous injections, yielding the total molar heat, $Q_{tot}$(T,P,c).

The primary measurement involves titration of a solution containing $c_{inj}$=21 mg/mL ASA in 38/62 (v/v) ethanol/water (loaded in the injection syringe) into a suspension containing microgel particles at a concentration of 1 particle/μL in 38/62 (v/v) ethanol/water. For this process, the molar heat of injection contains several contributions $$Q(T,P,c)=c_{inj}\Delta V(\Delta H_{ASA-gel}(T,P,c)+\Delta H_{dil}^{ASA}(T,P,c)+\Delta H_{dil}^{gel}(T,P,c)) \quad (4)$$

where $\Delta H_{ASA-gel}$ is the molar enthalpy of interaction between ASA and the microgel particles, and $\Delta H_{dil}^i$ is the molar enthalpy of dilution of component i (ASA or gel, respectively) in 38/62 (v/v) ethanol/water. In order to determine $\Delta H_{ASA-gel}$, independent measurements of the $\Delta H_{dil}^{ASA}$ and $\Delta H_{dil}^{gel}$ were made by performing measurements where 21 mg/mL ASA in 38/62 (v/v) ethanol/water was injected into a sample containing only 38/62 (v/v) ethanol/water without particles, and where 38/62 (v/v) ethanol/water without ASA was injected into a 1 particle/μL suspension 38/62 (v/v) ethanol/water. Subsequently, eq. (X) was used to subtract the measured dilution enthalpies from the initial measurements of Q(T,P,c) in order to obtain $\Delta H_{ASA-gel}$. Subsequently, the total, cumulative enthalpy evolved over all injections due to polymer-solute interactions, $\Delta H_{ASA-gel}^{tot}$, is calculated by summing the instantaneous enthalpy of interaction, $\Delta H_{ASA-gel}$, over all injections:

$$\Delta H_{ASA-gel}^{tot}(T,P,c) = \sum_{c_j=0}^{c} \Delta H_{ASA-gel}(T,P,c_j) \quad (5)$$

where $c_j$ is the concentration of the $j^{th}$ injection.

Nucleation induction time measurement: Crystallization of ASA from 38/62 (v/v) ethanol/water mixture in the presence of PEGDA-co-AM microgels of various mesh sizes were conducted in an RS10 Clarity Solubility Station (Thermo Fisher Scientific). Around 500 microgels were dispersed in every 1 ml of 38 mg/ml ASA solutions in 38/62 (v/v) ethanol/water mixture, and kept suspended by stiffing the solution at 700 rpm. 10 such samples were loaded into the Clarity station at once and quench cooled to 15° C. to generate a supersaturation of 2.1. The onset of crystallization was signaled by the sudden drop of IR transmission signal through the solution. The time taken from the moment the desired supersaturation was achieved to the moment the IR signal dropped was the nucleation induction time. 10 samples were cycled 5 to 10 times to yield the induction time probability distribution. Experimental conditions were kept the same for samples with PEGDA gels and those with PEGDA-co-AM gels for direct comparison. During the experiments, the solution was inspected under the optical microscope at intervals to make sure the microgels were neither aggregated nor degraded. For ACM, same procedures were followed with 95 mg/ml ACM solution in 38/62 (v/v) ethanol/water cooled to 8° C. to achieve a supersaturation of 3.7.

Preferred crystal orientation via XRD: Polymer films of various PEG molecular weights were synthesized via UV polymerization using pre-polymer mixtures of the same formulations as used for microgel synthesis, but without adding solvent ethanol and porogen PEG200. 30 μl pre-polymer mixture was sandwiched between a glass slide and a quartz slide, both 75 mm×25 mm in size. The glass slide was silanized with vinyl trichlorosilane, which co-polymerizes with the monomer to graft the polymer film to the glass substrate via covalent bonds. The quartz slide was used as a template to make polymer films with the minimum surface roughness possible. The sandwiched pre-polymer mixture was subjected to 70 mW/cm$^2$ UV light for 5 min to complete the polymerization, with the whole sample area irradiated fairly uniformly in the 5000-EC UV Curing Flood Lamp (Dymax Corporation). The quartz slide was subsequently lifted to leave the flat and smooth polymer film conformed to the glass substrate. After synthesis, the polymer films were immersed vertically in 25 mg/ml ASA solution in 38/62 (v/v) ethanol/water mixture, which was filtered with 0.45 μm PTFE membrane syringe filter before adding the polymer films. The solution was then sealed and cooled from 25° C. to 3° C., and visually inspected every hour. Once crystals were spotted, the polymer film was withdrawn from the solution to terminate crystallization and immediately dipped into D.I. water tank vertically to remove loosely attached crystals from bulk (ASA is essentially insoluble in water at 3° C.). The backside of the glass substrate was used as a control to determine if all loose crystals were removed from the polymer film. Bulk crystals were obtained at the same condition and serves as the control sample for XRD analysis. For ACM system, same procedure was carried out with 80 mg/ml ACM solution in 38/62 (v/v) ethanol/water mixture.

The specific crystal planes grown from the polymer film was analyzed using PANalytical X'Pert PRO Theta/Theta Powder X-Ray Diffraction System with Cu tube and X'Celerator high-speed detector. 20 mm×20 mm sample area was irradiated by the X-ray in one scan using programmable divergence slit with 20 mm irradiated length and 20 mm mask to ensure enough crystals on the polymer film were sampled to yield the statistically representative preferred orientation. Three scans were performed with one polymer film to cover almost the entire surface area. Since only the diffraction from the crystal plane parallel to the polymer film surface was seen by the X-ray detector, the peak that was significantly more intense relative to that of bulk crystals corresponds to the preferred nucleation face.

Example 5

The following example describes non-limiting embodiments relating to crystallization of polymorphs at confined interfaces.

Introduction: Controlling polymorphism, the ability of a compound to self-assemble into multiple crystal structures, has been a long-standing challenge in various fields of application. In particular, for pharmaceutical systems, polymorphs often exhibit distinct physical properties, which have profound impact on drug bioavailability, stability, processability, etc. Both nucleation and crystal growth, two steps constituting a crystallization process, were shown to affect polymorphic outcomes. The lack of understanding and control of nucleation, however, remains as a major roadblock in current polymorphism research. One of the most challenging, yet less-explored aspects in controlling nucleation of polymorphs is to decipher the role of interfaces in the nucleation process, since in practice almost all nucleation events occur heterogeneously, a.k.a, at an foreign interface. Designed nucleation substrates can be very useful in controlling polymorphism. For instance, some molecular compounds tend to crystallize in multiple polymorphs concomitantly under the same condition, which could be caused by assorted unknown nucleation sites in the solution. By 'seeding' the solution with designed nucleation 'catalyst' to selectively lower the nucleation barrier of a particular polymorph, heterogeneous nucleation induced by unintended contaminants can be avoided and controlled polymorph nucleation can be achieved.

Several types of substrates have been studied for screening or controlling polymorphs of molecular crystals, including crystalline substrates, 2D ordered surfaces such as self-assembled monolayers, and insoluble polymer surfaces. On these flat and smooth substrates, polymorph selectivity seems to be best achieved when both lattice matching (epitaxy) and complimentary chemical interactions at the crystal-substrate interface are satisfied. In recent years, materials imposing a nanoscopically confined environment for crystallization have also been explored for polymorph control, such as controlled pore glass with pores ranging from a few to a hundred nanometers, and microemulsions with drop sizes of 2-10 nanometers. Stabilization of metastable polymorphs in nanoconfinement sufficiently small was often observed. To explain these observations, evidence was presented that the large surface area to volume ratio can alter the relative polymorph stability. Another hypothesis frequently evoked states that when the pore size becomes smaller than the critical nucleus size of a polymorph, its crystallization was hindered in confinement. However, these arguments fail to account for the nucleation-templating effect of confinement interfaces. Moreover, the kinetic aspect of polymorph control under nanoconfinement has been ignored, which is particularly glaring given the definitive role of nucleation kinetics in affecting polymorphic outcomes. In fact, systematic studies on the kinetics of polymorph nucleation have been scarcely reported in general, not only in the nanoconfinement literature.

This example describes the of a novel material, polymer microgels, for understanding and controlling polymorph crystallization of molecular compounds in a confined environment. The microgels exhibited a mesh-like structure, formed by cross-linking polyethylene glycol diacrylate ($PEG_MDA$) of various PEG subchain molecular weight M (g/mol). When immersed in solution, the microgel swelled by uptaking solute and solvent molecules owing to favorable interactions, and the degree of swelling, which varied as a function of the PEG subchain length, defined its average mesh size, a quantity typically used for describing the microstructure of the swollen polymer network. With mesh sizes ranging from a few angstroms to several nanometers, the polymer network partitioned the absorbed solution and restricted the mobility of adsorbed solute molecules, as such providing a confined environment for crystallization to take place. Using polymer microgels of tunable mesh sizes, the nanoconfinement effect on polymorphism was investigated using two model compounds, carbamazepine (CBZ) and 5-methyl-2-[(2-nitrophenyl)amino]-3-thiophenecarbonitrile (ROY). Their polymorphic outcomes were strongly dependent on the polymer mesh size and chemical composition. In addition, there exhibited an evident correlation between the nucleation kinetics and the polymorphic outcome. The underlying mechanism was examined from three aspects: the influence of mesh size, preferential partitioning, and specific polymer-solute interactions. The selectivity of polymorph nucleation may arise from the templating effect driven by specific polymer-solute interactions, which, facilitated with an optimum spatial configuration imposed by the confinement effect, may enhance the nucleation of a particular polymorph to the greatest extent.

Results and Discussion: Monodispersed cubelike $PEG_MDA$ microgels (FIG. 27 left), with M ranging from 130 to 700 g/mol were synthesized by Stop-Flow Lithography, The mesh sizes vary from 0.7 to 1.5 nm in solvent ethanol (Table 9), estimated from equilibrium swelling by the Flory-Rehner theory. The accuracy of this method for obtaining mesh sizes has been confirmed with Small-Angle Neutron Scattering in a different solvent. The microgels were utilized for controlling polymorph crystallization by suspending ~10 μg of microgels per 1 ml solution by stiffing. Such a low microgel concentration may be sufficient to effect drastic change in the crystallization behavior (discussed later), underscoring the effectiveness of polymer microgels in controlling crystallization. In all crystallization experiments, supersaturation of the solution was generated by cooling instead of solvent evaporation, despite its popularity in numerous polymorph studies, to yield better control over the crystallization process.

CBZ and ROY were selected as model compounds to represent both packing polymorphism (CBZ) and conformational polymorphism (ROY), where CBZ polymorphs have the same conformer arranged in differing molecular packing motifs, and ROY, in comparison, assumes distinctive molecular conformations in various packing arrangements, altering its conjugation state and thus the color among different polymorphs. Both molecules have been studied extensively for purposes of polymorph screening and control. CBZ possesses four known anhydrous forms, and ROY has ten known forms with seven structurally characterized. The complexity of the two systems poses challenges for their polymorph control. Specifically, concomitant crystallization (simultaneous crystallization of multiple forms in the same liquid), has been reported for both the systems. In addition, crystallization of ROY polymorphs also suffers from poor reproducibility, owing to the stochastic nature of its polymorph crystallization.

Crystallization of CBZ polymorphs induced by microgels: Out of the four known anhydrous forms of CBZ, namely, Triclinic form I, Trigonal form II, Primitive monoclinic form III, and C-centered monoclinic form IV, form III is the most stable under ambient conditions, followed by form I, IV and II, with the energy separation between form III and II less than 0.7 kcal/mol. Such a narrow energy window suggests the sensitivity of CBZ crystallization to experimental parameters. There have been some inconsistencies in previous reports on the CBZ polymorphic outcome during crystallization from solution under similar conditions. For instance, when crystallized from highly supersaturated ethanol solution (often with supersaturation S>3) by cooling to low temperatures (T<10° C.), various forms have been obtained. At a lower supersaturation (S=2) and higher temperature (T=25° C.), concomitant crystallization of forms II and III has been observed also from ethanol solution. In this example, CBZ crystallization was found to be quite sensitive to experimental conditions such as solid impurity concentration, solution water content (trace amount), and stirring speed etc., which could explain some of the aforementioned inconsistencies (e.g., see Methods section). Therefore, all crystallization conditions were strictly controlled to yield reproducible results.

Figure 27:
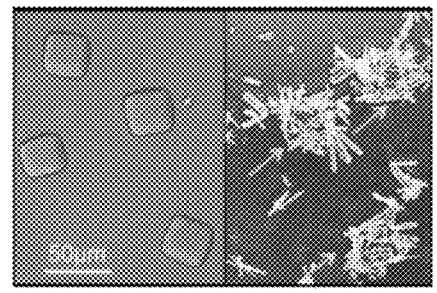
FIG. 27 shows optical micrographs of PEG400¬DA microgels as synthesized (left) and CBZ form II needles grown on PEG400DA (right), according to some embodiments.

At the experimental conditions employed (S=1.63, T=25° C., 2 ml purified solution stirred at 300 rpm), concomitant crystallization of Forms I and II was consistently observed (~100 trials) when crystallized from the bulk of ethanol solution (Table 9), both polymorphs with needle-like crystal habits. Occasionally, pure Form III was also obtained from bulk experiments. The possibility of observing both I and II forms due to solvent-mediated polymorph transformation was eliminated because the polymorphic composition did not exhibit statically significant change during aging of the crystal mixtures in solution from the onset of nucleation, which were sampled at intervals and characterized by XRD. Interestingly, when PEG$_M$DA microgels with M≥400 g/mol were added into the solution, pure Form II was crystallized (~250 trials) as identified by XRD, whose needle-shaped crystals were observed to grow from the microgel surface (FIG. 27 right). However, such polymorph selectivity could not be attained using microgels with M<400 g/mol (~100 trials) where the polymorphic outcome was quite similar to that of the bulk samples (Table 9), only with a decreased mass fraction of Form I in the mixture obtained (FIG. 28 discussed later) and a lower frequency of occurrence of Form III.

In FIG. 27: Optical micrographs of PEG$_{400}$DA microgels as synthesized (left) and CBZ form II needles grown on PEG$_{400}$DA (right), in which three microgels covered with CBZ needles are indicated with arrows, and the contour of the middle one is traced with lines to delineate the cubic gel.

TABLE 9

Effect of PEG$_M$DA microgels on the average nucleation induction times and polymorphic outcomes of CBZ.

| M (g/mol) | Bulk | 130 | 200 | 400 | 575 | 700 |
|---|---|---|---|---|---|---|
| ξ (nm) | NA | 0.7 | 0.8 | 1.1 | 1.3 | 1.5 |
| Polymorph | II & I, occasionally III | II & I | II & I | II | II | II |
| τ (min) | 427 ± 13 | 222 ± 5 | 174 ± 11 | 10.9 ± 0.3 | 33 ± 1 | 49 ± 1 |
| β | 0.86 | 0.99 | 0.73 | 1.00 | 0.61 | 0.94 |
| R$^2$ | 0.986 | 0.982 | 0.960 | 0.976 | 0.981 | 0.987 |

Average mesh size ξ was estimated from equilibrium swelling experiments in solvent ethanol. Polymorphic outcomes were analysized by XRD, and corresponding polymorphic compositions were shown in FIG. 28. Induction time distribution data were fitted with stretched exponentials via nonlinear least square regression: P=exp[−(t/τ)$^β$], where P is the probability to observe no crystallization event within time t. X-ray Diffraction patterns of CBZ were obtained from bulk solution and in the presence of PEG$_M$DA microgels with M=200 and 575 g/mol. CBZ forms I and II peaks were observed. A peak at 9.00° C. appeared in some patterns, corresponding to CBZ dihydrate which forms during filtration, especially when the ambient humidity is high.

Nucleation induction time statistics of CBZ were determined with or without the presence of PEGDA microgels, wherein P is the probability for observing no crystallization event within time t. Stretched exponential model was employed to fit the data (see Table 9).

Accompanying the impact on CBZ polymorphic outcomes is the ability of the microgels in altering the CBZ nucleation kinetics, characterized by the average nucleation induction time τ (Table 9). Induction time was measured by monitoring IR transmission signal passing through a solution in controlled temperature environment and stirring condition. Once nucleation occurred, the solution became turbid in seconds indicated by a sharp drop of IR signal, due to secondary nucleation and rapid crystal growth. The statistical nature of nucleation necessitated a large number of experiments (50-100) for obtaining the distribution of induction times, from which the average induction time τ was regressed with a stretched-exponential model, P(t)=exp[−(t/τ)$^β$], where P is the probability to observe no crystallization event within time t. In brief, the stretched-exponential model modified the single exponential model derived from the Poisson statistics, P(t)=exp(−t/τ) by adding an exponent β to the dimensionless induction time t/τ to capture the spread in characteristic time scales caused by a distribution of nucleation active sites present in the system.

Shown in Table 9, microgels with M=130 and 200 g/mol effectively shortened the CBZ average induction time by 2-3 fold relative to that of the bulk samples, whereas at least an order of magnitude reduction was observed with microgels of higher M. More importantly, there exhibited a strong correlation between the extent of nucleation acceleration and the polymorph selectivity, wherein Form II was exclusively obtained only with the microgels sufficiently effective in promoting nucleation. Considering that Form II is the least stable polymorph at ambient conditions, the observed polymorph selectivity towards a higher energy form may be driven by kinetic factors, in which case, the presence of microgels preferentially lowered the kinetic barrier to Form II nucleation, as opposed to switching the relative stability between Form I and II.

Mechanistic investigations into CBZ polymorph selectivity: The microgels could alter the relative nucleation rates of CBZ polymorphs through various means. First, the concentration effect was investigated, based on the knowledge that the microgels have the ability to concentrate solute molecules via favorable polymer-solute interactions. Equilibrium partitioning experiments revealed that CBZ concentration in the polymer gel was 3-4 times as high as that in the bulk (see Table 13). In addition, a generally higher partition coefficient $\kappa$ in microgels with larger M suggests that CBZ preferred interacting with PEG to acrylate segments. To assess the effect of solute concentration on polymorphic outcomes, bulk crystallization experiments were conducted at a series of starting concentrations and the resultant Form I and II mixtures were analyzed with XRD to quantify the polymorph compositions. Shown in FIG. 28, increasing solute concentration reduced the Form I mass fraction and thus biased the polymorphic outcome towards the less stable Form II. This trend was not unexpected since in practice less stable forms are typically generated by increasing the supersaturations to drive the system towards kinetic control regime. However, using this strategy Form I could not be eliminated to obtain pure Form II, even at concentration as high as 140 mg/ml (S=6.7). In fact, when concentration increased beyond 60 mg/ml, the polymorph composition became irreproducible since before the solution was cooled to desired supersaturation level, crystallization already ensued. In contrast, the microgels can take the system into a parameter space inaccessible through conventional means. For samples with microgels, the same trend was observed as with the bulk samples (FIG. 28), which indicated higher solute concentration in the gel could facilitate selective nucleation of Form II. The high degree of selectivity cannot be explained quantitatively with only the concentration effect, and thus other contributing factors were examined, such as the nucleation templating effect of the PEGDA polymer.

Partition coefficients ($\kappa$) of CBZ in PEG$_M$DA microgels from ethanol solutions were determined, wherein $\kappa$ is defined as the ratio of solute mass fraction in solution confined in the gel to that in the bulk.

Figure 28:
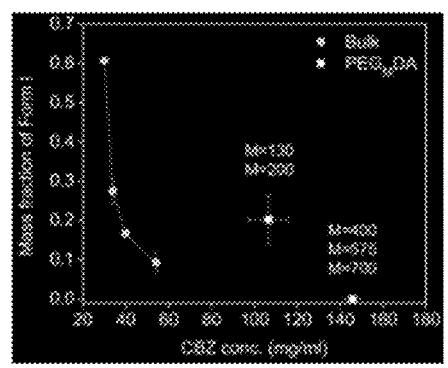
FIG. 28 illustrates the effect of solute concentration on the polymorphic composition of CBZ crystals, according to some embodiments.

In FIG. 28: Effect of solute concentration on the polymorphic composition of CBZ crystals. For samples with PEG$_M$DA microgels, X-axis corresponds to the effective solute concentration of solution inside the gel, calculated by multiplying the solute partition coefficient (see Table 13) with the bulk concentration, 34 mg/ml for all samples with microgels. The X error bars are from partition coefficient measurements, and the Y error bars calculated from XRD measurements on three independent samples. The mass fraction of Form I, $\eta$, was calculated following $$\eta = k \frac{I(\theta_I)}{I(\theta_I) + I(\theta_{II})},$$

where I denotes relative peak intensity. $\theta_I$ and $\theta_{II}$ are the characteristic peak positions (2θ) for Forms I and II, respectively. In this case, $\theta_I$=12.345° C. and $\theta_{II}$=5.046°. Coefficient k, experimentally determined, converts the peak intensity fraction to the polymorph mass fraction (see Methods section).

Besides increasing the solute concentration in the gel, favorable polymer-solute interactions can also induce a templating effect, by which it directs the CBZ molecules towards a particular orientation via molecular recognition events and thereby reducing the entropic cost during nucleus formation. This microscopic phenomenon can be expressed macroscopically as preferred orientation of crystals on flat polymer surfaces, which can be detected via XRD. The PEGDA polymer surface only induced nucleation of a particular set of crystal planes of Form II, i.e., (110) and its higher index planes, irrespective of the polymer mesh size or the PEG subchain molecular weight (FIG. 31a). Specificity as high as such suggests that the templating effect may be a substantial factor in microgel-induced polymorph selectivity. To identify the specific polymer-CBZ interaction responsible for directing Form II nucleation, the surface chemistry of II (110) and II (440) were compared against other major crystal facets not nucleated from the polymer surfaces, namely, II (410), I ($02\bar{2}$) and I ($02\bar{4}$) (Note that the XRD patterns were obtained with randomly oriented crystal powders, and therefore capture a statistical average of all crystal facets grown from the system). All II (410), I ($02\bar{2}$) and I ($02\bar{4}$) facets exhibited similar surface chemistries, dominated by the phenyl group on the azepine ring and decorated with carboxamide group (FIG. 31d; only I ($02\bar{2}$) is shown), which left the vinyl group a distinctive functionality characterizing the II (440) facet. This analysis implied that it is the vinyl group of CBZ mainly engaged in its interaction with PEGDA (FIG. 31e), possibly by forming the C—H . . . O between the CBZ vinylic hydrogen of CBZ and the oxygen of the PEG subchain. Albeit weak, such interactions were found to play an important role in directing nucleation process and in distinguishing polymorphs of many organic crystals.

In summary, both the concentration effect and the templating effect are found to contribute to the observed CBZ polymorph selectivity induced by polymer gels. Considering the striking similarity of the intermolecular interactions between Form I and II of CBZ, the polymorph selectivity achieved with the microgels is significant. It is also worth noting that the CBZ polymorphic outcomes were sensitive to the polymer mesh sizes, with exclusive nucleation of Form II only obtained using microgels of larger mesh sizes, the implication of which is discussed later and summarized as the mesh size effect.

Figure 29:
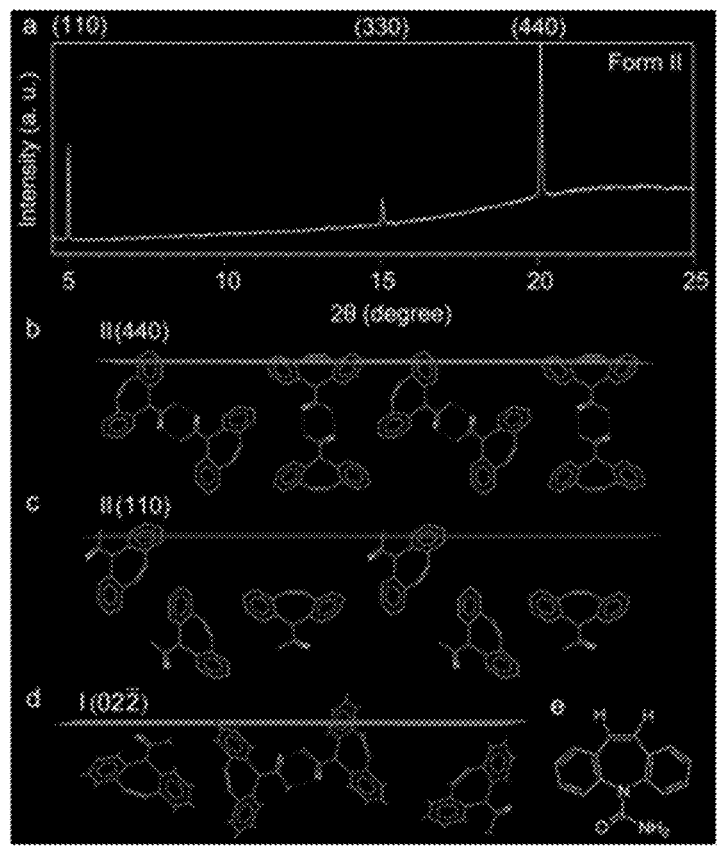
FIG. 29 shows CBZ-polymer interactions inferred from preferred crystal orientations, according to some embodiments.

In FIG. 29: Specific CBZ-polymer interactions inferred from preferred crystal orientations. (a) XRD pattern of CBZ crystals grown on PEG$_M$DA films. Relative peak intensities were found to be independent of M. A representative pattern is shown. (b, c) Surface structures of Form II facets preferentially nucleated on polymer surfaces. (d) Surface structure of a facet characteristic of Form I not grown from polymer surface. (e) Functionality inferred to preferentially interact with PEGDA polymer (colored blue).

Crystallization of ROY polymorphs induced by microgels: ROY crystallization is well known for its poor polymorph selectivity for two reasons. First, when crystallized from solution, multiple polymorphs can be obtained (often in pure forms, occasionally concomitant) from the same solution under seemingly identical condition. Second, during crystallization from supercooled melt, concomitant polymorphs are frequently observed controlled by both the nucleation and crystal growth kinetics. During solution crystallization, the poor selectivity may arise from a broad distribution of molecular conformations in solution, and/or the small free energy difference between ROY polymorphs as in the case of CBZ.

Figure 30:
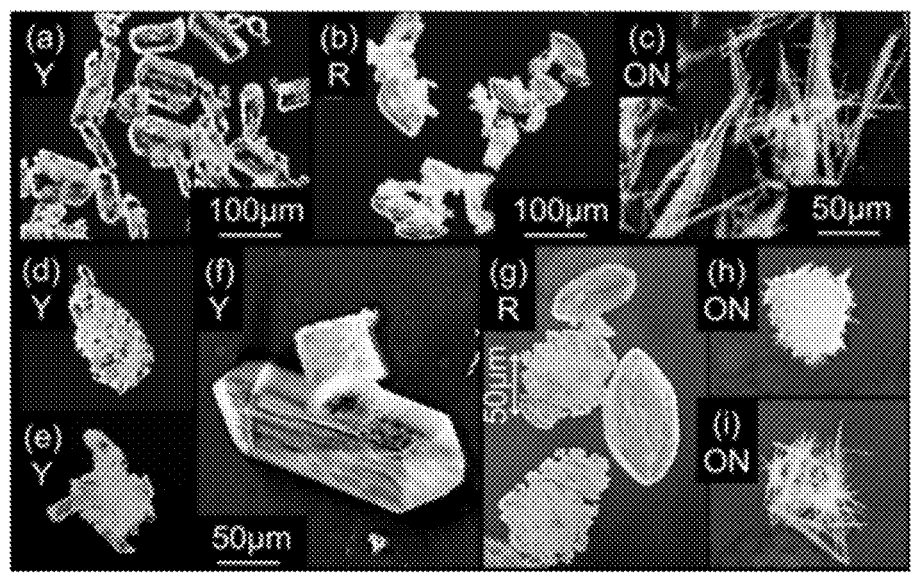
FIG. 30 shows optical micrographs of ROY crystallized from (a-c) bulk and on (d-i) microgels, according to some embodiments.

In FIG. 30: Optical micrographs of ROY crystallized from (a-c) bulk and on (d-i) microgels, specifically, with M=400, 575, 700, 400, 400, 400 g/mol in images d, e, f, g, h, i respectively. Y, R and ON denote yellow prism, red prism and orange needle forms. Scale bars for images (d-i) are the same as shown in (f). In images (d, e, g, h, i), the cubic microgels are buried with tiny ROY crystals grown from their surfaces, whereas in image (f), only one large single crystal nucleated on the gel, leaving the red-colored microgel clearly visible. The originally transparent microgel became red in solution due to high preferential partitioning of ROY into the gel (see Table 13) or polymer-solute interaction induced conformation change.

Figure 31:
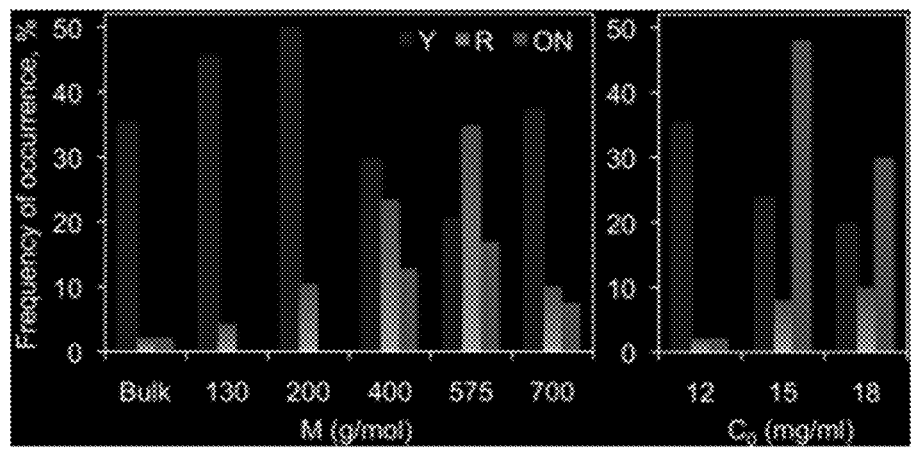
FIG. 31 shows polymorph frequency of occurrence in 12 mg/ml ROY-ethanol solution with or without microgels of various mesh sizes (left) and at higher solution concentrations (right), according to some embodiments.

In each experiment, crystallization of pure forms of either Y (yellow prisms), R (red prisms) or ON (orange needles) were observed from ethanol solution stochastically (FIG. 30), and their frequencies of occurrence were calculated by conducting 50-150 experiments in each case (FIG. 31). Nucleation induction time data from bulk solution or with $PEG_{130}DA$ microgels were fitted with the stretched exponential model and the average induction time thus regressed represents an average of all forms (Table 10), since the frequencies of occurrence for R and ON were too low for separate statistical analysis. Low values of stretched exponential exponent β (Table 10) indicate a wide spread of nucleation times scales, possibly associated with a broad conformation distribution of ROY in solution since β as low as such has not been observed with systems exhibiting packing polymorphism.[22] Induction time data obtained with microgels of M=200-700 g/mol can be described with multi-exponential models (Table 11), with each exponential decay process corresponding to each particular form, and its characteristic time scale the average nucleation induction time of each form. In the multi-exponential model, each exponential decay process may be better represented with a stretched exponential, however, a simple exponential suffices in this case and decent fit was obtained with $R^2$ very close to unity (Table 11). This may be due to the time scales corresponding to different polymorphs are at least an order of magnitude apart and thus, the spread of times scales within each decay process, described by the stretched exponential exponent β, becomes secondary in comparison.

For bulk crystallization without microgels, predominant Form Y at the chosen experimental condition (see Methods section) was observed, occasionally Form R and ON (FIGS. 30a-30c, FIG. 31 left). The relative stability of the three observed polymorphs are Y>ON>R at this condition. This observation is consistent with previous reports, for instance, primarily Y was obtained from various supercooled solutions. The addition of microgels had significant impact on ROY nucleation kinetics and polymorph frequency of occurrence, the extent of which varied considerably with the polymer mesh size. Shown in Table 10, $PEG_{130}DA$ microgels expedited nucleation of Y form, however, its effect on crystallization of other forms was not very pronounced. When $PEG_{200}DA$ microgels were injected into the ROY solution, nucleation of Y was further accelerated, all of which occurred within 100 min, and Form R also started appearing at a detectable rate. The observed promotion of Y and R nucleation kinetics was reflected in increased frequencies of occurrence for both the forms (FIG. 31 left). With addition of PEGDA gels of larger mesh sizes (Table 11), Form ON nucleation was accelerated into the detectable range as well, but its average rate was much slower than those of Forms Y and R in all cases. Meanwhile, nucleation of Form R continued to be promoted, until a maximum was reached with $PEG_{575}DA$ microgels, at which point the average induction time of R was reduced to 200 min from well over 10000 min without microgels. Correspondingly, the frequency of occurrence for R also peaked at M=575 g/mol, replacing Y to become the dominant polymorph (FIG. 31 left). Evidence of ROY polymorphs nucleated on microgels was shown in FIGS. 30d-30i. Previous experiments have found that the frequency of occurrence of Form R has been quite low compared with Y, ON during solution crystallization from various solvents, particularly when supersaturation was achieved by cooling as did in this example. While other methods have been used for screening rare ROY polymorphs, the reproducibility and selectivity were not reported. In this example, the addition of polymer microgels improved the Form R frequency of occurrence by up to 20 times even at relatively low supersaturation, which is not attainable by conventional means.

Nucleation induction time statistics of ROY with or without the presence of PEGDA microgels were determined. For each type of samples, 50-100 experiments were performed to obtain the induction time statistics wherein P is the probability for observing no crystallization event within time t is estimated from the fraction of samples haven't crystallized at this time point. Either stretched exponential model or multi-exponential models were employed to fit the data (see Tables 10 and 11).

TABLE 10

Average nucleation induction times of ROY in bulk and with $PEG_{130}DA$ microgels.

| Samples | τ, min | β | $R^2$ |
|---|---|---|---|
| Bulk | 10000 ± 2000 | 0.37 ± 0.02 | 0.97 |
| $PEG_{130}DA$ | 4000 ± 750 | 0.25 ± 0.01 | 0.97 |

Induction time distribution data were fitted with stretched exponentials via nonlinear least square regression: $P=\exp[-(t/\tau)^\beta]$, where P is the probability to observe no crystallization event within time t. τ is an average of induction times for all Y, R, ON forms.

TABLE 11

Average nucleation induction times of ROY with $PEG_MDA$ microgels, (M = 200-700 g/mol).

| Microgels | τ(Y), min | τ(R), min | τ(O), min | a | b | $R^2$ |
|---|---|---|---|---|---|---|
| $PEG_{200}DA$ | 26.0 ± 1.5 | 9000 ± 6000 | NA | 0.550 | NA | 0.983 |
| $PEG_{400}DA$ | 22.0 ± 0.6 | 1600 ± 400 | 3300 ± 1200 | 0.298 | 0.330 | 0.995 |
| $PEG_{575}DA$ | 10.0 ± 0.8 | 200 ± 20 | 2900 ± 500 | 0.205 | 0.350 | 0.996 |
| $PEG_{700}DA$ | 12.0 ± 1.2 | 2600 ± 400* | | 0.375 | NA | 0.967 |

Induction time distribution data were fitted with superposition of two or three exponentials via nonlinear least square regression. Two-exponential fit was employed for $PEG_{200}DA$ and $PEG_{700}DA$ samples: $P=a\cdot\exp[-t/\tau(Y)]+(1-a)\cdot\exp[-t/\tau(R)]$, with τ(R) an average of forms R and O for the $PEG_{700}DA$ sample. Three-exponential fit was used for $PEG_{400}DA$ and $PEG_{575}DA$ samples: $P=a\cdot\exp[-t/\tau(Y)]+b\cdot\exp[-t/\tau(R)]+(1-a-b)\cdot\exp[-t/\tau(O)]$, where Y, R, and O represent the yellow, red and orange needle forms respectively.
*τ, an average induction time of Form R and ON, given the lack of data points to distinguish the two.

In FIG. 31: Polymorph frequency of occurrence in 12 mg/ml ROY-ethanol solution with or without microgels of various mesh sizes (left) and at higher solution concentrations, $C_0$ (right). Frequency of occurrence is calculated as the percentage of samples crystallized in a particular form within 1440 min out of the total number of samples. The analysis for 12 mg/ml solution is carried out previously. In summary, addition of PEGDA microgels accelerated crystallization of all three forms, Y, R and ON. Particularly, nucleation of a metastable form R was preferentially induced as to become the dominant form at an optimum mesh size M=575 g/mol, whereas Y crystallized almost exclusively without any microgels. Nucleation of another metastable form ON was also promoted when M>200 g/mol, however, to a much less extent compared with R. Interestingly, ROY nucleation kinetics is extraordinarily sensitive to the variation in mesh sizes, particularly Form R.

Mechanistic investigations into ROY polymorph selectivity: The impact of microgels on ROY polymorphic outcome can be comprehended from the perspectives of the concentration effect, the templating effect, and the mesh size effect. Similar to CBZ, ROY also exhibits preferential partitioning in the gel phase (see Table 13), which leads to concentrations 6-11 times as high as that of the bulk solution. This result is visibly reflected in the red color of microgels (FIG. 30f) imparted from highly concentrated ROY. Besides, the fact that κ is much higher at larger M indicates ROY predominantly interacts with the PEG subchain. The influence of higher solute concentration on polymorphic outcomes was investigated with bulk crystallization experiments (FIG. 31 right). ON became the dominant form with the increase of concentration, which is in accordance with previous reports. This concentration effect may explain accelerated nucleation of ON when microgels with M=400-700 g/mol were added (FIG. 31 left), considering that the ROY concentration in these microgels is much higher than in others (see Table 13). The concentration effect may not fully account for the observation that crystallization of R form was particularly promoted by microgels in this embodiment. The strong dependence of R form nucleation kinetics and frequency of occurrence on M may suggest that the mesh size effect and the ROY-polymer interactions may play a key role in controlling R form nucleation.

The ROY-polymer interactions were probed via preferred crystal orientations on flat $PEG_MDA$ films. From the bulk solution, ROY crystallized in Form Y predominantly. In comparison, $PEG_MDA$ films templated nucleation of R, as well as Y, which is consistent with the observations with microgels. In particular, a few crystal facets show much stronger XRD peak intensities compared with the bulk sample, i.e., Y (020), R (111) and R (220), indicating that they are the dominant crystal facets nucleated on the polymer. To verify this observation, the contribution from each crystal facet was quantified and listed the prominent ones in Table 12. The preferred crystal orientation varied significantly as a function of M, the PEG subchain molecular weight. Polymers with M=130, 200 g/mol favor R (111) and R (220). As M increases, percentage of R decreases and Y increases to become the dominant polymorph on M=575, 700 g/mol, which is contact with the polymer via Y (020) and/or (040) facet. This observation may suggest that the acrylate group of PEGDA could be responsible for templating R, whereas the PEG subchain induced nucleation of Y. The polymorph crystallization was sensitive to polymer-solute interactions.

XRD patterns of ROY crystallized from bulk solution and on PEGDA films under the substantially similar conditions were obtained. Additional peaks observed from crystals templated by polymer films but not from bulk crystals were observed. Reference patterns were calculated from CSD using POWD-12++.

TABLE 12

Percentages of ROY crystals in various orientations (hkl) on $PEG_MDA$ polymer films.

| M (g/mol) | Y (020), % | Y (040), % | R (111), % | R (220), % |
|---|---|---|---|---|
| 130 | 7.5 | 3.4 | 38.0 | 46.8 |
| 200 | 3.5 | 1.6 | 36.2 | 53.6 |
| 400 | 23.6 | 9.9 | 28.8 | 24.9 |
| 575 | 26.9 | 13.1 | 12.9 | 20.0 |
| 700 | 50.9 | 16.9 | 9.8 | 14.4 |

Analysis on the XRD data is carried out by normalizing the measured peak intensities $I_p^i$ with the reference peak intensities $I_{bulk}^i$ from the bulk sample, following the formula $$\eta_i = \frac{I_p^i / I_{bulk}^i}{\sum_i (I_p^i / I_{bulk}^i)} \times 100,$$

where $\eta_i$ is the percentage of crystals in orientation i, and p is short for polymer. Minor orientations (<10% on all films) are considered but not shown in the table. Percentages are highlighted as bold for dominant orientations in each case.

TABLE 13

| | M (g/mol) | | | | |
|---|---|---|---|---|---|
| | 130 | 200 | 400 | 575 | 700 |
| CBZ | 3.0 ± 0.4 | 2.7 ± 0.1 | 3.8 ± 0.2 | 3.8 ± 0.04 | 3.7 ± 0.1 |
| ROY | 6.3 ± 0.2 | 6.1 ± 0.9 | 11.0 ± 0.4 | 11.3 ± 1.6 | 11.8 ± 1.1 |

Figure 32:
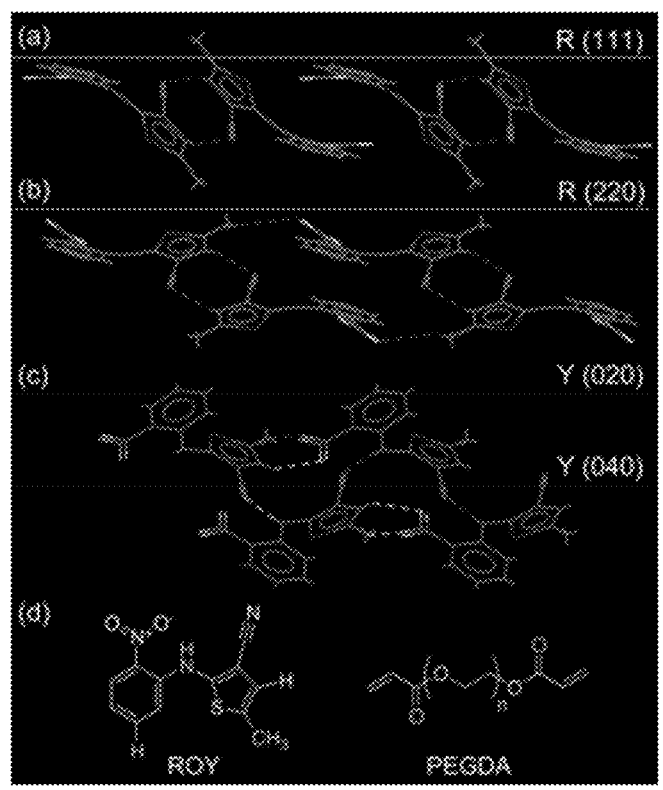
FIG. 32 shows specific polymer-ROY interactions inferred from preferred crystal orientations, according to some embodiments.

Partition coefficients (κ) of CBZ and ROY in $PEG_MDA$ microgels from ethanol solutions. κ is defined as the ratio of solute mass fraction in solution confined in the gel to that in the bulk. The error bars are calculated from three to four independent repeats. To study the specific polymer-solute interactions, the molecular structures of preferentially nucleated crystal facets was examined as shown in FIG. 32. R (111) and R (220) exhibited very similar surface functionalities. The cyano and nitro moieties, although exposed to the surface, were engaged in ROY self-interactions, leaving the amine and methyl groups more available to interact with the polymer surface (FIG. 32d), probably with the acrylate group as inferred from the XRD results (Table 12). Specifically, the amine hydrogen of ROY can form hydrogen bond with the carbonyl of acrylate group, and the methyl group of ROY can interact with acrylate by forming C—H . . . O contact, which is often referred to as a secondary hydrogen bond As for Form Y, either Y (020) or Y (040) or both were possibly templated by the polymer, which cannot be distinguished from the XRD results since they are parallel planes. However, it is unlikely for Y (040) would associate with PEGDA because it resembles Y (022) and Y (042) in surface chemistry (not shown), which are not favored by the polymer but are among the main facets of bulk crystals. All Y (022), (042) and (040) facets are featured with cyano and/or nitro moieties, which are more likely to engage in ROY intermolecular interactions or solvated by ethanol. Therefore, the phenolic hydrogen exposed to the Y (020) surface can be inferred to be responsible for interacting with the PEG subchain (FIG. 32d), probably by forming C—H . . . O contact with the ethylene oxide oxygen.

The identified specific ROY-polymer interactions may help elucidate the role of templating effect in polymorph selection. By interacting with the phenolic hydrogen of ROY, the PEG subchain may cause two effects. First, it can help align the ROY molecules in a particular orientation, and as such better exposes other moieties in ROY for self-interactions and facilitates molecular clusters formation, which is a key step to nucleation. Second, it can hinder the phenolic hydrogen-nitro recognition essential to R polymorph formation (not found in other forms with known structures except for OPR), resulting in preferential nucleation of Y polymorph on polymer films with higher M. Likewise, by hydrogen bonding with the amine moiety of ROY, the acrylate group of the polymer can interfere with the amine-cyano hydrogen bond unique to Y polymorph (not found in other forms), and as such facilitates crystallization of R polymorph.

In FIG. 32: Specific polymer-ROY interactions inferred from preferred crystal orientations. (a-c) Molecular structures of ROY crystal facets preferentially grown from the polymer surface. The solid line indicates the top surface of the corresponding facet. R and Y denote red and yellow ROY polymorphs. Prominent intermolecular interactions in ROY crystals are denoted with green dotted lines if the interaction is between the two in-plane molecules as depicted, and with dotted lines if it is between one in-plane molecule and another molecule in the next layer in through-plane direction. (d) Molecular structures of monomers of ROY and PEGDA. ROY functional groups colored blue are inferred to preferentially interact with PEG subchain, and those colored red with the acrylate group.

Molecular recognition motifs in ROY crystals of forms Y (a-b) and R (c-d) were prepared and both intermolecular interactions and intramolecular interactions were determined. Other supermolecular rings may form by different combinations of the same set of intermolecular interactions.

Following the above discussions, the templating effect of the microgels alone is may bias the polymorph selectivity towards R at lower M and Y at higher M. Observed continuous nucleation acceleration of Form Y with an increase in M (Tables 10 and 11), however, the trend of R may be influenced by more than the templating effect and the concentration effect Regarding the mesh size effect, the existence of an optimum mesh size for expediting nucleation of R, at which point, its frequency of occurrence was kinetically driven to a maximum. The optimum mesh size may arise from the interplay between polymer-solute interactions and spatial confinement imposed by the polymer mesh. Specifically, when the mesh size is too small, most of solute molecules are adsorbed to the tightly intertwined polymer chain given the large volume fraction of polymers, thereby reducing the molecular mobility and hindering effective solute-solute interactions essential to nucleus formation (FIG. 33a); when the mesh size is too large, a smaller fraction of solute is associated with the polymer and the nucleation-templating effect of the polymer due to specific polymer-solute interactions is much less significant (FIG. 33c); at the optimum mesh size, the polymer-solute and solute-solute interactions are balanced, enabling the solute molecules aligned by adjacent polymer chains to act concertedly in forming the nucleus given appropriate spacing (FIG. 33b). This hypothesis implies that the optimum mesh size may not be the same for polymorphs of the same compound, since their nucleation events are templated by different specific polymer-solute interactions as discussed above, and the spacing required for molecular cooperativity may differ as well. For ROY system, the separation of optimum mesh sizes between Y and R is central to the observed favorable polymorph selectivity towards R at M=575 g/mol, which overcomes the opposite trend of templating effect that favors Y with increasing M. As for the CBZ system, the mesh size effect is also evident (Table 9). There exhibited an optimum mesh size at M=400 g/mol corresponding to the fastest nucleation rate of Form II, whose mass fraction concurrently attained maximum. The polymorph selectivity maintained at 100% even when M increased beyond optimum, probably because the mesh size effect was counterbalanced by the templating and concentration effect, which favored Form II at higher M.

Figure 33:
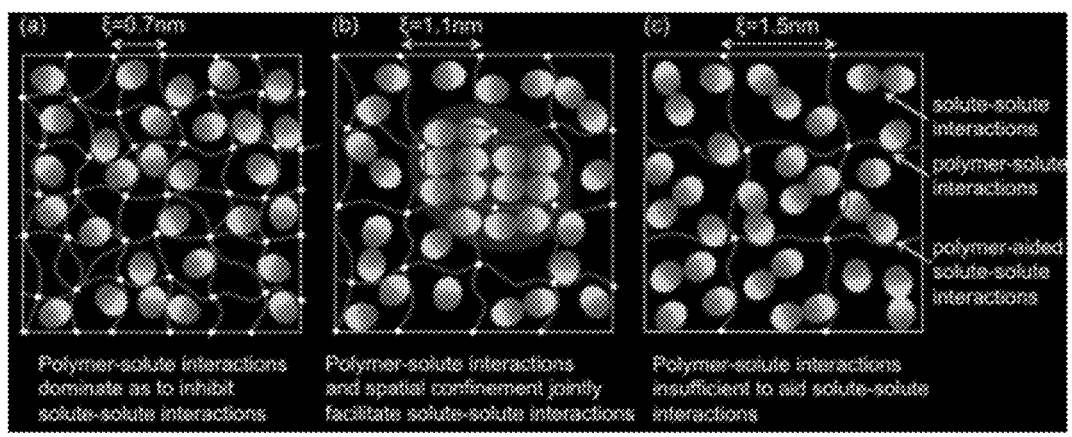
FIG. 33 shows schematics illustrating the mesh size effect on nucleation, according to some embodiments.

In FIG. 33: Schematic illustrating the mesh size effect on nucleation. Lines denote the polymer mesh with crosslinking points indicated using small circles. The polymer mesh drawn here not necessarily represents the actual physical model, but is sufficient to illustrate the role of varying confinement size. Solute molecules are signified with ellipsoids, whose one end is colored darker grey and preferentially interacts with the polymer chain, and the other end color colored lighter grey responsible for self-interactions. One example of such molecules is CBZ, with the darker grey end corresponding to the vinyl group on the azepine ring that interacts with the PEG subchain, and the lighter grey end corresponding to the carboxamide group, which dimerizes in CBZ crystals. The molar ratios of solute to monomer units constituting the polymer are drawn to scale, which are calculated from CBZ partitioning experiments. The relative size of the solute to the mesh size is also drawn to scale approximately for CBZ system. The relative fraction of solute molecules adsorbed to the polymer chain is estimated by assuming that the number of solute binding sites scales linearly with the PEG subchain length. The optimum mesh size for CBZ nucleation was found to be 1.1 m (Table 9). Therefore the nucleus formation is illustrated in (b) as highlighted with yellow background.

In conclusion, the polymer microgels were demonstrated as materials for controlling crystallization of polymorphs. PEGDA microgels selectively induced nucleation of Form II of CBZ, while concomitant crystallization of Form I and II were observed from bulk. In another example, the microgels improved ROY polymorph selectivity towards Form R by up to 20 times, whereas bulk crystallization predominantly produced Y or ON depending on the supersaturation. Through these examples, the polymer gels showed ability to take the polymorphic system into occurrence domains not accessible through conventional methods. Furthermore, through these mechanistic investigations, the nucleation-templating effect and the spatial confinement imposed by the polymer network were important in achieving polymorph selectivity. With this insight, selective crystallization of a desired polymorph can be achieved by designing the polymer chemistry and microstructure.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method of making a pharmaceutical product, comprising:
   crystallizing a pharmaceutically active agent on at least one surface of or associated with at least one excipient, wherein the at least one excipient promotes crystallization of the pharmaceutically active agent and the at least one excipient comprises an imprinted surface having a plurality of surface features selected to be complimentary to a known shape and/or angle(s) of a selected known crystal structure of the pharmaceutically active agent; and
   forming a pharmaceutically acceptable composition comprising the pharmaceutically active agent and the at least one excipient, wherein the process is free or essentially free of mechanical steps for combining the pharmaceutically active agent with the at least one excipient wherein the at least one excipient comprises a plurality of particles.

2. The method of claim 1, wherein the pharmaceutically active agent is aspirin or acetaminophen.

3. The method of claim 1, wherein the at least one excipient comprises a polymeric material.

4. The method of claim 3, wherein the polymeric material is a hydrogel.

5. The method of claim 4, wherein the polymeric material is formed using UV polymerization.

6. The method of claim 4, wherein the polymeric material is formed by reacting at least one monomer and a crosslinking agent using UV irradiation.

7. The method of claim 1, wherein the plurality of surface features comprises a plurality of wells.

8. The method of claim 1, wherein the shape of the surface features are triangles, squares, rectangles, trapezoids, pentagons, hexagons, or octagons.

9. The method of claim 1, wherein the surface features have an average cross section of greater than about 10 nm.

10. The method of claim 1, wherein the surface features have an average cross section between about 10 nm and about 1000 nm.

11. The method of claim 10, wherein the surface features have an average depth of less than about 10 mm.

12. The method of claim 1, wherein the surface features have an average depth of between about 50 nm and about 1 nm.

13. The method of claim 1, wherein a portion of the surface comprises a plurality of functional groups complimentary to a plurality of functional groups of the pharmaceutically active agent.

14. The method of claim 13, wherein the surface comprising the plurality of functional groups is the surface comprising the plurality of surface features.

15. The method of claim 13, wherein the plurality of functional groups comprises a plurality of hydroxyl functional groups, a plurality of carboxylic acid ester functional groups, a plurality of nitrogen containing base functional group, a plurality of aryl functional groups, a plurality of carboxyl functional group, a plurality of tertiary amide functional groups, or combinations thereof.

16. The method of claim 1, wherein the plurality of particles have an average diameter of less than about 5 mm.

17. The method of claim 1, wherein the surface features have an average cross section between about 10 nm and about 500 nm.

18. The method of claim 1, wherein the surface features have an average cross section between about 10 nm and about 100 nm.

19. The method of claim 10, wherein the surface features have an average depth of less than about 500 nm.

20. The method of claim 10, wherein the surface features have an average depth of less than about 5 nm.

21. The method of claim 1, wherein the surface features have an average depth of between about 30 nm and about 1 nm.

22. The method of claim 1, wherein the surface features have an average depth of between about 10 nm and about 1 nm.

23. The method of claim 1, wherein the pharmaceutically active agent is a small organic molecule.

24. The method of claim 1, wherein the pharmaceutically active agent is substantially crystallized having the selected crystal structure.

25. The method of claim 1, wherein the imprinted surface is formed via nanoimprint lithography.

26. The method of claim 1, wherein the imprinted surface reduces an average induction time of the pharmaceutically active agent having the selected known crystal structure as compared to a surface lacking the plurality of surface features under substantially similar conditions.

* * * * *